US010729676B2

(12) United States Patent
Anandan et al.

(10) Patent No.: US 10,729,676 B2
(45) Date of Patent: Aug. 4, 2020

(54) OPIOID AGONIST PEPTIDES AND USES THEREOF

(71) Applicant: Protagonist Therapeutics, Inc., Newark, CA (US)

(72) Inventors: Sampath Kumar Anandan, Fremont, CA (US); Jie Zhang, Newark, CA (US); Ashok Bhandari, Pleasanton, CA (US); Gregory Thomas Bourne, Brisbane (AU); Brian Troy Frederick, Ben Lomond, CA (US); Larry C. Mattheakis, Cupertino, CA (US); David Liu, Newark, CA (US); Mukund M. Mehrotra, Newark, CA (US)

(73) Assignee: Protagonist Theraputics, Inc., Newark, CA (US)

(*) Notice: Subject to any disclaimer, the term of this patent is extended or adjusted under 35 U.S.C. 154(b) by 0 days.

(21) Appl. No.: 16/294,717

(22) Filed: Mar. 6, 2019

(65) Prior Publication Data
US 2019/0231746 A1    Aug. 1, 2019

Related U.S. Application Data

(62) Division of application No. 16/128,352, filed on Sep. 11, 2018, now Pat. No. 10,278,957.

(60) Provisional application No. 62/663,660, filed on Apr. 27, 2018, provisional application No. 62/556,900, filed on Sep. 11, 2017.

(51) Int. Cl.
*A61K 31/4045* (2006.01)
*A61K 38/08* (2019.01)
*A61P 1/00* (2006.01)
*A61P 29/00* (2006.01)
*A61K 38/38* (2006.01)

(52) U.S. Cl.
CPC .......... *A61K 31/4045* (2013.01); *A61K 38/08* (2013.01); *A61K 38/38* (2013.01); *A61P 1/00* (2018.01); *A61P 29/00* (2018.01)

(58) Field of Classification Search
CPC ............................. A61K 31/4045; A61K 38/08
See application file for complete search history.

(56) References Cited

U.S. PATENT DOCUMENTS

| | | |
|---|---|---|
| 4,495,178 A | 1/1985 | Hansen et al. |
| 4,684,620 A | 8/1987 | Hruby et al. |
| 4,722,922 A | 2/1988 | Hansen et al. |
| 4,724,229 A | 2/1988 | Ali |
| 5,162,500 A | 11/1992 | Takeuchi et al. |
| 5,180,816 A | 1/1993 | Dean |
| 5,192,746 A | 3/1993 | Lobl et al. |
| 5,382,569 A | 1/1995 | Cody et al. |
| 5,663,295 A | 9/1997 | Moreau et al. |
| 5,990,084 A | 11/1999 | Richter et al. |
| 6,087,334 A | 7/2000 | Beeley et al. |
| 6,121,489 A | 9/2000 | Dorner et al. |
| 6,187,905 B1 | 2/2001 | Hurst et al. |
| 6,235,711 B1 | 5/2001 | Dutta |
| 6,818,617 B1 | 11/2004 | Niewiarowski |
| 7,534,764 B2 | 5/2009 | Ganz et al. |
| 7,553,969 B1 | 6/2009 | Matsuoka et al. |
| 8,313,950 B2 | 11/2012 | Rovin et al. |
| 8,435,941 B2 | 5/2013 | Ganz et al. |
| 8,536,140 B2 | 9/2013 | Clandinin et al. |
| 8,568,706 B2 | 10/2013 | Grabstein et al. |
| 8,716,436 B2 | 5/2014 | Zadina et al. |
| 8,796,418 B2 | 8/2014 | Walensky et al. |
| 8,946,150 B2 | 2/2015 | Gallagher et al. |
| 8,999,935 B2 | 4/2015 | Huang |
| 9,169,292 B2 | 10/2015 | Gallagher et al. |
| 9,273,093 B2 | 3/2016 | Bhandari et al. |
| 9,518,091 B2 | 12/2016 | Bhandari et al. |
| 9,624,268 B2 | 4/2017 | Bourne et al. |
| 9,714,270 B2 | 7/2017 | Bhandari et al. |
| 9,809,623 B2 | 11/2017 | Bhandari et al. |
| 9,822,157 B2 | 11/2017 | Smythe et al. |
| 10,023,614 B2 | 7/2018 | Bhandari et al. |
| 10,030,061 B2 | 7/2018 | Smythe et al. |
| 10,035,824 B2 | 7/2018 | Bhandari et al. |
| 10,059,744 B2 | 8/2018 | Bhandari et al. |
| 10,196,424 B2 | 2/2019 | Bourne et al. |
| 10,278,957 B2 | 5/2019 | Anandan et al. |
| 10,301,371 B2 | 5/2019 | Bhandari et al. |
| 10,442,846 B2 | 10/2019 | Smythe et al. |
| 10,501,515 B2 | 12/2019 | Smythe et al. |
| 2002/0103133 A1 | 8/2002 | Copeland et al. |
| 2002/0115612 A1 | 8/2002 | Zuckermann et al. |
| 2003/0166138 A1 | 9/2003 | Kinsella et al. |
| 2003/0166514 A1 | 9/2003 | Jones et al. |
| 2004/0052785 A1 | 3/2004 | Goodman et al. |
| 2004/0116339 A1 | 6/2004 | Villanueva et al. |

(Continued)

FOREIGN PATENT DOCUMENTS

| | | |
|---|---|---|
| AU | 2011274522 B2 | 3/2016 |
| CA | 2810170 A1 | 1/2012 |

(Continued)

OTHER PUBLICATIONS

U.S. Appl. No. 15/486,684, filed Apr. 13, 2017, Bhandari et al.

(Continued)

*Primary Examiner* — Amber D Steele

(74) *Attorney, Agent, or Firm* — Cooley LLP

(57) ABSTRACT

The invention is directed to opioid agonist peptides and their use.

18 Claims, 3 Drawing Sheets

Specification includes a Sequence Listing.

(56) References Cited

U.S. PATENT DOCUMENTS

| | | |
|---|---|---|
| 2004/0167069 A1 | 8/2004 | Khosla et al. |
| 2004/0176293 A1 | 9/2004 | Peterson et al. |
| 2004/0209857 A1 | 10/2004 | Dolle et al. |
| 2006/0183884 A1 | 8/2006 | Blaschuk et al. |
| 2007/0027067 A1 | 2/2007 | Etzkorn |
| 2007/0032417 A1 | 2/2007 | Baell |
| 2007/0166308 A1 | 7/2007 | Pullen et al. |
| 2007/0197430 A1 | 8/2007 | Baell et al. |
| 2007/0293656 A1 | 12/2007 | Caravan et al. |
| 2008/0019913 A1 | 1/2008 | Polt et al. |
| 2008/0039404 A1 | 2/2008 | Hruby et al. |
| 2008/0213277 A1 | 9/2008 | Sasu et al. |
| 2008/0260820 A1 | 10/2008 | Borrelly et al. |
| 2008/0300180 A1 | 12/2008 | Schambye et al. |
| 2009/0048161 A1 | 2/2009 | Chemtob et al. |
| 2009/0053819 A1 | 2/2009 | Seymour et al. |
| 2009/0257952 A1 | 10/2009 | Cochran et al. |
| 2010/0151487 A1 | 6/2010 | Rovin et al. |
| 2010/0190710 A1 | 7/2010 | Chemtob et al. |
| 2010/0196441 A1 | 8/2010 | Sondermeijer et al. |
| 2010/0272731 A1 | 10/2010 | Presta et al. |
| 2010/0280098 A1 | 11/2010 | Juliano et al. |
| 2011/0002855 A1 | 1/2011 | Caldwell et al. |
| 2011/0059087 A1 | 3/2011 | Lewis et al. |
| 2011/0086024 A1 | 4/2011 | Arthos et al. |
| 2011/0112137 A1 | 5/2011 | Eissenstat et al. |
| 2011/0118186 A1 | 5/2011 | Schteingart et al. |
| 2011/0282029 A1 | 11/2011 | Holmes et al. |
| 2012/0021530 A1 | 1/2012 | Gellman et al. |
| 2012/0021975 A1 | 1/2012 | Hoffman et al. |
| 2012/0071422 A1 | 3/2012 | Gallagher et al. |
| 2012/0115930 A1 | 5/2012 | Monia et al. |
| 2012/0322740 A1 | 12/2012 | Zadina et al. |
| 2013/0029907 A1 | 1/2013 | Gallagher et al. |
| 2013/0137630 A1 | 5/2013 | Appleyard et al. |
| 2013/0158021 A1 | 6/2013 | Dong et al. |
| 2013/0165624 A1 | 6/2013 | Geysen |
| 2013/0172272 A1 | 7/2013 | Gallagher et al. |
| 2013/0178427 A1 | 7/2013 | Zadina et al. |
| 2013/0183755 A1 | 7/2013 | Gallagher et al. |
| 2013/0196899 A1 | 8/2013 | Zecri et al. |
| 2013/0310303 A1 | 11/2013 | Eldar-Finkelman et al. |
| 2014/0005128 A1 | 1/2014 | Mo et al. |
| 2014/0142022 A1 | 5/2014 | Zecri et al. |
| 2014/0193465 A1 | 7/2014 | Bhandari et al. |
| 2014/0286953 A1 | 9/2014 | Sasu et al. |
| 2014/0294901 A1 | 10/2014 | Bhandari et al. |
| 2014/0294902 A1 | 10/2014 | Bhandari et al. |
| 2014/0336110 A1 | 11/2014 | Ganz et al. |
| 2015/0056301 A1 | 2/2015 | Kawabe et al. |
| 2015/0118315 A1* | 4/2015 | Wilson .................. A61K 38/10 424/490 |
| 2015/0157692 A1 | 6/2015 | Fu |
| 2015/0203555 A1 | 7/2015 | Gellman et al. |
| 2015/0284429 A1 | 10/2015 | Merutka |
| 2015/0315238 A1 | 11/2015 | Zadina et al. |
| 2016/0009764 A1 | 1/2016 | Zadina et al. |
| 2016/0031944 A1 | 2/2016 | Bhandari et al. |
| 2016/0039878 A1 | 2/2016 | Gallagher et al. |
| 2016/0145306 A1 | 5/2016 | Bourne et al. |
| 2016/0152664 A1 | 6/2016 | Bhandari et al. |
| 2016/0159862 A1 | 6/2016 | Bhandari et al. |
| 2016/0176930 A1 | 6/2016 | Zadina et al. |
| 2016/0199437 A1* | 7/2016 | Wilson ................ A61K 31/444 424/130.1 |
| 2016/0222076 A1 | 8/2016 | Smythe et al. |
| 2016/0228491 A1* | 8/2016 | Wilson ............... A61K 31/5415 |
| 2016/0361378 A1 | 12/2016 | Hruby et al. |
| 2016/0368966 A1 | 12/2016 | Bhandari et al. |
| 2017/0014468 A1 | 1/2017 | Dominy et al. |
| 2017/0107255 A1 | 4/2017 | Holder et al. |
| 2017/0313754 A1 | 11/2017 | Bourne et al. |
| 2017/0327541 A1 | 11/2017 | Bhandari et al. |
| 2018/0022778 A1 | 1/2018 | Bourne et al. |
| 2018/0079782 A1 | 3/2018 | Bhandari et al. |
| 2018/0079783 A1 | 3/2018 | Bhandari et al. |
| 2018/0099995 A1 | 4/2018 | Bhandari et al. |
| 2018/0100004 A1 | 4/2018 | Smythe et al. |
| 2018/0105572 A1 | 4/2018 | Bhandari et al. |
| 2018/0148477 A1 | 5/2018 | Bhandari et al. |
| 2019/0002500 A1 | 1/2019 | Bhandari et al. |
| 2019/0002503 A1 | 1/2019 | Bourne et al. |
| 2019/0016756 A1 | 1/2019 | Bhandari et al. |
| 2019/0076400 A1 | 3/2019 | Anandan et al. |
| 2019/0185535 A1 | 6/2019 | Smythe et al. |
| 2019/0185536 A1 | 6/2019 | Smythe et al. |
| 2019/0248870 A1 | 8/2019 | Bhandari et al. |
| 2019/0270786 A1 | 9/2019 | Bhandari et al. |
| 2019/0300590 A1 | 10/2019 | Bhandari et al. |
| 2019/0337983 A1 | 11/2019 | Bhandari et al. |

FOREIGN PATENT DOCUMENTS

| | | |
|---|---|---|
| DE | 2703109 A1 | 8/1977 |
| DE | 3320175 A1 | 12/1984 |
| DE | 10107707 A1 | 8/2002 |
| EP | 0136720 A2 | 4/1985 |
| EP | 0163237 A2 | 12/1985 |
| EP | 0292255 A2 | 11/1988 |
| EP | 0350221 A2 | 1/1990 |
| EP | 0614913 A2 | 9/1994 |
| EP | 02590992 A2 | 5/2013 |
| EP | 02590992 B1 | 4/2017 |
| JP | S53119845 A | 10/1978 |
| JP | 2011-231085 A | 11/2011 |
| JP | 2016-084357 A1 | 5/2016 |
| WO | WO 1990/012805 A1 | 11/1990 |
| WO | WO 1992/017492 A1 | 10/1992 |
| WO | WO 1994/006451 A1 | 3/1994 |
| WO | WO 1994/011018 A1 | 5/1994 |
| WO | WO 1994/014843 A1 | 7/1994 |
| WO | WO 1997/025351 A2 | 7/1997 |
| WO | WO 1998/008871 A1 | 3/1998 |
| WO | WO 2000/055184 A1 | 3/1998 |
| WO | WO 1999/002194 A1 | 1/1999 |
| WO | WO 1999/019356 A1 | 4/1999 |
| WO | WO 1999/026615 A1 | 6/1999 |
| WO | WO 2000/006243 A2 | 2/2000 |
| WO | WO 2000/009560 A1 | 2/2000 |
| WO | WO 2000/018789 A1 | 4/2000 |
| WO | WO 2000/018790 A1 | 4/2000 |
| WO | WO 2000/023474 A1 | 4/2000 |
| WO | WO 2000/044770 A1 | 8/2000 |
| WO | WO 2000/055119 A1 | 9/2000 |
| WO | WO 2000/061580 A1 | 10/2000 |
| WO | WO 2001/068586 A2 | 9/2001 |
| WO | WO 2003/066678 A1 | 8/2003 |
| WO | WO 2003/096979 A2 | 11/2003 |
| WO | WO 2004/011650 A2 | 2/2004 |
| WO | WO 2004/018644 A2 | 3/2004 |
| WO | WO 2004/092405 A2 | 10/2004 |
| WO | WO 2005/105830 A1 | 11/2005 |
| WO | WO 2006/032104 A1 | 3/2006 |
| WO | WO 2006/124494 A1 | 11/2006 |
| WO | WO 2007/064919 A2 | 6/2007 |
| WO | WO 2007/084264 A2 | 7/2007 |
| WO | WO 2007/138291 A2 | 12/2007 |
| WO | WO 2008/097461 A2 | 8/2008 |
| WO | WO 2008/134659 A2 | 11/2008 |
| WO | WO 2008/140602 A1 | 11/2008 |
| WO | WO 2009/002947 A2 | 12/2008 |
| WO | WO 2009/003003 A2 | 12/2008 |
| WO | WO 2009/007849 A2 | 1/2009 |
| WO | WO 2009/027752 A2 | 3/2009 |
| WO | WO 2009/105782 A1 | 8/2009 |
| WO | WO 2010/065815 A2 | 6/2010 |
| WO | WO 2010/116752 A1 | 10/2010 |
| WO | WO 2010/124874 A1 | 11/2010 |
| WO | WO 2011/091357 A1 | 7/2011 |
| WO | WO 2011/149942 A2 | 12/2011 |
| WO | WO 2012/006497 A2 | 1/2012 |
| WO | WO 2012/020219 A2 | 2/2012 |
| WO | WO 2012/052205 A1 | 4/2012 |
| WO | WO 2012/006497 A3 | 5/2012 |

(56) References Cited

FOREIGN PATENT DOCUMENTS

| WO | WO 2012/138941 A1 | 10/2012 | | |
|---|---|---|---|---|
| WO | WO 2013/063468 A1 | 5/2013 | | |
| WO | WO 2013/086143 A1 | 6/2013 | | |
| WO | WO 2013/096939 A1 | 6/2013 | | |
| WO | WO 2014/059213 A1 | 4/2014 | | |
| WO | WO 2014/127316 A2 | 8/2014 | | |
| WO | WO 2014/137496 A1 | 9/2014 | | |
| WO | WO 2014/145561 A2 | 9/2014 | | |
| WO | WO 2014/165448 A1 | 10/2014 | | |
| WO | WO 2014/165449 A1 | 10/2014 | | |
| WO | WO 2014/210056 | * | 12/2014 | ............ A61K 38/08 |
| WO | WO 2015/086686 A2 | 6/2015 | | |
| WO | WO 2015/127451 A1 | 8/2015 | | |
| WO | WO 2015/157283 A9 | 10/2015 | | |
| WO | WO 2015/176035 A1 | 11/2015 | | |
| WO | WO 2015/183963 | * | 12/2015 | ............ A61K 38/07 |
| WO | WO 2015/191781 A2 | 12/2015 | | |
| WO | WO 2015/200916 A2 | 12/2015 | | |
| WO | WO 2016/011208 A1 | 1/2016 | | |
| WO | WO 2016/054411 A1 | 4/2016 | | |
| WO | WO 2016/054445 A1 | 4/2016 | | |
| WO | WO 2016/109363 A1 | 7/2016 | | |
| WO | WO 2016/187537 A1 | 11/2016 | | |
| WO | WO 2016/004093 | * | 12/2016 | ............ A61K 38/10 |
| WO | WO 2016/195663 | * | 12/2016 | ............ A61K 38/07 |
| WO | WO 2016/200364 | * | 12/2016 | ........... A61K 31/662 |
| WO | WO 2017/009358 A1 | 1/2017 | | |
| WO | WO 2017/011820 A2 | 1/2017 | | |
| WO | WO 2017/117411 A1 | 7/2017 | | |
| WO | WO 2018/022937 A1 | 2/2018 | | |
| WO | WO 2018/136646 A1 | 7/2018 | | |

OTHER PUBLICATIONS

U.S. Appl. No. 15/493,471, filed Apr. 21, 2017, Bhandari et al.
U.S. Appl. No. 15/831,099, filed Dec. 4, 2017, Bhandari, et al.
U.S. Appl. No. 15/831,120, filed Dec. 4, 2017, Bhandari, et al.
U.S. Appl. No. 15/745,371, filed Jan. 16, 2018, Bhandari, et al.
U.S. Appl. No. 16/035,060, filed Jul. 13, 2018, Bhandari, et al.
U.S. Appl. No. 16/037,982, filed Jul. 17, 2018, Smythe, et al.
U.S. Appl. No. 16/113,072, filed Aug. 27, 2018, Bhandari, et al.
U.S. Appl. No. 16/128,352, filed Sep. 11, 2018, Anandan, et al.
U.S. Appl. No. 16/217,864, filed Dec. 12, 2018, Bourne, et al.
U.S. Appl. No. 16/282,908, filed Feb. 22, 2019, Bhandari, et al.
U.S. Appl. No. 16/282,920, filed Feb. 22, 2019, Bhandari, et al.
U.S. Appl. No. 16/319,958, filed Jan. 23, 2019, Bhandari, et al.
Adams and Macmillan, "Investigation of peptide thioester formation via N→Se acyl transfer." Journal of Peptide Science (2013) 19 (2): 65-73.
Ananda, et al., "Polypeptide Helices in Hybrid Peptide Sequences." Journal of the American Chemical Society (2005); 127(47): 16668-16674.
Ashby, et al., "Plasma hepcidin levels are elevated but responsive to erythropoietin therapy in renal disease." Kidney International (2009); 75 (9): 976-981.
Bailey, et al., "A structural comparison of 21 inhibitor complexes of the aspartic proteinase from Endothia parasitica." Protein Science (1994); 3(11): 2129-2143.
Boer, J., et al., "Design and Synthesis of Potent and Selective $\alpha_4\beta_7$ Integrin Antagonists." J. Med. Chem. (2001); 44 (16): 2586-2592.
Boersma, et al., "Evaluation of Diverse α/β-Backbone Patterns for Functional α-Helix Mimicry: Analogues of the Bim BH3 Domain." Journal of the American Chemical Society (2012); 134(1): 315-323.
Bowie, et al., "Deciphering the Message in Protein Sequences: Tolerance to Amino Acid Substitutions." Science (1990); 247: 1306-1310.
Cardillo, et al., "Endomorphin-1 Analogues Containing β-Proline Are μ-Opioid Receptor Agonists and Display Enhanced Enzymatic Hydrolysis Resistance." Journal of Medicinal Chemistry (2002); 45(12): 2571-2578.

Chatterjee, J. et al., "N-Methylation of Peptides: a New Perspective in Medicinal Chemistry", Accounts of Chemical Research, 41(10): 1331-1342 (2008).
Cheloha, et al., "Consequences of Periodic α-to-β3 Residue Replacement for Immunological Recognition of Peptide Epitopes." ACS Chemical Biology (2015); 10(3): 844-854.
Chen, et al., "A traceless approach to amide and peptide construction from thiocarboxylic acids and dithiocarbamate-terminal amines." Chemical Science (2013); 4(3): 970-976.
Clark, Richard J., et al. "Design, synthesis, and characterization of cyclic analogues of the iron regulatory peptide hormone hepcidin." Peptide Science (2013); 100.5: 519-526.
Clark, et al., "Understanding the Structure/Activity Relationships of the Iron Regulatory Peptide Hepcidin." Chem Biol. (Mar. 2011); 18(3): 336-343.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from patent U.S. Pat. No. 8,313,950.", XP002761650, retrieved from EBI accession No. USPOP:AGA36544 Database accession No. AGA36544, 1 page.
De Mast, et al., "Increased serum hepcidin and alterations in blood iron parameters associated with asymptomatic P. falciparum and P. vivax malaria." Haematologica (2010); 95 (7): 1068-1074.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)-Mediated Cell Adhesion Based on the Ile-Leu-Asp-Val Tetrapeptide", J. Peptide Sci. (2000); 6: 321-341.
European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Extended European Search Report dated Feb. 17, 2017, 9 pages.
European Application No. 14780207.8, Partial Supplementary European Search Report dated Nov. 16, 2016, 6 pages.
European Application No. 15792950.6, Extended European Search Report dated May 2, 2018, 10 pages.
European Application No. 15812513.8, Extended European Search Report dated Apr. 12, 2018, 11 pages.
European Application No. 15821351.2, Extended European Search Report dated Jan. 3, 2018, 6 pages.
European Application No. 15846131.9, Extended European Search Report dated Jan. 25, 2018, 8 pages.
European Application No. 15846983.3, Extended European Search Report dated Jun. 19, 2018, 10 pages.
European Application No. 15846983.3, Partial European Search Report dated Mar. 2, 2018, 11 pages.
European Application No. 16825301.1, Extended European Search Report dated Jan. 21, 2019, 6 pages.
Fraczak, et al., "Biphalin analogs containing β3-homo-amino acids at the 4,4' positions: Synthesis and opioid activity profiles." Peptides (2015); 66: 13-18.

(56) References Cited

OTHER PUBLICATIONS

Fraczak, et al., "Synthesis, binding affinities and metabolic stability of dimeric dermorphin analogs modified with β3-homo-amino acids." Journal of Peptide Science (2016); 22(4): 222-227.
Ganz and Nemeth, "Hepcidin and iron homeostasis." Biochimica et Biophysica Acta (BBA)—Molecular Cell Research (Sep. 2012); 1823 (9): 1434-1443.
Gee et al. "Cyclic Peptides as Non-carboxyl-terminal Ligands of Syntrophin PDZ Domains," The Journal of Biological Chemistry, 273(34): 21980-21987 (1998).
Girelli, Domenico, et al. "Hepcidin in the diagnosis of iron disorders." Blood (2016); 127.23 : 2809-2813.
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Hruby, et al., "Recent Developments in the Design of Receptor Specific Opioid Peptides." Medicinal Research Reviews (1989); 9(3): 343-401.
Hu, et al., "Synthesis and biological evaluations of novel endomorphin analogs containing α-hydroxy-β-phenylalanine (AHPBA) displaying mixed μ/δ opioidreceptor agonist and δ opioidreceptor antagonist activities." European Journal of Medicinal Chemistry (2015); 92: 270-281.
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design, (8)14: 1229-1253 (2002).
Janecka, et al., "Conformationally Restricted Peptides as Tools in Opioid Receptor Studies." Current Medicinal Chemistry (2005); 12: 471-481.
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al. "Hepcidin revisited, disulfide connectivity, dynamics, and structure." Journal of Biological Chemistry (2009); 284.36: 24155-24167.
Kelleman, A. et al., "Incorporation of thioether building blocks into an $\alpha_v\beta_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, p. 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Lesma, et al., "Structural and Biological Exploration of Phe3-Phe4-Modified Endomorphin-2 Peptidomimetics." ACS Medicinal Chemistry Letters (2013); 4(8): 795-799.
Lesma, et al., "Synthesis, pharmacological evaluation and conformational investigation of endomorphin-2 hybrid analogues." Molecular Diversity (2013); 17(1): 19-31.
Ley, Klaus, et al. "Integrin-based therapeutics: biological basis, clinical use and new drugs." Nature Reviews Drug Discovery (2016); 15.3: 173-183.
Li and Roller, "Cyclization Strategies in Peptide Derived Drug Design." Curr. Topics Med. Chem. (2002); 2: 325-341.
Liu, Shuang, "Radiolabeled Cyclic RGD Peptides as Integrin $\alpha_v\beta_3$-Targeted Radiotracers: Maximizing Binding Affinity via Bivalency." Bioconjugate Chem. (2009); 20 (12): 2199-2213.
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
Longobardo, et al., "β-Casomorphins: substitution of phenylalanine with β-homo-phenylalanine increases the μ-type opioid receptor affinity." Bioorganic & Medicinal Chemistry Letters (2000); 10(11): 1185-1188.
Madsen, Kjeld, et al. "Structure-activity and protraction relationship of long-acting glucagon-like peptide-1 derivatives: importance of fatty acid length, polarity, and bulkiness." Journal of Medicinal Chemistry (2007); 50.24: 6126-6132.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.
Mollica, et al., "Biological Active Analogues of the Opioid Peptide Biphalin: Mixed α/β3-Peptides." Journal of Medicinal Chemistry (2013); 56(8): 3419-3423.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Ossipov, et al., "Underlying Mechanisms of Pronociceptive Consequences of Prolonged Morphine Exposure." Peptide Science (2005); 80: 319-324.
Park, C.H., et al., "Hepcidin, a urinary antimicrobial peptide synthesized in the liver." J Biol Chem. (2001); 276(11): 7806-7810. Epub Dec. 11, 2000.
Parrow, et al., "Prospects for a hepcidin mimic to treat β-thalassemia and hemochromatosis." Expert Review of Hematology (2011); 4 (3): 233-235.
PCT/US2013/064439, International Preliminary Report on Patentability, dated Apr. 14, 2015, 8 pages.
PCT/US2013/064439, International Search Report and Written Opinion, dated Jan. 24, 2014, 15 pages.
PCT/US2014/030352, Invitation to Pay Additional Fees, dated Sep. 10, 2014, 2 pages.
PCT/US2014/030352, International Preliminary Report on Patentability, dated Sep. 15, 2015, 7 pages.
PCT/US2014/030352, International Search Report and Written Opinion, dated Nov. 28, 2014, 12 pages.
PCT/US2014/032391, International Preliminary Report on Patentability, dated Oct. 6, 2015, 8 pages.
PCT/US2014/032391, International Search Report, dated Aug. 7, 2014, 5 pages.
PCT/US2014/032391, Written Opinion, dated Aug. 7, 2014, 7 pages.
PCT/US2014/032392, International Preliminary Report on Patentability, dated Oct. 6, 2015, 10 pages.
PCT/US2014/032392, International Search Report and Written Opinion, dated Sep. 15, 2014, 15 pages.
PCT/US2015/031243, International Preliminary Report on Patentability, dated Nov. 22, 2016, 8 pages.
PCT/US2015/031243, International Search Report and Written Opinion, dated Aug. 5, 2015, 14 pages.
PCT/US2015/038370, International Preliminary Report on Patentability, dated Dec. 27, 2016, 4 pages.
PCT/US2015/038370, International Search Report and Written Opinion, dated Sep. 14, 2015, 5 pages.
PCT/US2015/040658, International Preliminary Report on Patentability, dated Jan. 17, 2017, 5 pages.
PCT/US2015/040658, International Search Report and Written Opinion, dated Oct. 28, 2015, 12 pages.
PCT/US2015/053558, Invitation to Pay Additional Fees, dated Dec. 16, 2015, 3 pages.
PCT/US2015/053558, International Preliminary Report on Patentability, dated Apr. 4, 2017, 9 pages.

(56) References Cited

OTHER PUBLICATIONS

PCT/US2015/053558, International Search Report and Written Opinion, dated Feb. 19, 2016, 16 pages.
PCT/US2015/053603, Invitation to Pay Additional Fees, dated Dec. 10, 2015, 3 pages.
PCT/US2015/053603, International Preliminary Report on Patentability, dated Apr. 4, 2017, 8 pages.
PCT/US2015/053603, International Search Report and Written Opinion, dated Feb. 12, 2016, 13 pages.
PCT/US2016/042680, (2nd) International Search Report and Written Opinion, dated Apr. 17, 2017, 13 pages.
PCT/US2016/042680, International Search Report and Written Opinion, dated Jan. 13, 2017, 12 pages.
PCT/US2016/069255, Invitation to Pay Additional Fees, dated Mar. 30, 2017, 2 pages.
PCT/US2016/069255, International Search Report and Written Opinion dated Jun. 1, 2017, 11 pages.
PCT/US2017/044249, International Preliminary Report on Patentability, dated Jan. 29, 2019, 9 pages.
PCT/US2017/044249, Invitation to Pay Additional Fees, dated Sep. 14, 2017, 3 pages.
PCT/US2017/044249, International Search Report and Written Opinion, dated Nov. 21, 2017, 14 pages.
PCT/US2018/014257, International Search Report and Written Opinion, dated May 14, 2018, 13 pages.
PCT/US2018/014257, Invitation to Pay Additional Fees, dated Mar. 22, 2018, 2 pages.
PCT/US2018/050480, Invitation to Pay Additional Fees, dated Nov. 6, 2018, 3 pages.
PCT/US2018/050480, International Search Report and Written Opinion, dated Jan. 29, 2019, 13 pages.
Pelton, J.T. et al., "Somatostatin Analogs with Affinity for Opiate Receptors in Rat Brain Binding Assay", Peptides, 6(Suppl 1): 159-163 (1985).
Piekielna, et al., "Correction for "Synthesis of Mixed Opioid Affinity Cyclic Endomorphin-2 Analogues with Fluorinated Phenylalanines"." ACS Medicinal Chemistry Letters (2016); 7(6): 652-652.
Piekielna, et al., "Synthesis of mixed opioid affinity cyclic endomorphin-2 analogues with fluorinated phenylalanines." ACS Medicinal Chemistry Letters (2015); 6(5): 579-583.
Podwysocka, et al., "TAPP analogs containing β3-homo-amino acids: synthesis and receptor binding." Journal of Peptide Science (2012); 18(9): 556-559.
Preza, G., et al., "Minihepcidins are rationally designed small peptides that mimic hepcidin activity in mice and may be useful for the treatment of iron overload", J Clin Invest (2011); 121(12): 4880-4888.
Ramos, E., et al., "Minihepcidins prevent iron overload in a hepcidin-deficient mouse model of severe hemochromatosis." Blood (Nov. 2012); 120(18): 3829-3836. Epub Sep. 18, 2012.
Rivera, Seth, et al. "Synthetic hepcidin causes rapid dose-dependent hypoferremia and is concentrated in ferroportin-containing organs." Blood (2005); 106.6: 2196-2199.
Sasaki, et al., "D-Arg2-dermorphin tetrapeptide analogs: a potent and long-lasting analgesic activity after subcutaneous administration." Biochem Biophys Res Commun. (1984); 120 (1): 214-218.
Search Report and Written Opinion in Singaporean Application No. 11201609614Q, dated Mar. 12, 2018, 9 pages.
Search Report and Written Opinion in Singaporean Application No. 11201610799W, dated May 31, 2018, 4 pages.
Search Report and Written Opinion in Singaporean Application No. 11201700327W, dated Mar. 16, 2018, 10 pages.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
U.S. Appl. No. 14/050,349, Final Office Action dated Sep. 9, 2015, 17 pages.
U.S. Appl. No. 14/050,349, Non-Final Office Action dated Feb. 27, 2015, 14 pages.
U.S. Appl. No. 14/050,349, Notice of Allowance dated Jan. 12, 2016, 9 pages.
U.S. Appl. No. 14/229,784, Non-Final Office Action dated Aug. 13, 2015, 16 pages.
U.S. Appl. No. 14/229,784, Office Action dated Mar. 8, 2016, 6 pages.
U.S. Appl. No. 14/229,799, Non-Final Office Action dated Jul. 24, 2015, 19 pages.
U.S. Appl. No. 14/229,799, Office Action dated Mar. 4, 2016, 18 pages.
U.S. Appl. No. 14/714,198, Notice of Allowance dated Mar. 17, 2017, 3 pages.
U.S. Appl. No. 14/714,198, Office Action dated Nov. 7, 2016, 6 pages.
U.S. Appl. No. 14/775,469 , Notice of Allowance dated Aug. 10, 2017, 11 pages.
U.S. Appl. No. 14/775,469 , Notice of Allowance dated Sep. 5, 2017, 9 pages.
U.S. Appl. No. 14/775,469 , Office Action dated Apr. 11, 2017, 22 pages.
U.S. Appl. No. 14/800,627, Notice of Allowance dated Feb. 15, 2017, 9 pages.
U.S. Appl. No. 14/800,627, Office Action dated Aug. 25, 2016, 11 pages.
U.S. Appl. No. 14/872,975, Notice of Allowance dated Aug. 16, 2017, 9 pages.
U.S. Appl. No. 14/872,975, Office Action dated Dec. 27, 2016, 14 pages.
U.S. Appl. No. 15/046,325, Office Action dated Aug. 1, 2016, 13 pages.
U.S. Appl. No. 15/442,229, Notice of Allowance dated Sep. 12, 2018, 9 pages.
U.S. Appl. No. 15/442,229, Office Action dated Apr. 20, 2018, 12 pages.
U.S. Appl. No. 15/614,047, Notice of Allowance dated Jun. 7, 2018, 8 pages.
U.S. Appl. No. 15/720,333, Office Action dated Aug. 28, 2018, 24 pages.
U.S. Appl. No. 15/828,214, Notice of Allowance dated Jun. 11, 2018, 9 pages.
U.S. Appl. No. 15/828,214, Office Action dated May 15, 2018, 12 pages.
U.S. Appl. No. 15/831,087, Notice of Allowance dated May 11, 2018, 8 pages.
U.S. Appl. No. 15/831,087, Office Action dated Apr. 12, 2018, 10 pages.
U.S. Appl. No. 15/831,100, Notice of Allowance dated May 8, 2018, 8 pages.
U.S. Appl. No. 15/831,100, Office Action dated Apr. 12, 2018, 11 pages.
U.S. Appl. No. 15/514,983, Office Action dated Nov. 2, 2018, 8 pages.
U.S. Appl. No. 15/836,648, Office Action dated Nov. 6, 2018, 7 pages.

(56) References Cited

OTHER PUBLICATIONS

U.S. Appl. No. 15/514,983, Notice of Allowance dated Jan. 7, 2019, 6 pages.
U.S. Appl. No. 16/128,352, Notice of Allowance dated Feb. 6, 2019, 5 pages.
U.S. Appl. No. 16/128,352, Notice of Allowability dated Feb. 21, 2019, 2 pages.
Waitemata District Health Board, "Crushing Guide for Oral Medication in Residential Aged Care", 2 pages (2011).
Wilczynska, et al., "Synthesis and receptor binding of opioid peptide analogues containing $\beta^3$-homo-amino acids." Journal of Peptide Science (2009); 15(11): 777-782.
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yu and Gallagher, "A Naturally Occurring, Soluble Antagonist of Human IL-23 Inhibits the Development and In Vitro Function of Human Th17 Cells", The Journal of Immunology, 185: 7302-7308 (2010).
Ziora, et al., "Modification of P4 position in β-secretase (BACE1) inhibitors containing phenylnorstatine." Peptide Science (2005); 42: 321-324.
Legge and Morieson, "On the prediction of partition coefficients and $R_F$ values of peptides." Aust. J. Biol. Sci. (1964); 17: 561-571.
Pattarawarapan, "Selective Formation of Homo- and Heterobivalent Peptidomimetics." J. Med. Chem. (Aug. 2003); 46 (17): 3565-3567.
U.S. Appl. No. 15/467,810, Notice of Allowability dated Mar. 13, 2019, 8 pages.
U.S. Appl. No. 16/039,813, Office Action dated Apr. 19, 2019, 11 pages.
U.S. Appl. No. 16/348,293, filed May 8, 2019, Cheng, et al.
U.S. Appl. No. 16/376,565, filed Apr. 5, 2019, Bhandari, et al.
U.S. Appl. No. 16/382,783, filed Apr. 12, 2019, Bhandari, et al.
U.S. Appl. No. 16/439,435, filed Jun. 12, 2019, Bourne, et al.
U.S. Appl. No. 16/478,733, filed Jul. 29, 2019, Bhandari, et al.
Andreu, et al., "Formation of Disulfide Bonds in Synthetic Peptides and Proteins" in Synthetic Peptides and Proteins. In: Pennington M.W., Dunn B.M. (eds) Peptide Synthesis Protocols. Methods in Molecular Biology (1994); 35: 91-169.
Balasubramanian and Kuppuswamy, "RGD-containing Peptides Activate S6K1 through $\beta_3$ Integrin in Adult Cardiac Muscle Cells", J Biol Chem. (Oct. 24, 2003); 278(43): 42214-42224. Epub Aug. 9, 2003.
Davies, J.S., "The Cyclization of Peptides and Depsipeptides", J Pept Sci. (Aug. 2003); 9(8): 471-501.
PCT/US2016/069255, International Preliminary Report on Patentability, dated Jul. 3, 2018, 7 pages.
PCT/US2018/014257, International Preliminary Report on Patentability, dated Jul. 23, 2019, 9 pages.
PCT/US2019/017192, International Search Report and Written Opinion, dated Jun. 11, 2019, 13 pages.
PCT/US2019/017192, Invitation to Pay Additional Fees, dated Apr. 16, 2019, 2 pages.
U.S. Appl. No. 15/698,407, Office Action dated Apr. 25, 2019, 15 pages.
U.S. Appl. No. 16/289,451, Office Action dated Mar. 21, 2019, 21 pages.
U.S. Appl. No. 16/037,982, Office Action dated Mar. 22, 2019, 29 pages.
U.S. Appl. No. 15/698,407, Office Action dated Aug. 5, 2019, 10 pages.
U.S. Appl. No. 16/039,813, Office Action dated Aug. 22, 2019, 11 pages.
U.S. Appl. No. 16/039,813, Notice of Allowance dated Nov. 7, 2019, 10 pages.
U.S. Appl. No. 15/745,371, Office Action dated Dec. 19, 2019, 22 pages.
Yampolsky and Stoltzfus, "The Exchangeability of Amino Acids in Proteins", Genetics (Aug. 2005); 170(4): 1459-1472. Epub Jun. 8, 2005.

* cited by examiner

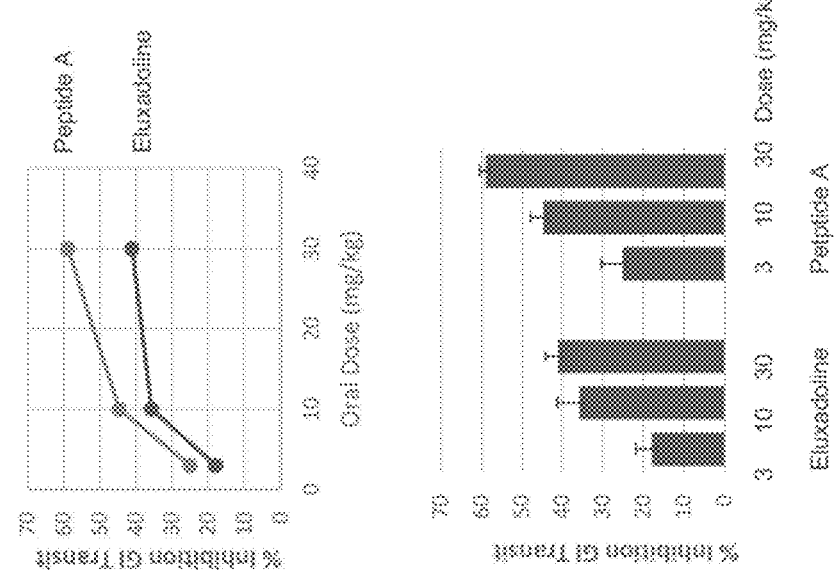
FIG. 1B
FIG. 1C
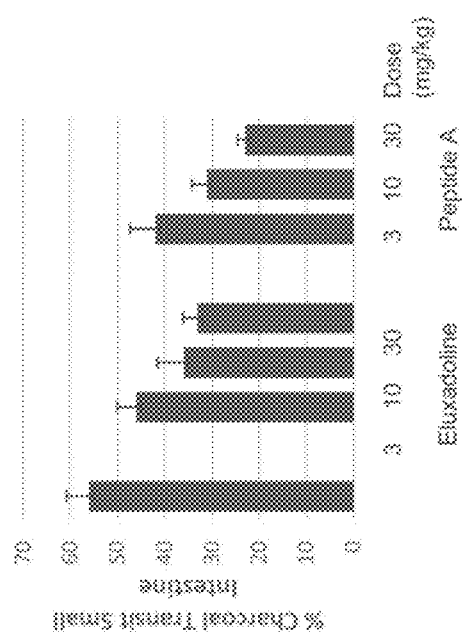
FIG. 1A

FIG. 2A
FIG. 2B
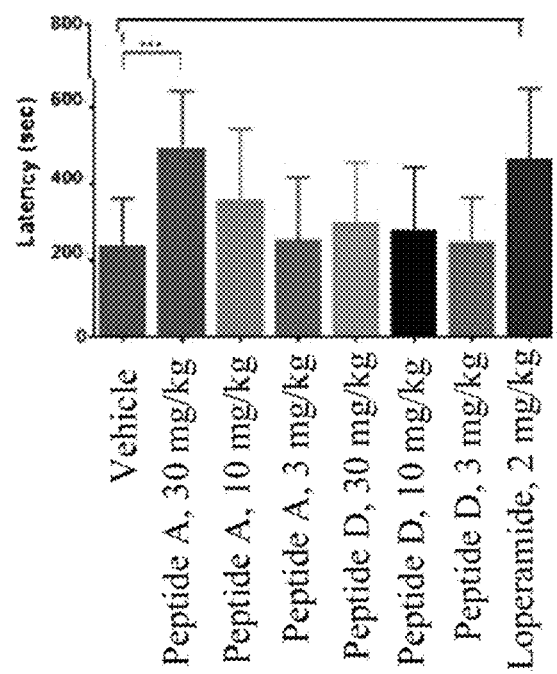
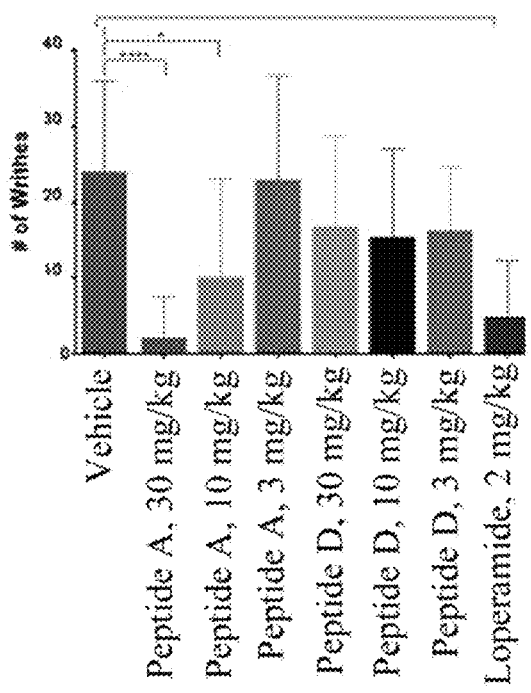

OPIOID AGONIST PEPTIDES AND USES THEREOF

CROSS REFERENCE TO RELATED APPLICATIONS

This application is a Divisional Application of U.S. patent application Ser. No. 16/128,352, filed on Sep. 11, 2018; which claims priority to U.S. Provisional Application No. 62/663,660, filed on Apr. 27, 2018; and U.S. Provisional Application No. 62/556,900, filed on Sep. 11, 2017; all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Mar. 6, 2019, is named PRTH_028_03US_ST25.txt and is 160 KB in size.

BACKGROUND

Irritable bowel syndrome (IBS) is a multifactorial disorder marked by recurrent abdominal pain or discomfort and altered bowel function. It affects between 10 and 20 percent of people in the developed world, about one-third of whom have IBS associated with diarrhea (IBS-D). IBS-D is commonly treated with loperamide, an opioid antidiarrheal agent with no analgesic properties, which inhibits the release of acetylcholine and prostaglandins in the gut, thereby reducing peristalsis and slowing intestinal transit time, which also favorably affects water and electrolyte movement through the bowel. Serotonin (5-HT) also plays an important role in the regulation of GI motility and the activation of 5-HT3 receptors. Alosetron, a 5-HT3 receptor inhibitor, has been used to treat abdominal pain and discomfort associated with IBS. Blockade of 5-HT3 receptors on cholinergic nerve endings also inhibits colonic motility, which can be beneficial for the treatment of IBS-D. However, alosetron is associated with potentially life-threatening ischemic colitis, and its use is limited to women with severe, chronic IBS-D who have failed to respond to conventional treatment.

Clearly, there is a need in the art for alternative treatments for IBS and other inflammatory diseases of the gastrointestinal (GI) tract, including medicaments that reduce associated pain and discomfort and inhibit GI motility.

SUMMARY OF THE INVENTION

In one embodiment, the present disclosure includes an opioid agonist peptide comprising or consisting of an amino acid sequence of Formula I:

(Formula I)
(SEQ ID NO: 339)
Y1-Y2-Y3-X1-X2-X3-X4-X5-Y4-Y5-Y6 or a pharmaceutically acceptable salt or solvate thereof, wherein:
Y1 is absent or any amino acid;
Y2 is absent or any amino acid;
Y3 is absent or any amino acid;
X1 is Tyr, D-Tyr, a Tyr analog, Tic, a Tic analog, or a Phe analog;
X2 is any amino acid;
X3 is any amino acid;
X4 is any amino acid;
X5 is absent or any amino acid;
Y4 is absent or any amino acid;
Y5 is absent or any amino acid; and
Y6 is absent or any amino acid.

In one particular embodiment, X5 is any N-methylamino acid, or X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly.

In one embodiment, the present disclosure provides an opioid agonist peptide comprising or consisting of an amino acid sequence of Formula Ia:

(Formula Ia)
(SEQ ID NO: 357)
X1-X2-X3-X4-X5 or a pharmaceutically acceptable salt or solvate thereof, wherein:
X1 is Tyr, DMT, or Phe(4-COX);
X2 is any amino acid;
X3 is any amino acid;
X4 is Sar, or bhF unsubstituted or substituted with 2-Me, 3-Me, 4-Me, 2-F, 3-F, 4-F, 2-Cl, 3-Cl, 4-Cl, 2-OH, 3-OH, or 4-OH; and
X5 is absent or any amino acid;
wherein DMT is 2,6-dimethyltyrosine;
Phe(4-COX) is substituted or unsubstituted

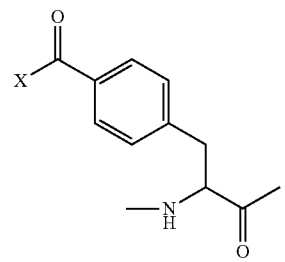

wherein X is substituted or unsubstituted OH or NH$_2$; and provided that when X1 is Tyr; then X4 is bhF unsubstituted or substituted with 2-Me, 3-Me, 4-Me, 2-F, 3-F, 4-F, 2-Cl, 3-Cl, 4-Cl, 2-OH, 3-OH, or 4-OH, and X5 is N-methylamino acid.

In one embodiment, the present disclosure includes an opioid agonist peptide comprising or consisting of an amino acid sequence of Formula IIa, IIb, or IIc:

(Formula IIa)
(SEQ ID NO: 340)
DMT-X2-X3-X4-X5;

(Formula IIb)
(SEQ ID NO: 341)
Phe(4-COX)-X2-X3-X4-X5;
or (Formula IIc)
(SEQ ID NO: 342)
Tyr-X2-X3-X4-X5;

or a pharmaceutically acceptable salt or solvate thereof, wherein DMT is 2,6-dimethyltyrosine; Phe(4-COX) is substituted or unsubstituted

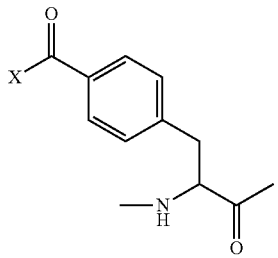

wherein X is substituted or unsubstituted OH or NH$_2$; each of X2 and X3 is independently any amino acid; X4 is substituted or unsubstituted Phe, substituted or unsubstituted bhF or b-homoPhe, or any N-methylamino acid; and X5 is absent, any amino acid or any N-methylamino acid.

In a particular embodiment, X5 is an N-methylamino acid.

In one embodiment, when the peptide is according to Formula IIa, X4 is N-methylamino acid; then X2 is Tic, (D)Tic, Ala, (D)Ala, Asp, (D)Asp, Thr, (D)Thr, Glu, or (D)Glu. In another embodiment, when the peptide is according to Formula IIa, X4 is substituted or unsubstituted Phe; then X5 is N-methylamino acid, or Gly. In another embodiment, when the peptide is according to formula IIc; then X4 is bhF and X5 is N-methylamino acid.

In one embodiment, the present disclosure includes an opioid agonist peptide comprising or consisting of an amino acid sequence of Formula IIIa, IIIb, or IIIc:

```
                                         (SEQ ID NO: 343)
DMT-X2-X3-bhF-X5  (Formula IIIa);

(SEQ ID NO: 344)
Phe(4-COX)-X2-X3-bhF-X5  (Formula IIIb);
or (SEQ ID NO: 345)
Tyr-X2-X3-bhF-X5  (Formula IIIc);
``` or a pharmaceutically acceptable salt or solvate thereof, wherein DMT, Phe(4-COX), bhF, X2, X3, and X5 are as described for Formula IIa-IIc.

In a particular embodiment, the present disclosure includes an opioid agonist peptide comprising or consisting of a sequence set forth in Table 3B, SEQ ID NOs: 1-153, Table 3C, SEQ ID NOs: 154-187 Table 3E, SEQ ID NPs: 188-266, Table 3F, SEQ ID NOs: 267-273, or SEQ ID Nos: 274-336.

In a particular embodiment, the present disclosure includes an opioid agonist peptide comprising or consisting of any of SEQ ID NOs: 1-5 or 7-274. In a particular embodiment, the present disclosure includes an opioid agonist peptide comprising or consisting of any of SEQ ID NOs: 1-5 or 7-336.

In a related embodiment, the present disclosure includes an opioid agonist peptide comprising or consisting of an amino acid sequence of any of Formulas I-XVIIII or SEQ ID NOs: 339-357, or a pharmaceutically acceptable salt or solvate thereof. In a related embodiment, the present disclosure includes an opioid agonist peptide dimer, comprising two peptide monomers, wherein each peptide monomer comprises or consists of an amino acid sequence of any of Formulas I-XVIIII or SEQ ID NOs: 339-357, and wherein the two peptides are connected via a linker moiety, or a pharmaceutically acceptable salt or solvate thereof.

In a further embodiment, the present disclosure provides a pharmaceutical composition comprising an opioid agonist peptide or pharmaceutically acceptable salt or solvate thereof disclosed herein, or an opioid agonist peptide dimer or pharmaceutically acceptable salt or solvate thereof disclosed herein, and a pharmaceutically acceptable diluent, carrier, or excipient.

In another embodiment, the present disclosure provides a method of inhibiting or reducing gastrointestinal motility in a subject in need thereof, comprising providing to the subject an effective amount of a pharmaceutical composition comprising an opioid agonist peptide or pharmaceutically acceptable salt or solvate thereof disclosed herein, or an opioid agonist peptide dimer or pharmaceutically acceptable salt or solvate thereof disclosed herein, and a pharmaceutically acceptable diluent, carrier, or excipient.

In a related embodiment, the present disclosure provides a method of treating or preventing pain or a gastrointestinal disease or condition, comprising providing to a subject in need thereof an effective amount of a pharmaceutical composition comprising an opioid agonist peptide or pharmaceutically acceptable salt or solvate thereof disclosed herein, or an opioid agonist peptide dimer or pharmaceutically acceptable salt or solvate thereof disclosed herein, and a pharmaceutically acceptable diluent, carrier, or excipient.

BRIEF DESCRIPTION OF THE DRAWINGS

FIGS. 1A-1C are graphs demonstrating the ability of an illustrative opioid agonist peptide to inhibit gastrointestinal mobility as compared to eluxadoline when orally administered at the indicated dosages. FIG. 1A provides dose response data generated in a charcoal transit small intestine assay; and FIGS. 1B and 1C provide dose response data generated in an animal model of gastrointestinal transit.

FIGS. 2A-2B provide graphs demonstrating the ability of two illustrative opioid agonist peptides to reduce pain when orally administrated at the indicated dosages. FIG. 2A provides dose response data for the delay in writhing associated with the opioid agonist peptides as compared to loperamide; and FIG. 2B provides dose response data for the total number of writhes as compared to loperamide. ns indicates $p>0.05$, * indicates $p<0.05$,  indicates $p<0.01$, * indicates $p<0.001$, and **** indicates $p<0.0001$.

FIG. 3A provides dose response data for the latency to first writhe associated with the opioid agonist peptides as compared to oral eluxadoline, loperamide, and morphine; and FIG. 3B provides dose response data for the total number of writhes in a ten minute session as compared to oral eluxadoline, loperamide, and morphine. ns indicates $p>0.05$, * indicates $p<0.05$,  indicates $p<0.01$, * indicates $p<0.001$, and **** indicates $p<0.0001$.

DETAILED DESCRIPTION

Figure 3A:
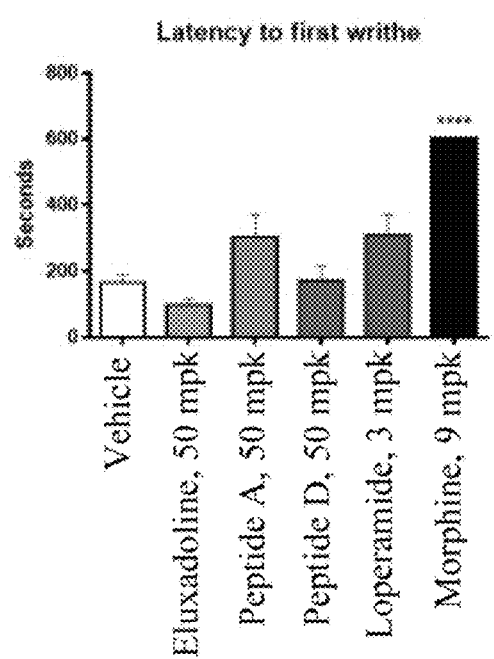
FIGS. 3A-3B provide graphs demonstrating the ability of two illustrative opioid agonist peptides to reduce pain when orally administrated at the indicated dosages.

The present invention provides novel opioid agonist peptides, including but not limited to peptide monomers and peptide dimers, capable of agonizing one or both of the mu opioid receptor (MOR) or delta opioid receptor (DOR). Opioid agonist peptides disclosed herein are stable under gastrointestinal conditions, and they inhibit gastrointestinal motility. Accordingly, they may be administered orally to subjects, e.g., to treat or prevent gastrointestinal or inflammatory diseases, including but not limited to, irritable bowel syndrome (IBS), IBS with diarrhea (IBS-D), inflammatory bowel disease (IBD), ulcerative colitis, Crohn's disease and Celiac disease.

Definitions

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, non-human primates, livestock animals (e.g., bovines, porcines), companion animals (e.g., canines, felines) and rodents (e.g., mice and rats).

The term "peptide," as used herein, refers broadly to a sequence of two or more amino acids joined together by peptide bonds. It should be understood that this term does not indicate a specific length of a polymer of amino acids, nor is it intended to imply or distinguish whether the polypeptide is produced using recombinant techniques, chemical or enzymatic synthesis, or is naturally occurring.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. One example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|---|---|---|---|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|---|---|---|---|---|
| A | E | H | M | F |
| L | D | R | S | Y |
| I |   | K | T | W |
| P |   |   | C |   |
| G |   |   | N |   |
| V |   |   | Q |   |

The term "amino acid" or "any amino acid" as used here refers to any and all amino acids, including naturally occurring amino acids (e.g., a-amino acids or α-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic acids (i.e., those not naturally encoded or found in the genetic code) that either occur naturally or are chemically synthesized. Over 140 unnatural amino acids are known and thousands of more combinations are possible. Examples of "unnatural" amino acids include β-amino acids ($β^3$ and $β^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid. According to certain embodiments, a peptide inhibitor comprises an intramolecular bond between two amino acid residues present in the peptide inhibitor. It is understood that the amino acid residues that form the bond will be altered somewhat when bonded to each other as compared to when not bonded to each other. Reference to a particular amino acid is meant to encompass that amino acid in both its unbonded and bonded state, e.g., before and after cross-link formation.

For the most part, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of Non-Natural Amino Acids and Chemical Moieties (for amino acid derivatives, all L unless stated)

| Abbreviation | Definition |
|---|---|
| Ac— | Acetyl |
| Hy | Hydrogen (Free N-terminal) |
| Dap or Dapa | L-Diaminopropionic acid |
| Dab or Daba | L-Diaminobutyric acid |
| Aba | L-aminobutyric acid |
| DIG | Diglycolic acid |
| Orn | L-Ornathine |
| Pen | L-Penicillamine |
| Sarc or Sar | Sarcosine |
| Phe-(4-Guanidino) | 4-Guanidine-L-Phenylalanine |
| N(Me)Arg or N(Me)R | N-Methyl-L-Arginine |
| N(Me)Trp | N-Methyl-L-Tryptophan |
| N(Me)Gln | N-Methyl-L-Glutamine |
| N(Me)Ala or N(Me)Ala | N-Methyl-L-Alanine |
| N(Me)a or N(Me)-a | N-Methyl-D-Alanine |
| N(Me)bAla | N-Methyl-beta-Alanine |
| N(Me)Lys or N(Me)K | N-Methyl-Lysine |
| N(Me)Asn | N-Methyl-L-Asparagine |
| N(Me)Nle | N-Methyl-L-Norleucine |
| N(Me)F or N(Me)Phe | N-Methyl-L-phenylalanine |
| 6-ChloroTrp | 6-Chloro-L-Tryptophan |
| 5-HydroxyTrp or Trp(5-OH) | 5-Hydroxy-L-Tryptophan |
| Phe(4-OMe) or Y(OMe) | 4-Methoxy-L-phenylalanine |
| Bip | L-4,4'-Biphenylalanine |
| β-Ala | beta-Alanine |
| β-hTyr | beta homo-L-Tyrosine |
| hTyr or hY | homo-L-Tyrosine |
| hy | homo-D-Tyrosine |
| y or (D)Tyr | D-Tyrosine |
| meta-Tyr or Phe(3-OH) | 3-Hydroxy-L-Phenylalanine |
| β-hTrp | beta homo-L-Trptophan |
| β-hAla | beta homo-L-Alanine |
| β-hLeu | beta homo-L-Leucine |
| β-hVal | beta homo-L-Valine |
| Tic | (3S)-1,2,3,4-Tetrahydroisoquinoline-7-hydroxy-3-carboxylic Acid |
| dTic or (D)Tic | (3R)-1,2,3,4-Tetrahydroisoquinoline-7-hydroxy-3-carboxylic Acid |
| Phe(4-OMe) | 4-methoxy-L-phenylalanine |
| N(Me)-Lys | N-Methyl-L-Lysine |
| N(Me)-Lys(Ac) | N-ε-Acetyl-D-lysine |
| $CONH_2$ | Carboxamide |
| N(trifluoroethyl)Gly | N(trifluoroethyl)Glycine |
| N(cyclohexyl)Gly | N(cyclohexyl)Glycine |
| N(amyl)Gly | N(amyl)Glycine |
| N(hexadecyl)Gly | N(hexadecyl)Glycine |
| N(3-isopropyloxypropyl)Gly | N(3-isopropyloxypropyl) Glycine |
| N(benzyl)Gly | N(benzyl)Glycine |
| N(Me)Phg | N(Methyl)Phenylglycine |
| N(cyclohexylmethyl)Gly | N(cyclohexylmethyl)Glycine |
| N(3-propanoic acid)Gly | N(3-propanoic acid)Glycine |
| N(phenethyl)Gly | N(phenethyl)Glycine |
| 2-Nal | 2-Nathyl Alanine |
| N(Octyl)Gly | N(Octyl)Glycine |
| N(isopentyl)Gly | N(isopentyl)Glycine |
| COOH | Carboxylic Acid |
| Phe(4-F) or F(4-F) | 4-Fluoro-L-Phenylalanine |
| DMT | 2,6-DimethylTyrosine |
| Phe(4-OMe) | 4-Methoxyphenylalanine |
| hLeu | L-homoLeucine |

TABLE 1-continued

Abbreviations of Non-Natural Amino Acids and Chemical Moieties (for amino acid derivatives, all L unless stated)

| Abbreviation | Definition |
|---|---|
| hArg | L-homoArginine |
| α-MeLys | alpha-methyl-L-Lysine |
| α-MeOrn | alpha-methyl-L-Ornathine |
| α-MeLeu | alpha-methyl-L-Leucine |
| α-MeTrp | alpha-methyl-L-Tryptophan |
| α-MePhe | alpha-methyl-L-Phenylalanine |
| α-MeTyr | alpha-methyl-L-Tyrosine |
| α-DiethylGly | α-DiethylGlycine |
| Lys(Ac) | N-ε-acetyl-L-Lysine |
| DTT | Dithiothreotol |
| Nle | L-Norleucine |
| βhPhe or b-homoPhe, or b-hPhe or bhF | L-β-homophenylalanine |
| βhPro | L-β-homoproline |
| Phe(4-$CF_3$) | 4-Trifluoromethyl-L-Phenylalanine |
| β-Glu | L-β-Glutamic acid |
| βhGlu | L-β-homoglutamic acid |
| Gla | Gama-Carboxy-L-Glutamic acid |
| Phe(4-Phenoxy) | 4-Phenoxy-L-phenylalanine |
| Phe(4-OBzl) | O-Benzyl-L-tyrosine |
| Phe(4-$CONH_2$) | 4-Carbamoyl-L-phenylalanine |
| Phe(4-$CO_2H$) | 4-Carboxy-L-phenylalanine |
| Phe(3,4-dichloro) or Phe(3,4-diCl) | 3,4 dichloro-L-phenylalanine |
| Tyr(3-t-Bu) | 3-t-butyl-L-tyrosine |
| Phe(4-t-Bu) | 4-t-butyl-L-phenylalanine |
| Phe[4-(2-aminoethoxy)] | 4-(2-aminoethoxy)-L-phenylalanine |
| (aMe)Phe or (α-Me)Phe | Alpha-methyl-phenylalanine |
| Phe(4-CN) | 4-cyano-L-phenylalanine |
| Phe(4-Br) | 4-bromo-L-phenylalanine |
| Phe(4-$NH_2$) | 4-amino-L-phenylalanine |
| Phe(4-$NHCOCH_3$) or Phe(4-acetamide) | 4-acetylamino-L-phenylalanine |
| Phe(4-Me) or F(4-Me) | 4-methyl-L-phenylalanine |
| Phe(3,4-dimethoxy) or Phe(3,4-diOMe) | 3,4-dimethoxy-L-phenylalanine |
| hPhe(3,4-dimethoxy) or hPhe(3,4-diOMe) | 3,4-dimethoxy-L-homophenylalanine |
| Phe(2,4-dimethyl) | 2,4-dimethyl-L-phenylalanine |
| Phe(3,5-difluoro) | 3,5-difluoro-L-phenylalanine |
| Phe(pentafluoro) | pentafluoro-L-phenylalanine |
| 2,5,7-tert butyl Trp | 2,5,7-Tri-tert-butyl-L-tryptophan |
| Tic | L-1,2,3,4,-tetrahydro-isoquinoline-3-carboxylic acid |

TABLE 1-continued

Abbreviations of Non-Natural Amino Acids and
Chemical Moieties (for amino acid derivatives, all L unless stated)

| Abbreviation | Definition |
| --- | --- |
| Tic(7-OH) | [structure: 7-hydroxy-1,2,3,4-tetrahydroisoquinoline-3-carboxylic acid] |
| Phe(4-OAllyl) | 4-(O-Allyl)-L-phenylalanine |
| Phe(4-N$_3$) | 4-azidophenylalanine |
| DMP(4-CONH$_2$) or Phe(DMC) | Phe(2,6-dimethyl-4-CONH$_2$) |
| DMT | L-2,6-Dimethyl-tyrosine |
| β-homoPhe(2-Me) | (S)-3-Amino-4-(2-methyl-phenyl)-butyric acid |
| β-homoPhe(3-Me) | (S)-3-Amino-4-(3-methyl-phenyl)-butyric acid |
| β-homoPhe(4-Me) | (S)-3-Amino-4-(4-methyl-phenyl)-butyric acid |
| β-homoPhe(2-F) | (S)-3-Amino-4-(2-fluoro-phenyl)-butyric acid |
| β-homoPhe(3-F) | (S)-3-Amino-4-(3-fluoro-phenyl)-butyric acid |
| β-homoPhe(4-F) | (S)-3-Amino-4-(4-fluoro-phenyl)-butyric acid |
| β-homoPhe(4-NO$_2$) | (S)-3-Amino-4-(4-nitro-phenyl)-butyric acid |
| β-homoPhe(4-OH) | L-β-homotryrosine |
| β-homoTrp | L-β-homotryptophane |
| β-homoPhe(2-Br) | (S)-3-Amino-4-(2-bromo-phenyl)-butyric acid |
| β-homoPhe(3-Br) | (S)-3-Amino-4-(3-bromo-phenyl)-butyric acid |
| β-homoPhe(4-Br) | (S)-3-Amino-4-(4-bromo-phenyl)-butyric acid |
| β-homoPhe(3-Cl) | (S)-3-Amino-4-(3-chloro-phenyl)-butyric acid |
| β-homoPhe(4-I) | (S)-3-Amino-4-(4-iodo-phenyl)-butyric acid |
| DPA | 3,3-diphenyl-L-alanine |

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). Unless otherwise indicated, three-letter and single-letter abbreviations of amino acids refer to the L-isomeric form of the amino acid in question. The term "L-amino acid," as used herein, refers to the "L" isomeric form of a peptide, and conversely the term "D-amino acid" refers to the "D" isomeric form of a peptide (e.g., (D)Asp or (D)Phe). Amino acid residues in the D isomeric form can be substituted for any L-amino acid residue, as long as the desired function is retained by the peptide. D-amino acids may be indicated as customary in lower case when referred to using single-letter abbreviations.

In the case of less common or non-naturally occurring amino acids, unless they are referred to by their full name (e.g. sarcosine, ornithine, etc.), frequently employed three- or four-character codes are employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), β-Pro (pyrrolidine-3-carboxylic acid), and 8Ado (8-amino-3,6-dioxaoctanoic acid), Abu (2-amino butyric acid), βhPro (β-homoproline), βhPhe (β-homophenylalanine) and Bip (β,β diphenylalanine), and Ida (Iminodiacetic acid).

As is clear to the skilled artisan, the peptide sequences disclosed herein are shown proceeding from left to right, with the left end of the sequence being the N-terminus of the peptide and the right end of the sequence being the C-terminus of the peptide. Peptides may include an N-terminal free amine group (NH$_2$) and/or a C-terminal free carboxyl group (COOH). In particular embodiments of any of the peptides disclosed herein, the peptides include an N-terminal free amine group. Peptides may be modified, e.g., by attachment of small chemical groups such as acetyl, propionyl and methyl, and the addition of membrane anchors, such as palmitoyl and myristoyl groups or any fatty acid groups. In addition, peptides may be modified in other manners, including but not limited to, myristoylation and acylation, e.g., palmitoylation. In certain embodiments, peptides are modified at an internal amino acid residue, e.g., a small chemical group or membrane anchor may be attached to the side chain of an internal amino acid. In certain embodiments, the C-terminus of a peptide may also be modified, including but not limited to C-terminal amidation. Where a peptide sequence is disclosed herein, without specifying the structure of its N-terminus and/or C-terminus, it is understood to allow the presence of any possible N-terminal and/or C-terminal structures and any possible modification, e.g., an attachment to an internal amino acid side chain. For example, for the peptide: Tyr-((D)Ala)-Gly-(β-homoPhe)-Sar (SEQ ID NO:62) it is understood that the N-terminal Tyr may comprise an N-terminal free amine group. Similarly, it is understood that the C-terminal Sar may comprise a C-terminal free carboxyl group, or it may be modified in any manner, e.g., amidated to comprise a C-terminal NH$_2$ group. Among sequences disclosed herein are sequences incorporating an "—OH" moiety or an "—NH$_2$" moiety at the carboxy terminus (C-terminus) of the sequence. In such cases, and unless otherwise indicated, a "H—" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the invention, a C-terminal "—OH" moiety may be substituted for a C-terminal "—NH$_2$" moiety, and vice-versa.

The term "dimer," as used herein, refers broadly to a peptide comprising two monomer subunits. Dimers of the present invention include homodimers and heterodimers. A monomer subunit of a dimer may be linked at its C- or N-terminus, or it may be linked via internal amino acid residues. Each monomer subunit of a dimer may be linked through the same site, or each may be linked through a different site (e.g., C-terminus, N-terminus, or internal site).

The term "NH$_2$," as used herein, can refer to a free amino group present at the amino terminus of a polypeptide. The term "OH," as used herein, can refer to a free carboxy group present at the carboxy terminus of a peptide. Further, the term "Ac," as used herein, refers to Acetyl protection through acylation of the C- or N-terminus of a polypeptide. In certain peptides shown herein, the NH$_2$ locates at the C-terminus of the peptide indicates an amino group.

The term "carboxy," as used herein, refers to —CO$_2$H.

The term "isostere replacement," as used herein, refers to any amino acid or other analog moiety having chemical and/or structural properties similar to a specified amino acid.

In certain embodiments, an isostere replacement is a conservative substitution of an amino acid.

The term "linker" or "linker moiety," as used herein, refers broadly to a chemical structure that is capable of linking or joining together two peptide monomer subunits to form a dimer.

The term "pharmaceutically acceptable salt," as used herein, represents salts or zwitterionic forms of the peptides or compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemi salts of acids and bases may also be formed, e.g., hemisulphate and hemicalcium salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

As used herein, an "effective amount" or a "therapeutically effective amount" of the opioid agonist peptide of the invention is meant to describe a sufficient amount of the opioid agonist peptide to achieve a desired effect, including but not limited to a reduction or inhibition of pain or gastrointestinal motility, or the treatment or prevention of any of the diseases and disorders described herein. In particular embodiments, the therapeutically effective amount will achieve a desired benefit/risk ratio applicable to any medical treatment.

An "analog" of an amino acid, e.g., a "Phe analog" or a "Tyr analog" means an analog of the referenced amino acid. A variety of amino acid analogs are known and available in the art, including Phe and Tyr analogs. In certain embodiments, an amino acid analog, e.g., a Phe analog or a Tyr analog comprises one, two, three, four or five substitutions as compared to Phe or Tyr, respectively. In certain embodiments, the substitutions are present in the side chains of the amino acids. In certain embodiments, a Phe analog has the structure Phe($R^2$), wherein $R^2$ is a H, OH, $CH_3$, $CO_2H$, $CONH_2$, $CONH_2OCH_2CH_2NH_2$, t-Bu, $OCH_2CH_2NH_2$, phenoxy, $OCH_3$, OAllyl, Br, Cl, F, $NH_2$, N3, or guanadino. In certain embodiments, $R^2$ is $CONH_2OCH_2CH_2NH_2$, $OCH_3$, $CONH_2$, $OCH_3$ or $CO_2H$. Examples of Phe analogs include, but are not limited to: hPhe, Phe(4-OMe), α-Me-Phe, hPhe(3,4-dimethoxy), Phe(4-$CONH_2$), Phe(4-phenoxy), Phe(4-guanadino), Phe(4-tBu), Phe(4-CN), Phe(4-Br), Phe(4-OBzl), Phe(4-$NH_2$), βhPhe(4-F), Phe(4-F), Phe(3,5-difluoro), Phe(4-$CH_2CO_2H$), Phe(penta-F), Phe(3,4-dichloro), Phe (3,4-difluoro), Phe(4-$CF_3$), β-diPheAla, Phe(4-$N_3$), Phe[4-(2-aminoethoxy)], 4-Phenylbenzylalanine, Phe(4-$CONH_2$), Phe(3,4-dimethoxy), Phe(4-$CF_3$), Phe(2,3-dichloro), and Phe(2,3-difluoro). Examples of Tyr analogs include, but are not limited to: hTyr, N(Me)-Tyr, Tyr(3-tBu), Tyr(4-$N_3$), DMT, αMeTyr and βhTyr.

Opioid Agonist Peptides

The present invention provides opioid agonist peptides. In one embodiments, opioid agonist peptides comprise or consist of an amino acid sequence of Formula I:

(SEQ ID NO: 339)
Y1-Y2-Y3-X1-X2-X3-X4-X5-Y4-Y5-Y6 (Formula I)

or a pharmaceutically acceptable salt or solvate thereof, wherein:
Y1 is absent or any amino acid;
Y2 is absent or any amino acid;
Y3 is absent or any amino acid;
X1 is Tyr, D-Tyr, a Tyr analog, Tic, a Tic analog, or a Phe analog;
X2 is any amino acid;
X3 is any amino acid;
X4 is any amino acid;
X5 is absent or X5 is any amino acid;

Y4 is absent or any amino acid;
Y5 is absent or any amino acid; and
Y6 is absent or any amino acid.

In one embodiment, X5 is absent. In another embodiment, X5 is any amino acid. In another embodiment, X5 is a hydrophobic amino acid. In yet another embodiment, X5 is any N-methylamino acid. In certain embodiments, X5 is absent, any N-methylamino acid, or X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly. In certain embodiments, X5 is absent, a hydrophobic amino acid, or an amino acid selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly. In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly. In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, and N(Me)Nva.

In certain embodiment, X5 is N(Me)Trp.

In one embodiment, Tyr analog is DMT. In another embodiment, Phe analog is Phe(2,6-dimethyl-4-CONH$_2$).

In particular embodiments of opioid agonist peptide or pharmaceutically acceptable salt or solvate thereof of Formula I:
X1 is Tyr, DMT, β-homo-Tyr, N(Me)-Tyr, Tyr(3-tBu), (D)Tyr, homo-Tyr, Tyr(3-Cl), meta-Tyr, Tyr(3-F), Tyr(3-OH), Phe(4-NHCOCH$_3$), Phe(4-CONH$_2$), Tic, Phe(2,6-dimethyl-4-CONH$_2$), Phe {4-(2-aminoethoxy)}, Phe(4-COOH), Phe(2,6-dimethyl)(4-tetrazole), Phe(2,6-dimethyl)(4-imidazole), or Phe(2,6-dimethyl)(4-triazole).

In particular embodiments of opioid agonist peptide or pharmaceutically acceptable salt or solvate thereof of Formula I:
X2 is (D)Arg, (D)N(Me)-Ala, (D)Ala, (D)Tic, (D)Lys, (D)Orn, (D)Thr, (D)Asp, or (D)Tyr.

In certain embodiments of an opioid agonist peptide or pharmaceutically acceptable salt or solvate thereof of Formula I: X3 is (D)Phe, Phe, Bip, His, Aba, Trp, β-homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or β-Ala.

In certain embodiments of an opioid agonist peptide or pharmaceutically acceptable salt or solvate thereof of Formula I:
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, a substituted β-homoPhe, N(Octyl)Gly, Leu, Val, Nle, DPA, Trp, Phe, Phe(4-CN), Tic, or a substituted aromatic amino acid (optionally, Phe(3,4-dichloro), β-homoPhe (2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO$_2$), (D)N(Me)-Phe, or β-homoTrp, or an amino acid having one of the following structures:

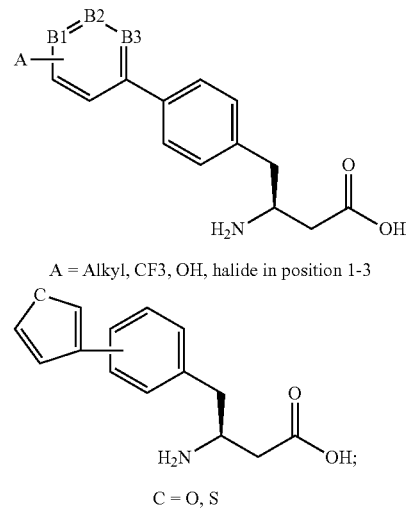

A = Alkyl, CF3, OH, halide in position 1-3

C = O, S wherein each B1, B2, and B3 is independently CH or N.

In certain embodiments of an opioid agonist peptide or pharmaceutically acceptable salt or solvate thereof of Formula I:
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, a substituted β-homoPhe, N(Octyl)Gly, Leu, Val, Nle, DPA, Trp, Phe, Phe(4-CN), Tic, or a substituted aromatic amino acid (optionally, Phe(3,4-dichloro), β-homoPhe (2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO$_2$), (D)N(Me)-Phe, or β-homoTrp).

In certain embodiments of an opioid agonist peptide or pharmaceutically acceptable salt or solvate thereof of Formula I:
X4 is β-homoPhe or a substituted aromatic amino acid (optionally, Phe(3,4-dichloro), β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO$_2$), (D)N(Me)-Phe, or β-homoTrp, or an amino acid having one of the following structures:

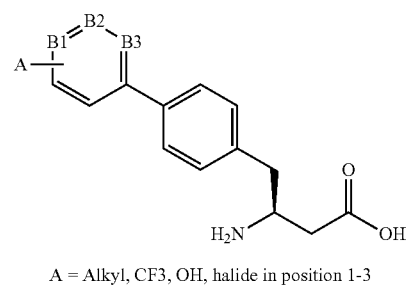

A = Alkyl, CF3, OH, halide in position 1-3

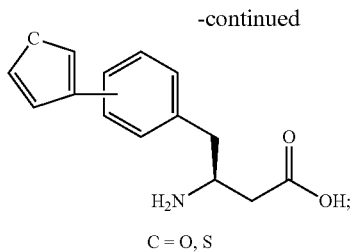

C = O, S wherein each B1, B2, and B3 is independently CH or N.

In particular embodiments of an opioid agonist peptide or pharmaceutically acceptable salt or solvate thereof of Formula I:

X5 is a hydrophobic amino acid, or X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In particular embodiments of an opioid agonist peptide or pharmaceutically acceptable salt or solvate thereof of Formula I:

X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In particular embodiments of an opioid agonist peptide or pharmaceutically acceptable salt or solvate thereof of Formula I:

X5 is not Leu, Met, or (D)Leu.

In certain embodiments of an opioid agonist peptide or pharmaceutically acceptable salt or solvate thereof of Formula I:

X1 is Tyr, (D)Tyr, a Tyr analog, a Phe analog, Tic, or a Tic analog;
X2 is a (D) amino acid;
X3 is any amino acid; and
X4 is β-homoPhe or a substituted aromatic amino acid (optionally, Phe(3,4-dichloro), β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp); and
X5 is absent, a hydrophobic amino acid, or selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, and (D)Leu.

In certain embodiments of an opioid agonist peptide or pharmaceutically acceptable salt or solvate thereof of Formula I:

X1 is Tyr, DMT, β-homo-Tyr, N(Me)-Tyr, Tyr(3-tBu), homo-Tyr, Tyr(3-Cl), Tyr(3-F), Tyr(3-OH), Phe(4-NHCOCH₃), Phe(4-CONH₂), Tic, Phe(2,6-dimethyl-4-CONH₂), Phe(4-(2-aminoethoxy)), Phe(2,6-dimethyl-4-CONH₂) or Phe(4-COOH);
X2 is (D)Arg, N(Me)-(D)Ala, (D)Ala, (D)Tic, (D)Lys, (D)Orn, (D)Thr, (D)Asp, or (D)Tyr;
X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or β-Ala;
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, N(Octyl)Gly, Leu, Val, Nle, DPA, Trp, Phe, Phe(4-CN), Tic, Phe(3,4-dichloro), or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp); and
X5 is absent, a hydrophobic amino acid, or selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In particular embodiments of an opioid agonist peptide or pharmaceutically acceptable salt or solvate thereof of Formula I:

X1 is Tyr, DMT, or Phe(2,6-dimethyl-4-CONH₂);
X2 is a (D) amino acid;
X3 is Gly or β-Ala;
X4 is β-homoPhe or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp); and
X5 is absent, a hydrophobic amino acid, or selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu. In certain embodiments, X4 is β-homoPhe.

In certain embodiments of an opioid agonist peptide or pharmaceutically acceptable salt or solvate thereof of Formula I:

X1 is Tyr, DMT, or Phe(2,6-dimethyl-4-CONH₂);
X2 is (D)Arg, (D)Ala, or (D)Tic;
X3 is Gly, Phe, a Phe analog, Aba, Trp, 1-Nal, Bip, Ala, Leu, or Ile;
X4 is β-homoPhe or a Phe analog (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), or (D)N(Me)-Phe); and X5 is absent, a hydrophobic amino acid, or selected from Sar, Gly, Aib, β-Ala, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In certain embodiments of an opioid agonist peptide or pharmaceutically acceptable salt or solvate thereof of Formula I:

X5 is Sar, NMe-Leu, NMe-Ala, NMe-Val, NMe-Cha, NMe-Phg, NMe-Phe, NMe-Nle, N(Me)Ile, N(Me)Tyr, N(Me)Cha, N(Me)Phg, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, or N(isopentyl)Gly.

In certain embodiments of an opioid agonist peptide of pharmaceutically acceptable salt or solvate thereof of Formula I, Y1, Y2, Y3, Y4, Y5, and Y6 are all absent, and the peptide comprises or consists of an amino acid sequence of Formula Ia:

X1-X2-X3-X4-X5 (Formula Ia) (SEQ ID NO: 357)

wherein:
X1 is Tyr, DMT, or Phe(4-COX);
X2 is any amino acid;
X3 is any amino acid;
X4 is Sar, or bhF substituted or unsubstituted with 2-Me, 3-Me, 4-Me, 2-F, 3-F, 4-F, 2-Cl, 3-Cl, 4-Cl, 2-OH, 3-OH, or 4-OH; and
X5 is absent or any amino acid.

In certain embodiments of an opioid agonist peptide or pharmaceutically acceptable salt or solvate thereof of Formula I-Ia, IIa-IIc, IIIa-IIIc, IVa-IVc, Va-Vd, VIa-VId, VIIa-VIId, VIIIa-VIIIl (I-VIIIl), the opioid agonist peptide comprises a C-terminal OH or NH$_2$.

In certain embodiments of the opioid agonist peptide or pharmaceutically acceptable salt or solvate thereof of Formula I-XVIIIl, the opioid agonist peptide comprises or consists of any of the following amino acid sequences:

DMT-r-F-K; (SEQ ID NO: 7)

DMT-r-N(Me)F-K; (SEQ ID NO: 274)

DMT-r-f-K; (SEQ ID NO: 1)

DMT-r-bhF-K; (SEQ ID NO: 275)

DMT-r-Y(O-Me)-K; (SEQ ID NO: 276)

DMT-r-F(4-Me)-K; (SEQ ID NO: 277)

DMT-r-F(4-F)-K; (SEQ ID NO: 278)

DMT-r-F-k; (SEQ ID NO: 2)

DMT-r-W-K; (SEQ ID NO: 279)

DMT-r-Bip-K; (SEQ ID NO: 3)

DMT-r-1-Nal-K; (SEQ ID NO: 280)

DMT-r-2-Nal-K; (SEQ ID NO: 281)

DMT-r-H-K; (SEQ ID NO: 4)

DMT-r-F-N(Me)K; (SEQ ID NO: 5)

Y-r-F-K; (SEQ ID NO: 282)

DMT-r-F-K; (SEQ ID NO: 7)

Y-r-F-(Me)bAla; (SEQ ID NO: 283)

Y-r-F-K(Ac); (SEQ ID NO: 7)

DMT-N(Me)a-Aba-G; (SEQ ID NO: 8)

DMT-r-f-k; (SEQ ID NO: 284)

DMT-r-F-(Me)bAla; (SEQ ID NO: 285)

DMT-r-F-Sar; (SEQ ID NO: 9)

DMT-N(Me)a-F-Sar; (SEQ ID NO: 10)

DMT-r-F-(Me)bAla; (SEQ ID NO: 285)

DMT-r-W-(Me)bAla; (SEQ ID NO: 11)

DMT-r-bhF-(Me)bAla; (SEQ ID NO: 12)

DMT-r-1-Nal-(Me)bAla; (SEQ ID NO: 13)

y-r-f-k; (SEQ ID NO: 286)

Y-r-F-k; (SEQ ID NO: 287)

K(Ac)-Y-r-F-K; (SEQ ID NO: 288)

K(Ac)-Y-r-F-K; (SEQ ID NO: 288)

y-r-F-K; (SEQ ID NO: 289)

k-DMT-r-1-Nal-(Me)bAla; (SEQ ID NO: 290)

Y-r-F-r; (SEQ ID NO: 291)

-continued

Y-r-F-N(Me)R; (SEQ ID NO: 292)

Y-r-Y-r; (SEQ ID NO: 293)

Y-r-y-r; (SEQ ID NO: 294)

DMT-N(Me)a-F-Sar; (SEQ ID NO: 10)

Y-N(Me)R-F-N(Me)K; (SEQ ID NO: 295)

Y-N(Me)R-F-K; (SEQ ID NO: 296)

Y-D-Nva-F-Orn; (SEQ ID NO: 297)

Y-D-Nle-F-Orn; (SEQ ID NO: 298)

Y-D-Orn-F-D; (SEQ ID NO: 299)

hY-r-bhF-k; (SEQ ID NO: 300)

hY-r-F-K; (SEQ ID NO: 301)

hY-r-F-N(Me)K; (SEQ ID NO: 302)

N(Me)Y-r-F-N(Me)K; (SEQ ID NO: 303)

hY-r-F-k; (SEQ ID NO: 304)

DMT-r-F-D-N(Me)Phe; (SEQ ID NO: 14)

DMT-r-F-(aMe)Phe; (SEQ ID NO: 15)

DMT-r-F-Phe(4-F); (SEQ ID NO: 16)

DMT-r-F-hPhe; (SEQ ID NO: 18)

DMT-r-Phe(4-F)-Sar; (SEQ ID NO: 19)

DMT-r-Phe(4-CN)-Sar; (SEQ ID NO: 20)

DMT-r-Tic-Sar; (SEQ ID NO: 21)

DMT-r-Phe(3,4-dichloro)-Sar; (SEQ ID NO: 22)

DMT-r-BIP-Sar; (SEQ ID NO: 23)

DMT-r-tBu-Phe-Sar; (SEQ ID NO: 24)

DMT-r-Phe(3,4-dimethoxy)-Sar; (SEQ ID NO: 25)

DMT-r-DPA-Sar; (SEQ ID NO: 26)

DMT-r-F-N(Octyl)Gly; (SEQ ID NO: 27)

DMT-r-F-nLeu; (SEQ ID NO: 28)

DMT-r-F-L; (SEQ ID NO: 29)

DMT-r-F-V; (SEQ ID NO: 30)

DMT-r-W-nLeu; (SEQ ID NO: 31)

DMT-r-DPA-Sar; (SEQ ID NO: 32)

DMT-r-G-DPA; (SEQ ID NO: 33)

DMT-r-G-W; (SEQ ID NO: 34)

DMT-r-Sar-W; (SEQ ID NO: 35)

DMT-r-F-DPA; (SEQ ID NO: 36)

DMT-a-G-F-nLeu; (SEQ ID NO: 37)

DMT-a-G-Phe(4-F)-G; (SEQ ID NO: 38)

DMT-a-G-Phe(4-CN)-G; (SEQ ID NO: 39)

DMT-a-G-Tic-G; (SEQ ID NO: 40)

DMT-a-G-Phe(3,4-dichloro)-G; (SEQ ID NO: 41)

DMT-r-F-N-MePhe; (SEQ ID NO: 305)

DMT-a-F-Sar; (SEQ ID NO: 306)

DMT-P-F-Sar; (SEQ ID NO: 307)

DMT-dP-F-Sar; (SEQ ID NO: 308)

DMT-Tic-F-Sar; (SEQ ID NO: 309)

DMT-a-G-F-Sar; (SEQ ID NO: 42)

DMT-dP-G-F-Sar; (SEQ ID NO: 310)

DMT-Tic-G-F-Sar; (SEQ ID NO: 311)

DMT-a-bhF-Sar; (SEQ ID NO: 312)

DMT-Tic-bhF-Sar; (SEQ ID NO: 313)

DMT-a-G-bhF-Sar; (SEQ ID NO: 43)

DMT-Tic-G-bhF-Sar; (SEQ ID NO: 314)

DMT-dTic-F-Sar; (SEQ ID NO: 44)

-continued

DMT-dTic-G-F-Sar; (SEQ ID NO: 45)

DMT-a-hF-Sar; (SEQ ID NO: 46)

DMT-a-G-hF-Sar; (SEQ ID NO: 47)

DMT-a-hF-nL; (SEQ ID NO: 48)

DMT-a-G-hF-nL; (SEQ ID NO: 49)

bH-Tyr-a-G-bhF-Sar; (SEQ ID NO: 50)

N(Me)Y-a-G-bhF-Sar; (SEQ ID NO: 51)

Tyr(3-tBu)-a-G-bhF-Sar; (SEQ ID NO: 52)

y-a-G-bhF-Sar; (SEQ ID NO: 53)

hTyr-a-G-bhF-Sar; (SEQ ID NO: 54)

Tyr(3-Cl)-a-G-bhF-Sar; (SEQ ID NO: 55)

(meta)Tyr-a-G-bhF-Sar; (SEQ ID NO: 56)

Tyr(3-F)-a-G-bhF-Sar; (SEQ ID NO: 57)

Tyr(3-NH$_2$)-a-G-bhF-Sar; (SEQ ID NO: 58)

Phe(4-NHCOCH3)-a-G-bhF-Sar; (SEQ ID NO: 59)

Phe(4-CONH$_2$)-a-G-bhF-Sar; (SEQ ID NO: 60)

Tic(7-NH$_2$)-a-G-bhF-Sar; (SEQ ID NO: 61)

Tyr-a-G-bhF-Sar; (SEQ ID NO: 62)

Trp(5-NH$_2$)-a-G-bhF-Sar; (SEQ ID NO: 63)

DMT-a-Sar-bhF-Sar; (SEQ ID NO: 64)

DMT-a-THP-bhF-Sar; (SEQ ID NO: 65)

DMT-a-Ala-bhF-Sar; (SEQ ID NO: 66)

DMT-a-Leu-bhF-Sar; (SEQ ID NO: 67)

DMT-a-ILeu-bhF-Sar; (SEQ ID NO: 68)

DMT-a-Val-bhF-Sar; (SEQ ID NO: 69)

Phe(2,6-dimethyl)(4-CONH$_2$)-a-G-bhF-Sar; (SEQ ID NO: 70)

Phe(4-(2-aminoethoxy))-a-G-bhF-Sar; (SEQ ID NO: 71)

DMT-a-Aib-bhF-Sar; (SEQ ID NO: 72)

DMT-a-bAla-bhF-Sar; (SEQ ID NO: 73)

Phe(2,6-dimethyl)(4-CONH$_2$)-G-G-bhF-Sar; (SEQ ID NO: 74)

Phe(2,6-dimethyl)(4-CONH$_2$)-Aib-G-bhF-Sar; (SEQ ID NO: 75)

Phe(2,6-dimethyl)(4-CONH$_2$)-(D)-Thr-G-bhF-Sar; (SEQ ID NO: 76)

Phe(2,6-dimethyl)(4-CONH$_2$)-(D)Asp-G-bhF-Sar; (SEQ ID NO: 77)

Phe(2,6-dimethyl)(4-CONH$_2$)-N(Me)Arg-G-bhF-Sar; (SEQ ID NO: 78)

Phe(2,6-dimethyl)(4-CONH$_2$)-a-G-bhF-Sar; (SEQ ID NO: 79)

Phe(2,6-dimethyl)(4-CONH$_2$)-A-G-bhF-Sar; (SEQ ID NO: 80)

DMT-G-G-bhF-Sar; (SEQ ID NO: 81)

DMT-(D)Thr-G-bhF-Sar; (SEQ ID NO: 82)

DMT-(D)Asp-G-bhF-Sar; (SEQ ID NO: 83)

DMT-(D)Tyr-G-bhF-Sar; (SEQ ID NO: 84)

Phe(2,6-dimethyl)(4-CONH$_2$)-(D)Tyr-G-bhF-Sar; (SEQ ID NO: 85)

(Ac)DMT-a-G-bhF-Sar; (SEQ ID NO: 86)

DMT-a-G-bhF-Sar; (SEQ ID NO: 87)

DMT-A-G-bhF-Sar; (SEQ ID NO: 88)

Phe(4-COOH)-a-G-bhF-Sar; (SEQ ID NO: 89)

DMT-Aib-G-bhF-Sar; (SEQ ID NO: 90)

DMT-N(Me)Arg-G-bhF-Sar; (SEQ ID NO: 91)

Phe(2,6-dimethyl-4-CONH$_2$)-a-G-bhF-N(Me)Leu; (SEQ ID NO: 92)

Phe(2,6-dimethyl-4-CONH$_2$)-a-G-bhF-N(Me)Ala; (SEQ ID NO: 93)

Phe(2,6-dimethyl-4-CONH$_2$)-a-G-bhF-Gly; (SEQ ID NO: 94)

Phe(2,6-dimethyl-4-CONH$_2$)-a-G-bhF-N(Me)Ile; (SEQ ID NO: 95)

Phe(2,6-dimethyl-4-CONH$_2$)-a-G-bhF-N(Me)Val; (SEQ ID NO: 96)

Phe(2,6-dimethyl-4-CONH$_2$)-a-G-bhF-N(Me)Nva; (SEQ ID NO: 97)

Phe(2,6-dimethyl-4-CONH$_2$)-a-G-bhF-N(Me)cha; (SEQ ID NO: 98)

(SEQ ID NO: 99)
Phe(2,6-dimethyl-4-CONH$_2$)-a-G-bhF-N(Me)Phg;

(SEQ ID NO: 100)
Phe(2,6-dimethyl-4-CONH$_2$)-a-G-bhF-N(Me)Phe;

(SEQ ID NO: 101)
Phe(2,6-dimethyl-4-CONH$_2$)-a-G-bhF-N(Me)Nle;

(SEQ ID NO: 102)
Phe(2,6-dimethyl-4-CONH$_2$)-a-G-bhF-N(Me)Tyr;

(SEQ ID NO: 103)
Phe(2,6-dimethyl-4-CONH$_2$)-Tic-G-bhF-Sar;

(SEQ ID NO: 104)
DMT-Tic-G-bhF-Sar;

(SEQ ID NO: 105)
Phe(4-tetrazolyl)-a-G-bhF-Sar;

(SEQ ID NO: 106)
Phe(2,6-dimethyl-4-CONH$_2$)-a-G-bhF-N(Me)Trp;

(SEQ ID NO: 107)
DMT-a-G-Tic-Sar;

(SEQ ID NO: 108)
Phe(2,6-dimethyl-4-CONH$_2$)-a-G-Tic-Sar;

(SEQ ID NO: 109)
Phe(2,6-dimethyl-4-CONH$_2$)-a-G-bhF(3-Cl)-Sar;

(SEQ ID NO: 110)
Phe(2,6-dimethyl-4-CONH$_2$)-a-G-bhF(44)-Sar;

(SEQ ID NO: 111)
DMT-a-G-bhF-N(Me)Ala;

(SEQ ID NO: 112)
DMT-a-G-bhF-Gly;

(SEQ ID NO: 113)
DMT-a-G-bhF-N(Me)Ile;

(SEQ ID NO: 114)
DMT-a-G-bhF-2-Nal;

(SEQ ID NO: 115)
DMT-a-G-bhF-N(ocytyl)Gly;

(SEQ ID NO: 116)
DMT-a-G-bhF-N(isopentyl)Gly;

(SEQ ID NO: 117)
DMT-a-G-bhF-N(3-isopropyloxypropyl)Gly;

(SEQ ID NO: 118)
DMT-a-G-bhF-N(benzyl)Gly;

(SEQ ID NO: 119)
DMT-a-G-bhF-N(cyclohexylmethyl)Gly;

(SEQ ID NO: 120)
DMT-a-G-bhF-N(3-propionic acid)Gly;

(SEQ ID NO: 121)
DMT-a-G-bhF-N(Phenethyl)Gly;

(SEQ ID NO: 122)
DMT-a-G-bhF-N(Trifluoroethyl)Gly;

(SEQ ID NO: 123)
DMT-a-G-bhF-N(Cyclohexyl)Gly;

(SEQ ID NO: 124)
DMT-a-G-bhF-N(amyl)Gly;

(SEQ ID NO: 125)
DMT-a-G-bhF-N(hexadecyl)Gly;

(SEQ ID NO: 163)
Phe(2,6-dimethyl-4-CONH$_2$)-a-G-bhF(2-Me)-N(Me)Nle;

(SEQ ID NO: 164)
Phe(2,6-dimethyl-4-CONH$_2$)-a-G-bhF(3-Me)-N(Me)Nle;

(SEQ ID NO: 165)
Phe(2,6-dimethyl-4-CONH$_2$)-a-G-bhF(4-Me)-N(Me)Nle;

(SEQ ID NO: 166)
Phe(2,6-dimethyl-4-CONH$_2$)-a-G-bhF(4-F)-N(Me)Nle;

(SEQ ID NO: 167)
Phe(2,6-dimethyl-4-CONH$_2$)-a-G-bhF(3-Cl)-N(Me)Nle;

(SEQ ID NO: 315)
Phe(2,6-dimethyl-4-CONH$_2$)-a-G-bhF(44)-N(Me)Nle;

(SEQ ID NO: 168)
Phe(2,6-dimethyl-4-CONH$_2$)-a-G-bhY-N(Me)Nle;

(SEQ ID NO: 316)
Phe(2,6-dimethyl-4-CONH$_2$)-a-G-bhW-N(Me)Nle;

(SEQ ID NO: 317)
Phe(2,6-dimethyl-4-CONH$_2$)-a-G-bhF-(D)N(Me)Phe;

(SEQ ID NO: 318)
Phe(2,6-dimethyl-4-CONH$_2$)-a-G-(D)N(Me)Phe-N(Me)Nle;

(SEQ ID NO: 319)
DMT-a-G-bhF(2-Me)-N(Me)Nle;

(SEQ ID NO: 320)
DMT-a-G-bhF(3-Me)-N(Me)Nle;

(SEQ ID NO: 321)
DMT-a-G-bhF(4-Me)-N(Me)Nle;

(SEQ ID NO: 322)
DMT-a-G-bhF(2-F)-N(Me)Nle;

(SEQ ID NO: 323)
DMT-a-G-bhF(3-F)-N(Me)Nle;

(SEQ ID NO: 324)
DMT-a-G-bhF(4-F)-N(Me)Nle;

(SEQ ID NO: 325)
DMT-a-G-bhF(2-Br)-N(Me)Nle;

(SEQ ID NO: 326)
DMT-a-G-bhF(3-Cl)-N(Me)Nle;

(SEQ ID NO: 327)
DMT-a-G-bhF(4-I)-N(Me)Nle;

(SEQ ID NO: 328)
DMT-a-G-bhY-N(Me)Nle;

(SEQ ID NO: 329)
DMT-a-G-bhW-N(Me)Nle;

(SEQ ID NO: 154)
DMT-a-G-(D)N(Me)Phe-N(Me)Nle;

(SEQ ID NO: 155)
DMT-a-G-bhF-N(Me)Leu;

(SEQ ID NO: 156)
DMT-a-G-bhF-N(Me)Cha;

(SEQ ID NO: 157)
DMT-a-G-bhF-N(Me)Phg;

(SEQ ID NO: 158)
DMT-a-G-bhF-N(Me)Phe;

(SEQ ID NO: 159)
DMT-a-G-bhF-N(Me)Nle;

(SEQ ID NO: 160)
DMT-a-G-bhF-N(Me)Tyr;

(SEQ ID NO: 161)
DMT-a-G-bhF-N(Me)Val;

(SEQ ID NO: 162)
DMT-a-G-bhF-NMe-Nva;

(SEQ ID NO: 163)
Phe(2,6-dimethyl-4-CONH$_2$)-a-G-bhF(2-Me)-N(Me)Nle;

(SEQ ID NO: 164)
Phe(2,6-dimethyl-4-CONH$_2$)-a-G-bhF(3-Me)-N(Me)Nle;

(SEQ ID NO: 165)
Phe(2,6-dimethyl-4-CONH$_2$)-a-G-bhF(4-Me)-N(Me)Nle;

(SEQ ID NO: 166)
Phe(2,6-dimethyl-4-CONH$_2$)-a-G-bhF(4-F)-N(Me)Nle;

(SEQ ID NO: 167)
Phe(2,6-dimethyl-4-CONH$_2$)-a-G-bhF(3-Cl)-N(Me)Nle;

(SEQ ID NO: 168)
Phe(2,6-dimethyl-4-CONH$_2$)-a-G-bhY-N(Me)Nle;

(SEQ ID NO: 169)
DMT-(D)Asp-G-bhF-N(Me)Leu;

(SEQ ID NO: 170)
DMT-(D)Asp-G-bhF-N(Me)Ala;

(SEQ ID NO: 171)
DMT-(D)Asp-G-bhF-N(Me)Trp;

(SEQ ID NO: 172)
DMT-(D)Asp-G-bhF-N(Me)Ile;

(SEQ ID NO: 173)
DMT-(D)Asp-G-bhF-N(Me)Val;

(SEQ ID NO: 174)
DMT-(D)Asp-G-bhF-N(Me)Nva;

(SEQ ID NO: 175)
DMT-(D)Asp-G-bhF-N(Me)Cha;

(SEQ ID NO: 176)
DMT-(D)Asp-G-bhF-N(Me)Phg;

(SEQ ID NO: 177)
DMT-(D)Asp-G-bhF-N(Me)Phe;

(SEQ ID NO: 178)
DMT-(D)Asp-G-bhF-N(Me)Nle;

(SEQ ID NO: 179)
DMT-(D)Asp-G-bhF-Gly;

(SEQ ID NO: 180)
DMT-(D)Asp-G-bhF-N(Me)Tyr;

(SEQ ID NO: 181)
DMT-a-G-bhF(2-Me)-N(Me)Nle;

(SEQ ID NO: 182)
DMT-D-Thr-G-bhF-N(Me)Ile;

(SEQ ID NO: 183)
DMT-D-Thr-G-bhF-N(Me)Ala;

(SEQ ID NO: 184)
DMT-a-G-bhF-N(Me)Nva;

(SEQ ID NO: 185)
DMT-(D)Glu-G-bhF-N(Me)Ala;

(SEQ ID NO: 186)
DMT-(D)Glu-G-bhF-N(Me)Ile;

(SEQ ID NO: 187)
DMT-(D)Glu-G-bhF-Sar;

(SEQ ID NO: 319)
DMT-a-G-bhF(2-Me)-N(Me)Nle;

(SEQ ID NO: 320)
DMT-a-G-bhF(3-Me)-N(Me)Nle;

(SEQ ID NO: 321)
DMT-a-G-bhF(4-Me)-N(Me)Nle;

(SEQ ID NO: 322)
DMT-a-G-bhF(2-F)-N(Me)Nle;

(SEQ ID NO: 323)
DMT-a-G-bhF(3-F)-N(Me)Nle;

(SEQ ID NO: 324)
DMT-a-G-bhF(4-F)-N(Me)Nle;

(SEQ ID NO: 325)
DMT-a-G-bhF(2-Br)-N(Me)Nle;

(SEQ ID NO: 326)
DMT-a-G-bhF(3-Cl)-N(Me)Nle;

(SEQ ID NO: 327)
DMT-a-G-bhF(4-I)-N(Me)Nle;

(SEQ ID NO: 328)
DMT-a-G-bhY-N(Me)Nle;

(SEQ ID NO: 329)
DMT-a-G-bhW-N(Me)Nle;

(SEQ ID NO: 154)
DMT-a-G-(D)N(Me)Phe-N(Me)Nle;

(SEQ ID NO: 155)
DMT-a-G-bhF-N(Me)Leu;

(SEQ ID NO: 156)
DMT-a-G-bhF-N(Me)Cha;

(SEQ ID NO: 157)
DMT-a-G-bhF-N(Me)Phg;

(SEQ ID NO: 158)
DMT-a-G-bhF-N(Me)Phe;

(SEQ ID NO: 159)
DMT-a-G-bhF-N(Me)Nle;

(SEQ ID NO: 160)
DMT-a-G-bhF-N(Me)Tyr;
or (SEQ ID NO: 161)
DMT-a-G-bhF-N(Me)Val;

In certain embodiments of the opioid agonist peptide or pharmaceutically acceptable salt or solvate thereof of any of Formulas I-XVIIIl, X1-X5 comprises or consists of a sequence set forth in Table 3B, SEQ ID NOs: 1-153, Table 3C, SEQ ID NOs: 154-187, Table 3E, SEQ ID NOs: 188-266, Table 3F, SEQ ID NOs:267-273, SEQ ID NOs: 274-336, or any of the following sequences:

(SEQ ID NO: 43)
DMT-((D)Ala)-Gly-(β-homoPhe)-Sar;

(SEQ ID NO: 62)
Tyr-((D)Ala)-Gly-(β-homoPhe)-Sar;

DMT-((D)Ala)-Gly-(β-homoPhe)-Gly; (SEQ ID NO: 112)

Phe(2,6-dimethyl-4-CONH$_2$)-((D)Ala)-Gly-(β-homoPhe)-Gly; (SEQ ID NO: 94)

Phe(2,6-dimethyl-4-CONH$_2$)-((D)Ala)-Gly-(β-homoPhe)-Sar; (SEQ ID NO: 85)

DMT-((D)Thr)-Gly-(β-homoPhe)-Sar; (SEQ ID NO: 82)

DMT-((D)Asp)-Gly-(β-homoPhe)-Sar; (SEQ ID NO: 83)

DMT-((D)Tyr)-Gly-(β-homoPhe)-Sar; (SEQ ID NO: 84)

Phe(2,6-dimethyl-4-CONH$_2$)-((D)Ala)-Gly-(β-homoPhe)-(N(Me)Ala); (SEQ ID NO: 93)

Phe(2,6-dimethyl-4-CONH$_2$)-((D)Ala)-Gly-(β-homoPhe)-(N(Me)Val); (SEQ ID NO: 96)

Phe(2,6-dimethyl-4-CONH$_2$)-((D)Ala)-Gly-(β-homoPhe)-(N(Me)Phg); (SEQ ID NO: 99)

Phe(2,6-dimethyl-4-CONH$_2$)-((D)Ala)-Gly-(β-homoPhe)-(N(Me)Nle); (SEQ ID NO: 101)

Phe(2,6-dimethyl-4-CONH$_2$)-((D)Ala)-Gly-(β-homoPhe)-(N(Me)Tyr); (SEQ ID NO: 102)

DMT-((D)Ala)-Gly-(β-homoPhe)-Sar-NH$_2$; (SEQ ID NO: 43)

Tyr-((D)Ala)-Gly-(β-homoPhe)-Sar-NH$_2$; (SEQ ID NO: 62)

DMT-((D)Ala)-Gly-(β-homoPhe)-Gly-NH$_2$; (SEQ ID NO: 112)

DMT-((D)Ala)-Gly-(β-homoPhe)-Gly-OH; (SEQ ID NO: 112)

Phe(2,6-dimethyl-4-CONH$_2$)-((D)Ala)-Gly-(β-homoPhe)-Gly-NH$_2$; (SEQ ID NO: 94)

Phe(2,6-dimethyl-4-CONH$_2$)-((D)Ala)-Gly-(β-homoPhe)-Sar-NH$_2$; (SEQ ID NO: 85)

Phe(2,6-dimethyl-4-CONH$_2$)-((D)Ala)-Gly-(β-homoPhe)-Sar-OH; (SEQ ID NO: 85)

DMT-((D)Thr)-Gly-(β-homoPhe)-Sar-NH$_2$; (SEQ ID NO: 82)

DMT-((D)Asp)-Gly-(β-homoPhe)-Sar-NH$_2$; (SEQ ID NO: 83)

DMT-((D)Tyr)-Gly-(β-homoPhe)-Sar-NH$_2$; (SEQ ID NO: 84)

Phe(2,6-dimethyl-4-CONH$_2$)-((D)Ala)-Gly-(β-homoPhe)-(N(Me)Ala)-NH$_2$; (SEQ ID NO: 93)

Phe(2,6-dimethyl-4-CONH$_2$)-((D)Ala)-Gly-(β-homoPhe)-(N(Me)Val)-NH$_2$; (SEQ ID NO: 96)

Phe(2,6-dimethyl-4-CONH$_2$)-((D)Ala)-Gly-(β-homoPhe)-(N(Me)Phg)-NH$_2$; (SEQ ID NO: 99)

Phe(2,6-dimethyl-4-CONH$_2$)-((D)Ala)-Gly-(β-homoPhe)-(N(Me)Nle)-NH$_2$; (SEQ ID NO: 101)

or

Phe(2,6-dimethyl-4-CONH$_2$)-((D)Ala)-Gly-(β-homoPhe)-(N(Me)Tyr)-NH$_2$. (SEQ ID NO: 102)

In a particular embodiment, the opioid agonist peptide or pharmaceutically acceptable salt or solvate thereof comprises or consists of any of the following sequences:

DMT-(D)Ala-Gly-Phe-nLeu-NH$_2$; (SEQ ID NO: 37)

DMT-(D)Ala-Gly-Phe(4-F)-Gly-NH$_2$; (SEQ ID NO: 38)

DMT-(D)Ala-Gly-Phe(4-CN)-Gly-NH$_2$; (SEQ ID NO: 39)

DMT-(D)Ala-Gly-Phe(3,4-dichloro)-Gly-NH$_2$; (SEQ ID NO: 41)

DMT-(D)Ala-Gly-(b-homoPhe)-Sar-NH$_2$; (SEQ ID NO: 43)

DMT-dTic-Gly-Phe-Sar-NH$_2$; (SEQ ID NO: 45)

DMT-(D)Ala-homoPhe-Sar-NH$_2$; (SEQ ID NO: 46)

DMT-(D)Ala-homoPhe-nLeu-NH$_2$; (SEQ ID NO: 48)

DMT-(D)Ala-Ala-(b-homoPhe)-Sar-NH$_2$; (SEQ ID NO: 66)

Phe(2,6-dimethyl-4-CONH$_2$)-(D)Ala-Gly-(b-homoPhe)-Sar-NH$_2$; (SEQ ID NO: 70)

Phe(2,6-dimethyl-4-CONH$_2$)-(D)Ala-Gly-(b-homoPhe)-Sar-OH; (SEQ ID NO: 70)

DMT-(D)Thr-Gly-(b-homoPhe)-Sar-NH$_2$; (SEQ ID NO: 82)

DMT-(D)Asp-Gly-(b-homoPhe)-Sar-NH$_2$; (SEQ ID NO: 83)

DMT-(D)Tyr-Gly-(b-homoPhe)-Sar-NH$_2$; (SEQ ID NO: 84)

-continued

DMT-(D)Ala-Gly-(b-homoPhe)-Sar-OH; (SEQ ID NO: 43)

Phe(2,6-dimethyl-4-CONH$_2$)-(D)Ala-Gly-(b-homoPhe)-N(Me)Ala-NH$_2$; (SEQ ID NO: 93)

Phe(2,6-dimethyl-4-CONH$_2$)-(D)Ala-Gly-(b-homoPhe)-N(Me)Val-NH$_2$; (SEQ ID NO: 96)

Phe(2,6-dimethyl-4-CONH$_2$)-(D)Ala-Gly-(b-homoPhe)-N(Me)Phg-NH$_2$; (SEQ ID NO: 99)

Phe(2,6-dimethyl-4-CONH$_2$)-(D)Ala-Gly-(b-homoPhe)-N(Me)Tyr-NH$_2$; (SEQ ID NO: 102)

DMT-(D)Ala-Gly-(b-homoPhe)-N(Me)Ala-NH$_2$; (SEQ ID NO: 111)

DMT-(D)Ala-Gly-(b-homoPhe)-Gly-NH$_2$; (SEQ ID NO: 112)

DMT-(D)Ala-Gly-(b-homoPhe)-N(Me)ILe-NH$_2$; (SEQ ID NO: 113)

DMT-(D)Ala-Gly-(b-homoPhe)-N(isopentyl)Gly-NH$_2$; (SEQ ID NO: 116)

DMT-(D)Ala-Gly-(b-homoPhe)-N(3-isopropyloxypropyl)Gly-NH$_2$; (SEQ ID NO: 117)

DMT-(D)Ala-Gly-(b-homoPhe)-N(benzyl)Gly-NH$_2$; (SEQ ID NO: 118)

DMT-(D)Ala-Gly-(b-homoPhe)-N(3-propionicacid)Gly-NH$_2$; (SEQ ID NO: 120)

DMT-(D)Ala-Gly-(b-homoPhe)-N(Phenethyl)Gly-NH$_2$; (SEQ ID NO: 121)

DMT-(D)Ala-Gly-(b-homoPhe)-N(Trifluoroethyl)Gly-NH$_2$; (SEQ ID NO: 122)

DMT-(D)Ala-Gly-(b-homoPhe)-N(Cyclohexyl)Gly-NH$_2$; (SEQ ID NO: 123)

DMT-(D)Ala-Gly-(b-homoPhe)-N(amyl)Gly-NH$_2$; (SEQ ID NO: 124)

DMT-(D)Ala-Gly-(D)N(Me)Phe-N(Me)Nle-NH$_2$; (SEQ ID NO: 154)

DMT-(D)Ala-Gly-(b-homoPhe)-N(Me)-Leu-NH$_2$; (SEQ ID NO: 155)

DMT-(D)Ala-Gly-(b-homoPhe)-N(Me)-Phg-NH$_2$; (SEQ ID NO: 157)

DMT-(D)Ala-Gly-(b-homoPhe)-N(Me)-Phe-NH$_2$; (SEQ ID NO: 158)

DMT-(D)Ala-Gly-(b-homoPhe)-N(Me)-Nle-NH$_2$; (SEQ ID NO: 159)

DMT-(D)Ala-Gly-(b-homoPhe)-N(Me)-Tyr-NH$_2$; (SEQ ID NO: 160)

DMT-(D)Ala-Gly-(b-homoPhe)-N(Me)-Val-NH$_2$; (SEQ ID NO: 161)

DMT-(D)Ala-Gly-(b-homoPhe)-N(Me)-Nva-OH; (SEQ ID NO: 162)

DMT-(D)Asp-Gly-(b-homoPhe)-N(Me)-Leu-OH; (SEQ ID NO: 169)

DMT-(D)Asp-Gly-(b-homoPhe)-N(Me)-Ala-OH; (SEQ ID NO: 170)

DMT-(D)Asp-Gly-(b-homoPhe)-N(Me)-Trp-OH; (SEQ ID NO: 171)

DMT-(D)Asp-Gly-(b-homoPhe)-N(Me)-Ile-OH; (SEQ ID NO: 172)

DMT-(D)Asp-Gly-(b-homoPhe)-N(Me)-Val-OH; (SEQ ID NO: 173)

DMT-(D)Asp-Gly-(b-homoPhe)-N(Me)-Nva-OH; (SEQ ID NO: 174)

DMT-(D)Asp-Gly-(b-homoPhe)-N(Me)-Cha-OH; (SEQ ID NO: 175)

DMT-(D)Asp-Gly-(b-homoPhe)-N(Me)-Phg-OH; (SEQ ID NO: 176)

DMT-(D)Asp-Gly-(b-homoPhe)-N(Me)-Phe-OH; (SEQ ID NO: 177)

DMT-(D)Asp-Gly-(b-homoPhe)-N(Me)-Nle-OH; (SEQ ID NO: 178)

DMT-(D)Asp-Gly-(b-homoPhe)-Gly-OH; (SEQ ID NO: 179)

DMT-(D)Asp-Gly-(b-homoPhe)-N(Me)-Tyr-OH; (SEQ ID NO: 180)

DMT-(D)Thr-Gly-(b-homoPhe)-N(Me)-Ile-OH; (SEQ ID NO: 182)

DMT-(D)Thr-Gly-(b-homoPhe)-N(Me)-Ala-OH; (SEQ ID NO: 183)
or

DMT-(D)Ala-Gly-(b-homoPhe)-N(Me)-Nva-NH$_2$. (SEQ ID NO: 184)

In a particular embodiment, the opioid agonist peptide or pharmaceutically acceptable salt or solvate thereof comprises or consists of any of the following sequences:

DMT-(D)Arg-Phe(4-CN)-Sar-NH$_2$; (SEQ ID NO: 20)

Tyr-(D)Ala-Gly-(b-homoPhe)-Sar-NH$_2$; (SEQ ID NO: 62)

DMT-(D)Ala-Gly-(b-homoTrp)-N(Me)Leu-OH; (SEQ ID NO: 153)

Phe(2,6-dimethyl-4-CONH$_2$)-(D)Ala-Gly-(b-homoTyr)-N(Me)Nle-OH; (SEQ ID NO: 168)

DMT-(D)Glu-Gly-(b-homoPhe)-N(Me)-Ala-OH; (SEQ ID NO: 185)

DMT-(D)Glu-Gly-(b-homoPhe)-N(Me)-Ile-OH; (SEQ ID NO: 186)

-continued

DMT-(D)Ala-Gly-b-homoPhe(2-Me)-N(Me)Nle-OH; (SEQ ID NO: 319)
or

DMT-(D)Arg-BIP-Sar-NH₂. (SEQ ID NO: 23)

In a particular embodiment, the opioid agonist peptide or pharmaceutically acceptable salt or solvate thereof comprises or consists of any of the following sequences:

DMT-(D)Arg-(Phe)-Sar-NH₂; (SEQ ID NO: 9)

DMT-N(Me)-(D)Ala-(Phe)-Sar-NH₂; (SEQ ID NO: 10)

DMT-(D)Arg-1-Nal-(Me)bAla-OH; (SEQ ID NO: 13)

DMT-(D)Arg-Phe(4-F)-Sar-NH₂; (SEQ ID NO: 19)

DMT-dTic-(Phe)-Sar-NH₂; (SEQ ID NO: 44)

DMT-(D)Ala-Gly-(homoPhe)-Sar-NH₂; (SEQ ID NO: 47)

DMT-(D)Ala-Gly-(homoPhe)-nLeu-NH₂; (SEQ ID NO: 49)

Phe(2,6-dimethyl-4-CONH₂)-(D)Ala-Gly- (SEQ ID NO: 92)
(b-homoPhe)-N(Me)Leu-NH₂;

Phe(2,6-dimethyl-4-CONH₂)-(D)Ala-Gly- (SEQ ID NO: 100)
(b-homoPhe)-N(Me)Phe-NH₂;

Phe(2,6-dimethyl-4-CONH₂)-(D)Ala-Gly- (SEQ ID NO: 101)
(b-homoPhe)-N(Me)Nle-NH₂;

DMT-(D)Ala-Gly-(b-homoPhe)-N(cyclohexylmethyl)Gly- (SEQ ID NO: 119)
NH₂;

Phe(2,6-dimethyl-4-CONH₂)-(D)Ala-Gly-bhW- (SEQ ID NO: 139)
N(Me)Leu-OH;

DMT-(D)Ala-Gly-bhF-N(Me)-Cha-NH₂; (SEQ ID NO: 156)
or

DMT-(D)Glu-Gly-bhF-Sar-NH₂. (SEQ ID NO: 187)

In particular embodiments, the present invention includes an opioid agonist peptide dimer, comprising two peptide monomers, wherein each peptide monomer comprises or consists of an amino acid sequence of Formula I:

Y1-Y2-Y3-X1-X2-X3-X4-X5-Y4-Y5-Y6 (Formula I); (SEQ ID NO: 339)

or a pharmaceutically acceptable salt or solvate thereof, wherein:
Y1 is absent or any amino acid;
Y2 is absent or any amino acid;
Y3 is absent or any amino acid;
X1 is Tyr, D-Tyr, a Tyr analog, Tic, a Tic analog, or a Phe analog;
X2 is any amino acid;
X3 is any amino acid;
X4 is any amino acid;
X5 is absent or any amino acid;
Y4 is absent or any amino acid;
Y5 is absent or any amino acid; and
Y6 is absent or any amino acid,
wherein the two peptides are connected via a linker moiety.

In one embodiment, X5 is absent. In another embodiment, X5 is any amino acid. In another embodiment, X5 is a hydrophobic amino acid. In yet another embodiment, X5 is any N-methylamino acid. In certain embodiments, X5 is absent, any N-methylamino acid, or X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly. In certain embodiments, X5 is absent, a hydrophobic amino acid, or an amino acid selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl) Gly, N(cyclohexylmethyl)Gly, N(3-propanoic acid)Gly, N(phenethyl)Gly, 2-Nal, N(octyl)Gly, and N(isopentyl)Gly. In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl) Gly, N(cyclohexylmethyl)Gly, N(3-propanoic acid)Gly, N(phenethyl)Gly, 2-Nal, N(octyl)Gly, and N(isopentyl)Gly. In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, and N(Me)Nva.

In another particular embodiments, the present invention includes an opioid agonist peptide dimer, comprising two peptide monomers, wherein each peptide monomer comprises or consists of an amino acid sequence of any of Formulas I, Ia, IIa-XVIIIl, and wherein X2-X5 are as described herein. In certain embodiments of opioid agonist peptide dimers or pharmaceutically acceptable salts or solvates thereof disclosed herein, X1-X5 comprises or consists of a sequence set forth in Table 3B, SEQ ID NOs: 1-153, Table 3C, SEQ ID NOs: 154-187, Table 3E, SEQ ID NOs: 188-266, Table 3F, SEQ ID NOs: 267-273, SEQ ID NOs: 274-336, or any of the sequences disclosed herein.

In particular embodiments of any of the opioid agonist peptide dimers disclosed herein, one or more of Y4, Y5 and/or Y6 is present in each of the peptide monomers. In particular embodiments, one of Y4, Y5, or Y6 of the peptide monomers is connected via the linker moiety.

In particular embodiments of any of the opioid agonist peptide dimers disclosed herein, one or more of Y4, Y5 and/or Y6 is an amino acid comprising a side chain containing a group capable of being cross-linked to another peptide via a linker. In particular embodiments, this amino acid is the C-terminal amino acid of the peptide monomers.

In particular embodiments, the two monomers are linked via a linker bound to these functional groups. In certain embodiments, the amino acid comprises a side chain containing an amine, acid, alcohol, thio, azide, alkyne, halide or acid halide group. In certain embodiments wherein Y4, Y5 or Y6 comprises any of these amino acid residues, the two monomers are connected via a linker bound to Y4, Y5, or Y6 of each monomer. In certain embodiments, the peptide monomers are connected by Y4, Y5 or Y6, which may be an internal amino acid residue or a C-terminal amino acid residue.

In certain embodiments, Y4, Y5, and/or Y6, or the C-terminal amino acid, of a monomer comprises any amino acid with an amine side chain, Lys, D-Lys, N(Me)-Lys, D-N(Me)-Lys, Orn, Dab, Dap, HomoLys, D-Dap, D-Dab, D-Orn, Cys, HomoCys, Pen, D-HomoCys, D-Cys, D-Pen, Asp, Glu, D-Asp, D-Glu, HomoSer, Asp, Glu, homoGlu, D-Asp, D-Glu, D-homoGlu, N(Me)-Glu, N(Me)-Asp, N(Me)-D-Glu, or N(Me)-D-Asp. In certain embodiments, Y4, Y5, and/or Y6, or the C-terminal amino acid, of a monomer is selected from Asp, Glu, homoGlu, D-Asp, D-Glu, D-homoGlu, N(Me)-Glu, N(Me)-Asp, N(Me)-D-Glu, and N(Me)-D-Asp. In particular embodiments, Y4, Y5, or Y6 is an amino acid comprising an amine side chain, or is selected from the group consisting of, Lys, D-Lys, N(Me)-Lys, D-N(Me)-Lys, Orn, Dab, Dap, HomoLys, D-Dap, D-Dab, D-Orn, Asp, Glu, D-Asp, D-Glu, HomoSer, Homo-Glu, D-homoGlu, N(Me)-Glu, N(Me)-Asp, N(Me)-D-Glu, and N(Me)-D-Asp. In particular embodiments, Y4, Y5, or Y6 is the C-terminal amino acid of the peptide monomers and is an amino acid comprising an amine side chain, or is selected from the group consisting of: Lys, D-Lys, N(Me)-Lys, D-N(Me)-Lys, Orn, Dab, Dap, HomoLys, D-Dap, D-Dab, D-Orn, Asp, Glu, D-Asp, D-Glu, HomoSer, Homo-Glu, D-homoGlu, N(Me)-Glu, N(Me)-Asp, N(Me)-D-Glu, and N(Me)-D-Asp. In particular embodiments, these C-terminal amino acids of the peptide monomers are connected via the linker moiety. In certain embodiments, the C-terminal amino acid of each peptide monomer is a Lys or another amino acid comprising an amine side chain, and the amine groups of the C-terminal amino acids are connected via a linker. In certain embodiments, Y4, Y5 or Y6 is an internal amino acid and is a Lys or another amino acid comprising an amine side chain, and the amine groups of these amino acids are connected via a linker. In particular embodiments, the two C-terminal amino acids of each subunit of a peptide dimer compound possess acid functionality, and they are linked through retroinverse linking by a diamine linker. In certain embodiments of any of the opioid agonist peptide dimers disclosed herein, any of the amino acids Y1 or Y2 or Y3 or Y4, or Y5 or Y6 is an amino acid comprising a side chain containing a group capable of being cross-linked to another peptide via a linker, When the amino acid comprises a side chain containing an amine, acid, alcohol, thio, azide, alkyne, halide or acid halide group, the two peptide monomers are connected to form dimer through a linker moiety with suitable functional group by forming corresponding amide bond, ether bond, thio ether bond and cycloaddition of alkynes to azides to form triazoles. In particular embodiments of any of the opioid agonist peptide dimers disclosed herein, the C-terminus of each peptide monomer is an amino acid comprising an amine side chain, or it comprises a C-terminal acid or —OH group.

In certain embodiments of an opioid agonist peptide dimer or pharmaceutically acceptable salt or solvate thereof comprising peptide monomers of Formula I:

X1 is Tyr, DMT, β-homo-Tyr, N(Me)-Tyr, Tyr(3-tBu), (D)Tyr, homo-Tyr, Tyr(3-Cl), meta-Tyr, Tyr(3-F), Tyr(3-OH), Phe(4-NHCOCH₃), Phe(4-CONH₂), Tic, Phe(2,6-dimethyl-4-CONH₂), Phe(4-(2-aminoethoxy), Phe(4-COOH), Phe(2,6-dimethyl)(4-tetrazole), Phe(2,6-dimethyl)(4-imidazole), or Phe(2,6-dimethyl)(4-triazole).

In certain embodiments of an opioid agonist peptide dimer or pharmaceutically acceptable salt or solvate thereof comprising peptide monomers of Formula I:
X2 is (D)Arg, (D)N(Me)-Ala, (D)Ala, (D)Tic, (D)Lys, (D)Orn, (D)Thr, (D)Asp, or (D)Tyr.

In certain embodiments of an opioid agonist peptide dimer or pharmaceutically acceptable salt or solvate thereof comprising peptide monomers of Formula I:
X3 is (D)Phe, Phe, Bip, His, Aba, Trp, β-homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or β-Ala.

In certain embodiments of an opioid agonist peptide dimer or pharmaceutically acceptable salt or solvate thereof comprising peptide monomers of Formula I:
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, a substituted β-homoPhe, N(Octyl)Gly, Leu, Val, DPA, Trp, Phe, Phe(4-CN), Tic, or a substituted aromatic amino acid (optionally, Phe(3,4-dichloro), β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp, or an amino acid having one of the following structures:

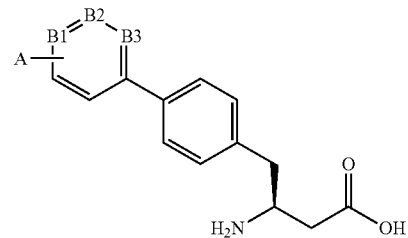

A = Alkyl, CF3, OH, halide in position 1-3

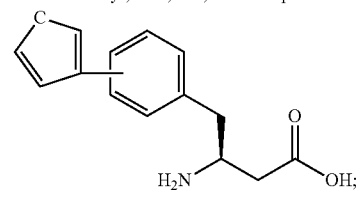

C = O, S and wherein each of B1, B2, and B3 is independently CH or N.

In certain embodiments of an opioid agonist peptide dimer or pharmaceutically acceptable salt or solvate thereof comprising peptide monomers of Formula I:
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, a substituted β-homoPhe, N(Octyl)Gly, Leu, Val, DPA, Trp, Tic, Phe, a substituted aromatic amino acid (optionally, Phe(4-CN), Phe(3,4-dichloro), β-homoPhe(2-F), β-homoPhe(3-F), β-homoPhe(4-F), β-homoPhe(2-Me), β-homoPhe(3-Me), β-homoPhe(4-Me), β-homoPhe(4-

NO₂), β-homoPhe(4-OH), β-homoPhe(3-Cl), β-homo-Phe(2-Br), β-homoPhe(3-Br), β-homoPhe(4-Br), β-homoPhe(4-I), or β-homoTrp, N(Me)Tyr, N(Me)Phe, N(Me)Leu, N(Me)Ala, N(Me)Phg, N(Me)Cha, N(Me)Nle, N(Me)Val, (D)N(Me)-Phe, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(Octyl)Gly, or N(isopentyl)Gly.

In certain embodiments of an opioid agonist peptide dimer or pharmaceutically acceptable salt or solvate thereof comprising peptide monomers of Formula I:
X4 is β-homoPhe or a substituted aromatic amino acid (optionally, Phe(3,4-dichloro), β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp, or an amino acid having one of the following structures:

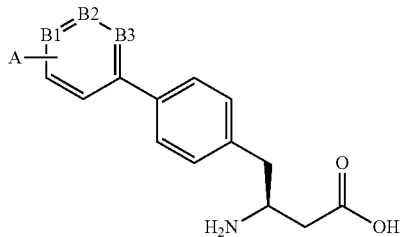

A = Alkyl, CF3, OH, halide in position 1-3

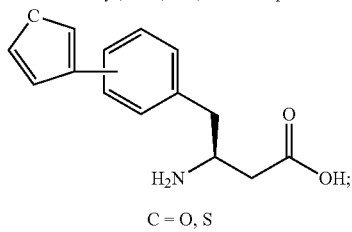

C = O, S and wherein each of B1, B2, and B3 is independently CH or N.

In certain embodiments of an opioid agonist peptide dimer or pharmaceutically acceptable salt or solvate thereof comprising peptide monomers of Formula I:
X4 is β-homoPhe or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I) or β-homoPhe(4-OH)).

In certain embodiments of an opioid agonist peptide dimer or pharmaceutically acceptable salt or solvate thereof comprising peptide monomers of Formula I:
X5 is Sarcosine, a hydrophobic amino acid, N(Me)Nle, N(Me)Val, N(Me)Leu, N(Me)Phe, Gly, β-Ala, β-homoAla, Asn or (D)Asn N(Me)Tyr, N(Me)Phg, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(Octyl)Gly, or N(isopentyl)Gly, optionally wherein X5 is not Leu, Met, or (D)Leu.

In certain embodiments of an opioid agonist peptide dimer or pharmaceutically acceptable salt or solvate thereof comprising peptide monomers of Formula I:

X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly.

In certain embodiments of an opioid agonist peptide dimer or pharmaceutically acceptable salt or solvate thereof comprising peptide monomers of Formula I:
X5 is not Leu, Met, or (D)Leu.

In certain embodiments of an opioid agonist peptide dimer or pharmaceutically acceptable salt or solvate thereof comprising peptide monomers of Formula I:
X1 is Tyr, (D)Tyr, a Tyr analog, a Phe analog, Tic, or a Tic analog;
X2 is a (D) amino acid;
X3 is any amino acid;
X4 is β-homoPhe or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp); and
X5 is absent, a hydrophobic amino acid, or selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In certain embodiments of an opioid agonist peptide dimer or pharmaceutically acceptable salt or solvate thereof comprising peptide monomers of Formula I:
X1 is Tyr, DMT, β-homo-Tyr, N(Me)-Tyr, Tyr(3-tBu), homo-Tyr, Tyr(3-Cl), Tyr(3-F), Tyr(3-OH), Phe(4-NHCOCH₃), Phe(4-CONH₂), Tic, Phe(2,6-dimethyl-4-CONH₂), Phe(4-(2-aminoethoxy), or Phe(4-COOH);
X2 is (D)Arg, N(Me)-(D)Ala, (D)Ala, (D)Tic, (D)Lys, (D)Orn, (D)Thr, (D)Asp, or (D)Tyr;
X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or β-Ala;
X4 is Lys, (D)Lys, N(Me)-Lys, Gly, Sar, Me-β-Ala, (D)N(Me)-Phe, α-Me-Phe, Phe(4-F), Phe(3,4-dimethoxy), β-homoPhe, N(Octyl)Gly, Leu, Val, DPA, Trp, Phe, Phe(4-CN), Tic, Phe(3,4-dichloro), or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp; and
X5 is absent, a hydrophobic amino acid, or selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly, optionally wherein X5 is not Leu, Met, or (D)Leu.

In certain embodiments of an opioid agonist peptide dimer or pharmaceutically acceptable salt or solvate thereof comprising peptide monomers of Formula I:
X1 is Tyr, DMT, or Phe(2,6-dimethyl-4-CONH₂);
X2 is a (D) amino acid;
X3 is Gly or β-Ala;
X4 is β-homoPhe or a substituted aromatic amino acid (optionally, β-homoPhe(2-Me), β-homoPhe(3-Me), β-homoPhe(4-Me), β-homoPhe(2-F), β-homoPhe(3-F), β-homoPhe(4-F), β-homoPhe(2-Br), β-homoPhe(3-Br), β-homoPhe(4-Br), β-homoPhe(3-Cl), β-homoPhe(4-I), β-homoPhe(4-OH), β-homoPhe(4-NO₂), (D)N(Me)-Phe, or β-homoTrp; and
X5 is absent, a hydrophobic amino acid, or selected from Sar, Gly, Aib, β-Ala, N(Me)Nle, N(Me)Val, N(Me)Leu, N(Me)Phe, N(Me)Tyr, N(Me)Phg, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(Octyl)Gly, and N(isopentyl)Gly, optionally wherein X5 is not Leu, Met, or (D)Leu.

In particular embodiments, X4 is β-homoPhe.

In certain embodiments of an opioid agonist peptide dimer or pharmaceutically acceptable salt or solvate thereof comprising peptide monomers of Formula I:
X1 is Tyr, DMT, or Phe(2,6-dimethyl-4-CONH₂);
X2 is (D)Arg, (D)Ala, or (D)Tic;
X3 is Gly, Phe, a Phe analog, Aba, Trp, 1-Nal, Bip, Ala, Leu, or Ile;
X4 is a Phe analog, optionally β-homoPhe; and
X5 is absent, a hydrophobic amino acid, or selected from Sar, Gly, Aib, β-Ala, N(Me)Nle, N(Me)Val, N(Me)Leu, N(Me)Phe, N(Me)Tyr, N(Me)Phg, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(Octyl)Gly, and N(isopentyl)Gly, optionally wherein X5 is not Leu, Met, or (D)Leu; or
X5 is Sar, N(Me)Nle, N(Me)Val, N(Me)Leu, N(Me)Phe, N(Me)Tyr, N(Me)Phg, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(Octyl)Gly, or N(isopentyl)Gly.

In certain embodiments of an opioid agonist peptide dimer or pharmaceutically acceptable salt or solvate thereof comprising peptide monomers of Formula I:
X1-X5 comprises or consists of a sequence set forth in Table 3B, SEQ ID NOs: 1-153, Table 3C, SEQ ID NOs: 154-187, Table 3E, SEQ ID NOs: 188-266, Table 3F, SEQ ID NOs: 267-273, SEQ ID NOs: 274-336, or any of the following sequences:

```
                                            (SEQ ID NO: 43)
DMT-((D)Ala)-Gly-(β-homoPhe)-Sar;

(SEQ ID NO: 62)
Tyr-((D)Ala)-Gly-(β-homoPhe)-Sar;

(SEQ ID NO: 112)
DMT-((D)Ala)-Gly-(β-homoPhe)-Gly;

(SEQ ID NO: 94)
Phe(2,6-dimethyl-4-CONH₂)-((D)Ala)-Gly-
(β-homoPhe)-Gly;
```

```
                                            (SEQ ID NO: 85)
Phe(2,6-dimethyl-4-CONH₂)-((D)Ala)-Gly-
(β-homoPhe)-Sar;

(SEQ ID NO: 82)
DMT-((D)Thr)-Gly-(β-homoPhe)-Sar;

(SEQ ID NO: 83)
DMT-((D)Asp)-Gly-(β-homoPhe)-Sar;

(SEQ ID NO: 84)
DMT-((D)Tyr)-Gly-(β-homoPhe)-Sar;

(SEQ ID NO: 93)
Phe(2,6-dimethyl-4-CONH₂)-((D)Ala)-Gly-
(β-homoPhe)-(N(Me)Ala);

(SEQ ID NO: 96)
Phe(2,6-dimethyl-4-CONH₂)-((D)Ala)-Gly-
(β-homoPhe)-(N(Me)Val);

(SEQ ID NO: 99)
Phe(2,6-dimethyl-4-CONH₂)-((D)Ala)-Gly-
(β-homoPhe)-(N(Me)Phg);

(SEQ ID NO: 101)
Phe(2,6-dimethyl-4-CONH₂)-((D)Ala)-Gly-
(β-homoPhe)-(N(Me)Nle);
or
                                            (SEQ ID NO: 102)
Phe(2,6-dimethyl-4-CONH₂)-((D)Ala)-Gly-
(β-homoPhe)-(N(Me)Tyr).
```

It is understood that where the N-terminus and/or C-terminus of the sequences are not specifically defined, they may include any group, e.g., an —NH₂ group or an —OH group. In certain embodiments, an opioid agonist peptide dimer or pharmaceutically acceptable salt or solvate thereof comprises peptide monomers of any of the following sequences:

```
                                            (SEQ ID NO: 267)
[DMT-((D)Ala)-Gly-(β-homoPhe)-(Sar)]₂-Lys;

(SEQ ID NO: 268)
[DMT-((D)Ala)-Gly-(β-homoPhe)-(NMe-Ala)]₂-Lys;

(SEQ ID NO: 269)
[DMT-((D)Ala)-Gly-(β-homoPhe)-(NMe-Ile)]₂-Lys;

(SEQ ID NO: 270)
[DMT-((D)Ala)-Gly-(β-homoPhe)-(Sar)]₂-(D-Lys);
or
                                            (SEQ ID NO: 271)
[DMT-((D)Ala)-Gly-(β-homoPhe)-(Sar)-(D-Lys)]₂-DIG.
```

In certain embodiments of an opioid agonist peptide dimer or pharmaceutically acceptable salt or solvate thereof comprising peptide monomers of Formula I, the linker moiety is selected from the linkers depicted in Table 2, L- or D-lysinamide or derivatives thereof, piperazine or derivatives thereof, and PEG based diamines, optionally having any of the following structures:

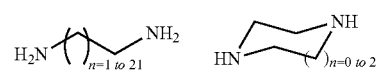

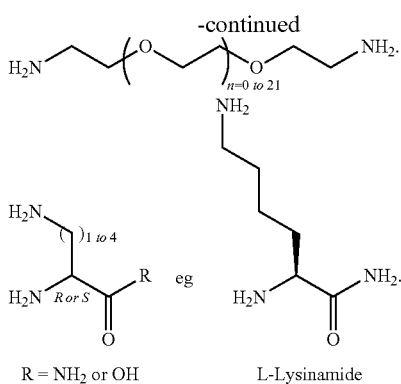

R = NH₂ or OH     L-Lysinamide

In certain embodiments of an opioid agonist peptide dimer or pharmaceutically acceptable salt or solvate thereof comprising peptide monomers of Formula I, the C-terminus of each peptide monomer is connected by the linker moiety.

In certain embodiments of an opioid agonist peptide dimer, the peptide dimer is according to Formula D-I:

wherein the peptide of Formula I and the linker are as described herein.

In one embodiment, with respect to Formula I, the amino acid sequence is according to anyone of Formulas I-Ia, IIa-IIc, IIIa-IIIc, IVa-IVc, VIa-VId, VIIa-VIII, VIIIa-VIIII, XIIa-XIIc, XIIIa-XIIIc, XIVa-XIVc, XVIa-XVId, XVIIa-XVIII, or XVIIIa-XVIIII.

In one embodiment, the linker is Lys. In another embodiment, the linker is -Lys-DIG-Lys-. In another embodiment, the linker is D-Lys. In another embodiment, the linker is -D-Lys-DIG-D-Lys.

In certain embodiments of an opioid agonist peptide dimer, the peptide dimer is according to Formula D-IIa or D-IIb:

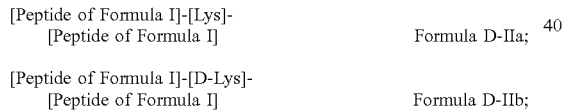

wherein the peptide of Formula I and the linker are as described herein.

In certain embodiments of an opioid agonist peptide dimer, the peptide dimer is according to Formula D-IIIa or D-IIIb:

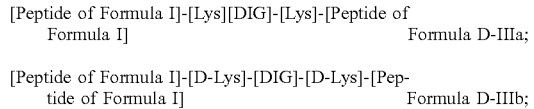

wherein the peptide of Formula I and the linker are as described herein; and DIG is diglycolic acid or —C(O)—CH₂—O—CH₂—C(O)—; and wherein —C(O)— of DIG is attached to N$^\epsilon$ of Lys or D-Lys.

In particular embodiments of an opioid agonist peptide dimer or pharmaceutically acceptable salt or solvate thereof comprising peptide monomers of Formula I, one or more of Y4, Y5 and/or Y6 are present in the peptide monomers, and either Y4, Y5 or Y6 is the C-terminal amino acid of the peptide monomers. In particular embodiments, the C-terminal amino acid residue of each peptide monomer an amino acid comprising an amine side chain, or is selected from the group consisting of: Sar, Lys, D-Lys, N(Me)-Lys, D-N(Me)-Lys, Orn, Dab, Dap, HomoLys, D-Dap, D-Dab, D-Orn, Asp, Glu, D-Asp, D-Glu, HomoSer, HomoGlu, D-homoGlu, N(Me)-Glu, N(Me)-Asp, N(Me)-D-Glu, and N(Me)-D-Asp.

In certain embodiments of an opioid agonist peptide dimer or pharmaceutically acceptable salt or solvate thereof comprising peptide monomers of Formula I, the C-terminus of each peptide monomer is connected by the linker moiety, and X5 is Sarcosine N(Me)Nle, N(Me)Val, N(Me)Leu, N(Me)Phe, N(Me)Tyr and N(Me)Phg.

In certain embodiment, the opioid peptide or each of the peptide monomers of an opioid peptide dimer comprise less than 10 amino acids.

In certain embodiments of any of the opioid peptides and opioid peptide dimers disclosed herein, the opioid peptide or the opioid peptide dimer comprises at least one non-natural amino acid.

In particular embodiments, the opioid agonist peptide or opioid peptide dimer is a dual agonist of both the mu opioid receptor and the delta opioid receptor, a selective agonist of the mu opioid receptor, or a selective agonist of the delta opioid receptor.

In particular embodiments of opioid agonist peptides and opioid agonist peptide dimers of Formula I, X5 is a hydrophobic amino acid.

In particular embodiments of opioid agonist peptides and opioid agonist peptide dimers of Formula I, X4 has a structure as follows:

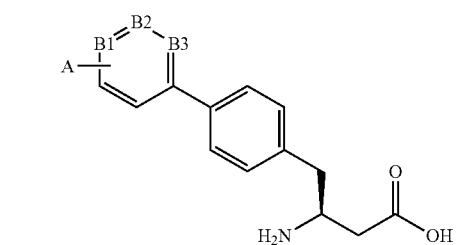

A = Alkyl, CF3, OH, halide in position 1-3

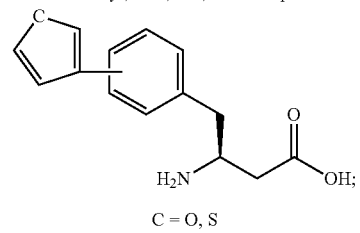

C = O, S and wherein each of B1, B2, and B3 is independently CH or N.

In particular embodiments, opioid agonist peptides comprise fifteen or less, twelve or less, eleven or less, ten or less, nine or less, eight or less, seven or less, six or less or five or less contiguous amino acids. In particular embodiments, each of the monomers present in an opioid agonist peptide dimer comprises fifteen or less, twelve or less, eleven or less, ten or less, nine or less, eight or less, seven or less, six or less or five or less contiguous amino acids. In particular embodiments, opioid agonist peptides comprise four, five, six, seven, eight, nine, ten or eleven contiguous amino acid residues, or each of the monomers present in an opioid agonist peptide dimer comprises four, five, six, seven, eight, nine, ten or eleven contiguous amino acid residues. In particular embodiments, an opioid peptide agonist comprises four to eleven contiguous amino acids, five to ten contiguous amino acids or five to eight contiguous amino acids, or each monomer of an opioid peptide agonist dimer comprises four to eleven contiguous amino acids, five to ten contiguous amino acids or five to eight contiguous amino acids.

Illustrative examples of opioid agonist peptides include any of the peptides depicted in the Examples, as well as any peptides comprising any of the amino acid sequences depicted in the Examples. These include both monomers, and also opioid peptide dimers comprising two peptide monomers, each comprising or consisting of an amino acid sequence disclosed herein or depicted in the Examples. Any of these illustrative peptide sequences may further comprise one or more conjugated linkers and/or other chemical constituents, such as any of the half-life extension moieties described herein.

In particular embodiments, the present invention includes any of the formulas or genuses of opioid agonist peptides disclosed herein with the proviso that the genus does not include or encompass any of the following: (i) enkephalins including either the sequence Tyr-Gly-Gly-Phe-Leu or Tyr-Gly-Gly-Phe-Met; (ii) the opioid peptides known as DADLE (Tyr-D-Ala-Gly-Phe-D-Leu) or DAMGO (Tyr-Gly-N(Me)-Phe-Gly); or (iii) opioid peptides disclosed in U.S. Patent Application Publication No. US 2008/0019913. In particular embodiments of any of the genuses of opioid agonist peptides disclosed here, X5 is not Leu, Met, or (D)Leu.

Examples of substituted β-homo-Phe include, but are not limited to: β-homo-Phe(2-F); β-homo-Phe(3-F); β-homo-Phe(4-F); β-homo-Phe(2-Me); β-homo-Phe(3-Me); β-homo-Phe(4-Me); β-homo-Phe(4-NO₂); β-homo-Phe(4-OH); β-homo-Phe(3-Cl); β-homo-Phe(2-Br); β-homo-Phe(4-I); and βhTrp.

In one embodiment, with respect to Formula I, Y1-Y6 are absent, X1 is DMT; and wherein DMT is 2,6-dimethyltyrosine. In another embodiment, X1 is Phe analog. In one embodiment, the Phe analog is Phe(4-COX); and Phe(4-COX) is substituted or unsubstituted

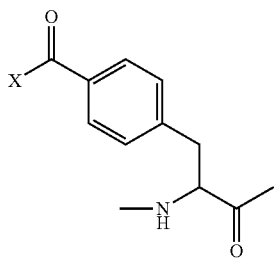

wherein X is substituted or unsubstituted OH or NH₂ (i.e., substituted or unsubstituted hydroxy or amino). In one embodiment, X is unsubstituted OH or NH₂. In another embodiment, X is OH or NH₂ substituted with alkyl or acyl. In a yet another embodiment, X is OH or NH₂ substituted with Me or Ac.

In one embodiment, with respect to Formula I, Y1-Y6 are absent, and X4 is substituted or unsubstituted Phe. In another embodiment, X4 is substituted or unsubstituted bhF or b-homoPhe. In yet another embodiment, X4 is N-methylamino acid. In one embodiment, when X4 is N-methylamino acid; then X2 is Tic, (D)Tic, Ala, (D)Ala, Asp, (D)Asp, Thr, (D)Thr, Glu, or (D)Glu. In another embodiment, when X4 is substituted or unsubstituted Phe; then X5 is N-methylamino acid, or Gly In one embodiment, with respect to Formula I, Y1-Y6 are absent, and X1 is Tyr, X4 is bhF, and X5 is N-methylamino acid.

In one embodiment, with respect to Formula I, the amino acid sequence is according to Formula IIa, IIb, or IIc

```
                                    (SEQ ID NO: 340)
DMT-X2-X3-X4-X5  (Formula IIa);

(SEQ ID NO: 341)
Phe(4-COX)-X2-X3-X4-X5  (Formula IIb);
or (SEQ ID NO: 342)
Tyr-X2-X3-X4-X5  (Formula IIc);
``` wherein DMT is 2,6-dimethyltyrosine; Phe(4-COX) is substituted or unsubstituted

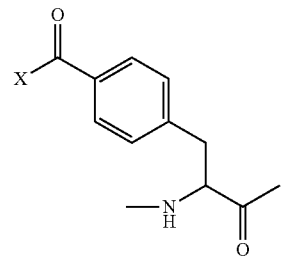

wherein X is substituted or unsubstituted OH or NH₂; each of X2 and X3 is independently any amino acid; X4 is substituted or unsubstituted Phe, substituted or unsubstituted bhF or b-homoPhe, or any N-methylamino acid and X5 is absent, any amino acid or any N-methylamino acid;
provided that:
when the peptide is according to Formula IIa, and X4 is N-methylamino acid; then X2 is Tic, (D)Tic, Ala, (D)Ala, Asp, (D)Asp, Thr, (D)Thr, Glu, or (D)Glu;
when the peptide is according to Formula IIa, and X4 is substituted or unsubstituted Phe; then X5 is N-methylamino acid, or Gly; and
when the peptide is according to Formula IIc; then X4 is bhF and X5 is N-methylamino acid.

In one embodiment, X5 is absent. In another embodiment, X5 is any amino acid. In a particular embodiment, X5 is N-methylamino acid.

In one embodiment, with respect to Formulas IIa-IIc, X4 is Sar.

In one embodiment, with respect to Formulas IIa-IIc, X4 is bhF unsubstituted or substituted with 2-Me, 3-Me, 4-Me, 2-F, 3-F, 4-F, 2-Cl, 3-Cl, 4-Cl, 2-OH, 3-OH, or 4-OH.

In one embodiment, with respect to Formulas IIa-IIc, X4 is unsubstituted bhF.

In one embodiment, with respect to Formula I, the amino acid sequence is according to Formula IIIa, IIIb, or IIIc:

```
                                    (SEQ ID NO: 343)
DMT-X2-X3-bhF-X5  (Formula IIIa);

(SEQ ID NO: 344)
Phe(4-COX)-X2-X3-bhF-X5  (Formula IIIb);
or (SEQ ID NO: 345)
Tyr-X2-X3-bhF-X5  (Formula IIIc);
``` wherein DMT, Phe(4-COX), bhF, X2, X3, and X5 are as described for Formulas IIa-IIc; provided that when the peptide is according to Formula IIIc, then X5 is N-methyl-amino acid.

In one embodiment, Phe(4-COX) is Phe(4-CONH$_2$) or Phe(2,6-dimethyl-4-CONH$_2$) [Phe(DMC)].

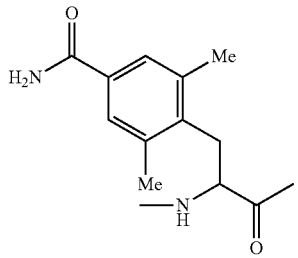 [SMILES: CNC(Cc1c(C)cc(C(N)=O)cc1C)C(C)=O]

Phe(2,6-dimethyl-4-CONH$_2$) or Phe(DMC)

In another embodiment, Phe(4-COX) is Phe(DMC).

In one embodiment, with respect to Formula IIa-IIIc, X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or Ala.

In one embodiment, with respect to Formula IIa-IIc, X3 is G, or β-homo-Phe. In a particular embodiment, X3 is G.

In one embodiment, with respect to Formula I, the amino acid sequence is according to Formula IVa, IVb, or IVc:

```
                                        (SEQ ID NO: 346)
    DMT-X2-G-bhF-X5 (Formula IVa);

(SEQ ID NO: 347)
    Phe(DMC)-X2-G-bhF-X5 (Formula IVb);
    or (SEQ ID NO: 348)
    Tyr-X2-G-bhF-X5 (Formula IVc);
``` wherein DMT, bhF, X2, and X5 are as described for Formula IIa-IIc; Phe(DMC) is as described herein.

In one embodiment, with respect to Formulas IIa-IVc, X2 is (D)Glu, (D)Arg, N(Me)-(D)Ala, (D)Ala, (D)Tic, (D)Lys, (D)Orn, (D)Thr, (D)Asp, or (D)Tyr. In a particular embodiment, X2 is (D)Ala, (D)Thr, (D)Asp, or (D)Glu.

In one embodiment, with respect to Formula I, the amino acid sequence is according to Formula Va, Vb, Vc, or Vd:

```
                                        (SEQ ID NO: 349)
    DMT-(D)Ala-G-bhF-X5 (Formula Va);

(SEQ ID NO: 350)
    DMT-(D)Asp-G-bhF-X5 (Formula Vb);

(SEQ ID NO: 351)
    DMT-(D)Thr-G-bhF-X5 (Formula Vc);

(SEQ ID NO: 352)
    DMT-(D)Glu-G-bhF-X5 (Formula Vd);
``` wherein DMT, and X5 are as described for Formulas IIa-IIc.

In one embodiment, with respect to Formula I, the amino acid sequence is according to formula VIa, VIb, VIc, or VId:

```
    (Formula VIa)
                                        (SEQ ID NO: 353)
    Phe(DMC)-(D)Ala-G-bhF-X5;

(Formula VIb)
                                        (SEQ ID NO: 354)
    Phe(DMC)-(D)Asp-G-bhF-X5;

(Formula VIc)
                                        (SEQ ID NO: 355)
    Phe(DMC)-(D)Thr-G-bhF-X5;

(Formula VId)
                                        (SEQ ID NO: 356)
    Phe(DMC)-(D)Glu-G-bhF-X5;
``` wherein X5 is as described for Formula IIa-IIc; and Phe(DMC) is as described herein.

In one embodiment, with respect to Formulas IIa-VId, X5 is (D)Glu, (D)Arg, N(Me)-(D)Ala, (D)Ala, (D)Tic, (D)Lys, (D)Orn, (D)Thr, (D)Asp, or (D)Tyr. In another embodiment, X5 is Sar, N(Me)Phg, N(Me)Cha, N(Me)Tyr, N(Me)Nle, N(Me)Ile, N(Me)Ala, N(Me)Val, N(Me)Leu, N(Me)Phe. In a particular embodiment, X5 is Sar, N(Me)Phg, N(Me)Ile, N(Me)Ala, N(Me)Val, or N(Me)Leu.

In one embodiment, with respect to Formula I, the amino acid sequence is according to Formula VIIa, VIIb, VIIc, VIId, VIIe, VIIf, VIIg, VIIh, VIIi, VIIj, VIIk, or VIII:

```
    (Formula VIIa)
                                        (SEQ ID NO: 43)
    DMT-(D)Ala-G-bhF-Sar;

(Formula VIIb)
                                        (SEQ ID NO: 83)
    DMT-(D)Asp-G-bhF-Sar;

(Formula VIIc)
                                        (SEQ ID NO: 82)
    DMT-(D)Thr-G-bhF-Sar;

(Formula VIId)
                                        (SEQ ID NO: 187)
    DMT-(D)Glu-G-bhF-Sar;

(Formula VIIe)
                                        (SEQ ID NO: 111)
    DMT-(D)Ala-G-bhF-NMeAla;

(Formula VIIf)
                                        (SEQ ID NO: 170)
    DMT-(D)Asp-G-bhF-NMeAla;

(Formula VIIg)
                                        (SEQ ID NO: 183)
    DMT-(D)Thr-G-bhF-NMeAla;

(Formula VIIh)
                                        (SEQ ID NO: 185)
    DMT-(D)Glu-G-bhF-NMeAla;

(Formula VIIi)
                                        (SEQ ID NO: 113)
    DMT-(D)Ala-G-bhF-NMeIle;

(Formula VIIj)
                                        (SEQ ID NO: 172)
    DMT-(D)Asp-G-bhF-NMeIle;

(Formula VIIk)
                                        (SEQ ID NO: 182)
    DMT-(D)Thr-G-bhF-NMeIle;
    or (Formula VIII)
                                        (SEQ ID NO: 186)
    DMT-(D)Glu-G-bhF-NMeIle;
``` wherein DMT is as described herein.

In one embodiment, with respect to Formula I, the amino acid sequence is according to Formulas VIIIa, VIIIb, VIIIc, VIIId, VIIIe, VIIIf, VIIIg, VIIIh, VIIIi, VIIIj, VIIIk, or VIIIl:

```
(Formula VIIIa)
                                    (SEQ ID NO: 70)
Phe(DMC)-(D)Ala-G-bhF-Sar;

(Formula VIIIb)
                                    (SEQ ID NO: 77)
Phe(DMC)-(D)Asp-G-bhF-Sar;

(Formula VIIIc)
                                    (SEQ ID NO: 76)
Phe(DMC)-(D)Thr-G-bhF-Sar;

(Formula VIIId)
                                    (SEQ ID NO: 330)
Phe(DMC)-(D)Glu-G-bhF-Sar;

(Formula VIIIe)
                                    (SEQ ID NO: 217)
Phe(DMC)-(D)Ala-G-bhF-NMeAla;

(Formula VIIIf)
                                    (SEQ ID NO: 331)
Phe(DMC)-(D)Asp-G-bhF-NMeAla;

(Formula VIIIg)
                                    (SEQ ID NO: 332)
Phe(DMC)-(D)Thr-G-bhF-NMeAla;

(Formula VIIIh)
                                    (SEQ ID NO: 333)
Phe(DMC)-(D)Glu-G-bhF-NMeAla;

(Formula VIIIi)
                                    (SEQ ID NO: 218)
Phe(DMC)-(D)Ala-G-bhF-NMeIle;

(Formula VIIIj)
                                    (SEQ ID NO: 334)
Phe(DMC)-(D)Asp-G-bhF-NMeIle;

(Formula VIIIk)
                                    (SEQ ID NO: 335)
Phe(DMC)-(D)Thr-G-bhF-NMeIle;
or (Formula VIIIl)
                                    (SEQ ID NO: 336)
Phe(DMC)-(D)Glu-G-bhF-NMeIle;
``` wherein Phe(DMC) is as described herein.

In a particular aspect, the present invention provides peptides according to Formula XIIa, XIIb, or XIIc:

```
(Formula XIIa)
                                    (SEQ ID NO: 340)
R¹-DMT-X2-X3-X4-X5-R²;

(Formula XIIb)
                                    (SEQ ID NO: 341)
R¹-Phe(4-COX)-X2-X3-X4-X5-R²;
or (Formula XIIc)
                                    (SEQ ID NO: 342)
R¹-Tyr-X2-X3-X4-X5-R²,
``` or pharmaceutically acceptable salt or solvate thereof;

wherein $R^1$ is H or acetyl; $R^2$ is OH or $NH_2$; DMT is 2,6-dimethyltyrosine; Phe(4-COX) is substituted or unsubstituted

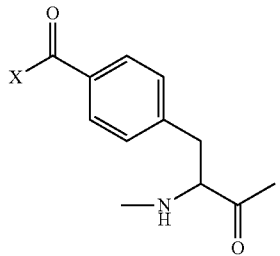

wherein X is substituted or unsubstituted OH or $NH_2$;
each of X2 and X3 is independently any amino acid; X4 is substituted or unsubstituted bhF or b-homoPhe, or any N-methylamino acid; and X5 is absent, any amino acid or any N-methylamino acid;
provided that:
when the peptide is according to formula XIIa, X4 is N-methylamino acid; then X2 is Tic, (D)Tic, Ala, (D)Ala, Asp, (D)Asp, Thr, (D)Thr, Glu, or (D)Glu; and
when the peptide is according to Formula XIIc; then X4 is bhF and X5 is N-methylamino acid.

In one embodiment, X5 is any amino acid. In another embodiment, X5 is any N-methylamino acid.

In one embodiment, with respect to Formulas XIIa-XIIc, X4 is Sar.

In one embodiment, with respect to Formulas XIIa-XIIc, X4 is bhF unsubstituted or substituted with 2-Me, 3-Me, 4-Me, 2-F, 3-F, 4-F, 2-Cl, 3-Cl, 4-Cl, 2-OH, 3-OH, or 4-OH. In a particular embodiment, X4 is unsubstituted bhF.

In one embodiment, with respect to Formulas XIIa-XIIc, the peptide is according to Formula XIIIa, XIIIb, or XIIIc:

```
(Formula XIIIa)
                                    (SEQ ID NO: 343)
R¹-DMT-X2-X3-bhF-X5-R²;

(Formula XIIIb)
                                    (SEQ ID NO: 344)
R¹-Phe(4-COX)-X2-X3-bhF-X5-R²;
or (Formula XIIIc)
                                    (SEQ ID NO: 345)
R¹-Tyr-X2-X3-bhF-X5-R²;
``` wherein $R^1$, $R^2$, DMT, Phe(4-COX), bhF, X2, X3, and X5 are as described herein;
provided that when the peptide is according to Formula XIIIc, then X5 is N-methylamino acid.

In one embodiment, Phe(4-COX) is Phe(4-CONH$_2$) or Phe(2,6-dimethyl-4-CONH$_2$) [Phe(DMC)]

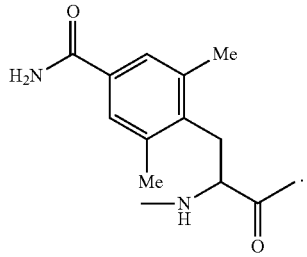

Phe(2,6-dimethyl-4-CONH$_2$) or Phe(DMC)

In another embodiment, Phe(4-COX) is Phe(DMC).

In one embodiment, with respect to Formula XIIa-XIIIc, X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or Ala. In another embodiment, X3 is G, or bhPhe. In a particular embodiment, X3 is G.

In one embodiment, with respect to Formulas XIIa-XIIc, the peptide is according to Formula XIVa, XIVb, or XIVc:

```
                                            (Formula XIVa)
                                         (SEQ ID NO: 346)
R¹-DMT-X2-G-bhF-X5-R²;

(Formula XIVb)
                                         (SEQ ID NO: 347)
R¹-Phe(DMC)-X2-G-bhF-X5-R²;
or (Formula XIVc)
                                         (SEQ ID NO: 348)
R¹-Tyr-X2-G-bhF-X5-R²;
``` wherein $R^1$, $R^2$, DMT, bhF, X2, and X5 are as described for Formulas XIIa-XIIc; and
Phe(DMC) is as described herein.

In one embodiment, with respect to Formulas XIIa-XIVc, the peptide is according to formula X2 is (D)Glu, (D)Arg, N(Me)-(D)Ala, (D)Ala, (D)Tic, (D)Lys, (D)Orn, (D)Thr, (D)Asp, or (D)Tyr. In a particular embodiment, X2 is (D)Ala, (D)Thr, (D)Asp, or (D)Glu.

In one embodiment, with respect to Formulas XIIa-XIIc, the peptide is according to Formula XVa, XVb, XVc, or XVd:

```
                                            (Formula XVa)
                                         (SEQ ID NO: 349)
R¹-DMT-(D)Ala-G-bhF-X5-R²;

(Formula XVb)
                                         (SEQ ID NO: 350)
R¹-DMT-(D)Asp-G-bhF-X5-R²;

(Formula XVc)
                                         (SEQ ID NO: 351)
R¹-DMT-(D)Thr-G-bhF-X5-R²;

(Formula XVd)
                                         (SEQ ID NO: 352)
R¹-DMT-(D)Glu-G-bhF-X5-R²;
``` wherein $R^1$, $R^2$, DMT, and X5 are as described for formula XIIa-XIIc.

In one embodiment, with respect to Formulas XIIa-XIIc, the peptide is according to Formula XVIa, XVIb, XVIc, or XVId:

```
                                            (Formula XVIa)
                                         (SEQ ID NO: 353)
R¹-Phe(DMC)-(D)Ala-G-bhF-X5-R²;

(Formula XVIb)
                                         (SEQ ID NO: 354)
R¹-Phe(DMC)-(D)Asp-G-bhF-X5-R²;

(Formula XVIc)
                                         (SEQ ID NO: 355)
R¹-Phe(DMC)-(D)Thr-G-bhF-X5-R²;

(Formula XVId)
                                         (SEQ ID NO: 356)
R¹-Phe(DMC)-(D)Glu-G-bhF-X5-R²;
``` wherein $R^1$, $R^2$, X5 are as described for formula XIIa-XIIc; and Phe(DMC) is as described herein.

In another embodiment, with respect to Formulas XIIa-XVId, X5 is (D)Glu, (D)Arg, N(Me)-(D)Ala, (D)Ala, (D)Tic, (D)Lys, (D)Orn, (D)Thr, (D)Asp, or (D)Tyr. In another embodiment, X5 is Sar, N(Me)Phg, N(Me)Cha, N(Me)Tyr, N(Me)Nle, N(Me)Ile, N(Me)Ala, N(Me)Val, N(Me)Leu, N(Me)Phe. In a particular embodiment, X5 is Sar, N(Me)Phg, N(Me)Ile, N(Me)Ala, N(Me)Val, or N(Me)Leu.

In another embodiment, with respect to Formulas IIa-VId, and XIIa-XVId, X5 is N-alkylamino acid. In one embodiment, N-alkylamino acid is $N(C_1$-$C_8)$alkyl amino acid. In another embodiment, N-alkylamino acid is $N(C_1$-$C_4)$alkyl amino acid. In yet another embodiment, N-alkylamino acid is N-Me, N-Et, N-(n-Pr), N-(i-Pr), or N-(t-Bu) amino acid. In a particular embodiment, N-alkylamino acid is N-methylamino acid.

In one embodiment, with respect to Formulas XIIa-XIIc, the peptide is according to Formula XVIIa, XVIIb, XVIIc, XVIId, XVIIe, XVIIf, XVIIg, XVIIh, XVIIi, XVIIj, XVIIk, or XVIII:

```
                                            (Formula XVIIa)
                                          (SEQ ID NO: 43)
R¹-DMT-(D)Ala-G-bhF-Sar-R²;

(Formula XVIIb)
                                          (SEQ ID NO: 83)
R¹-DMT-(D)Asp-G-bhF-Sar-R²;

(Formula XVIIc)
                                          (SEQ ID NO: 82)
R¹-DMT-(D)Thr-G-bhF-Sar-R²;

(Formula XVIId)
                                         (SEQ ID NO: 187)
R¹-DMT-(D)Glu-G-bhF-Sar-R²;

(Formula XVIIe)
                                         (SEQ ID NO: 111)
R¹-DMT-(D)Ala-G-bhF-NMeAla-R²;

(Formula XVIIf)
                                         (SEQ ID NO: 170)
R¹-DMT-(D)Asp-G-bhF-NMeAla-R²;

(Formula XVIIg)
                                         (SEQ ID NO: 183)
R¹-DMT-(D)Thr-G-bhF-NMeAla-R²;

(Formula XVIIh)
                                         (SEQ ID NO: 185)
R¹-DMT-(D)Glu-G-bhF-NMeAla-R²;

(Formula XVIIi)
                                         (SEQ ID NO: 113)
R¹-DMT-(D)Ala-G-bhF-NMeIle-R²;

(Formula XVIIj)
                                         (SEQ ID NO: 172)
R¹-DMT-(D)Asp-G-bhF-NMeIle-R²;

(Formula XVIIk)
                                         (SEQ ID NO: 182)
R¹-DMT-(D)Thr-G-bhF-NMeIle-R²;
or (Formula XVIII)
                                         (SEQ ID NO: 186)
R¹-DMT-(D)Glu-G-bhF-NMeIle-R²;
``` wherein $R^1$, $R^2$, DMT are as described for Formulas XIIa-XIIc.

In one embodiment, with respect to Formulas XIIa-XIIc, the peptide is according to Formula XVIIIa, XVIIIb, XVIIIc, XVIIId, XVIIIe, XVIIIf, XVIIIg, XVIIIh, XVIIIi, XVIIIj, XVIIIk, or XVIIII:

```
                                              (Formula XVIIIa)
                                              (SEQ ID NO: 70)
R¹-Phe(DMC)-(D)Ala-G-bhF-Sar-R²;

(Formula XVIIIb)
                                              (SEQ ID NO: 77)
R¹-Phe(DMC)-(D)Asp-G-bhF-Sar-R²;

(Formula XVIIIc)
                                              (SEQ ID NO: 76)
R¹-Phe(DMC)-(D)Thr-G-bhF-Sar-R²;

(Formula XVIIId)
                                              (SEQ ID NO: 330)
R¹-Phe(DMC)-(D)Glu-G-bhF-Sar-R²;

(Formula XVIIIe)
                                              (SEQ ID NO: 217)
R¹-Phe(DMC)-(D)Ala-G-bhF-NMeAla-R²;

(Formula XVIIIf)
                                              (SEQ ID NO: 331)
R¹-Phe(DMC)-(D)Asp-G-bhF-NMeAla-R²;

(Formula XVIIIg)
                                              (SEQ ID NO: 332)
R¹-Phe(DMC)-(D)Thr-G-bhF-NMeAla-R²;

(Formula XVIIIh)
                                              (SEQ ID NO: 333)
R¹-Phe(DMC)-(D)Glu-G-bhF-NMeAla-R²;

(Formula XVIIIi)
                                              (SEQ ID NO: 218)
R¹-Phe(DMC)-(D)Ala-G-bhF-NMeIle-R²;

(Formula XVIIIj)
                                              (SEQ ID NO: 334)
R¹-Phe(DMC)-(D)Asp-G-bhF-NMeIle-R²;

(Formula XVIIIk)
                                              (SEQ ID NO: 335)
R¹-Phe(DMC)-(D)Thr-G-bhF-NMeIle-R²;
or (Formula XVIIIl)
                                              (SEQ ID NO: 336)
R¹-Phe(DMC)-(D)Glu-G-bhF-NMeIle-R²;
``` wherein R¹, R², and Phe(DMC) are as described for Formulas XIIa-XIIc.

In one embodiment, R¹ is acetyl. In a particular embodiment, R¹ is H.

In one embodiment, R² is OH. In anther embodiment, R² is NH$_2$.

In certain embodiments of the opioid agonist peptide or pharmaceutically acceptable salt or solvate thereof of Formula I-XVIIIl comprises or consists of the following sequences:

```
                                              (SEQ ID NO: 37)
H-DMT-a-G-F-nLeu-NH₂;

(SEQ ID NO: 38)
H-DMT-a-G-Phe(4-F)-G-NH₂;

(SEQ ID NO: 39)
H-DMT-a-G-Phe(4-CN)-G-NH₂;

(SEQ ID NO: 41)
H-DMT-a-G-Phe(3,4-diCl)-G-NH₂;

(SEQ ID NO: 42)
H-DMT-a-G-F-Sar-NH₂;

(SEQ ID NO: 43)
H-DMT-a-G-bhF-Sar-NH₂;

(SEQ ID NO: 45)
H-DMT-dTic-G-F-Sar-NH₂;

(SEQ ID NO: 60)
H-Phe(4-CONH₂)-a-G-bhF-Sar-NH₂;

(SEQ ID NO: 70)
H-Phe(2,6-dimethyl-4-CONH₂)-a-G-bhF-Sar-NH₂;

(SEQ ID NO: 72)
H-DMT-a-Aib-bhF-Sar-NH₂;

(SEQ ID NO: 74)
H-Phe(2,6-dimethyl-4-CONH₂)-G-G-bhF-Sar-NH₂;

(SEQ ID NO: 76)
H-Phe(2,6-dimethyl-4-CONH₂)-D-Thr-G-bhF-Sar-NH₂;

(SEQ ID NO: 77)
H-Phe(2,6-dimethyl-4-CONH₂)-D-Asp-G-bhF-Sar-NH₂;

(SEQ ID NO: 70)
H-Phe(2,6-dimethyl-4-CONH₂)-a-G-bhF-Sar-OH;

(SEQ ID NO: 81)
H-DMT-G-G-bhF-Sar-NH₂;

(SEQ ID NO: 82)
H-DMT-(D)Thr-G-bhF-Sar-NH₂;

(SEQ ID NO: 83)
H-DMT-(D)Asp-G-bhF-Sar-NH₂;

(SEQ ID NO: 84)
H-DMT-(D)Tyr-G-bhF-Sar-NH₂;

(SEQ ID NO: 85)
H-Phe(2,6-dimethyl-4-CONH₂)-(D)Tyr-G-bhF-Sar-NH₂;

(SEQ ID NO: 43)
H-DMT-a-G-bhF-Sar-OH;

(SEQ ID NO: 93)
H-Phe(2,6-dimethyl-4-CONH₂)-a-G-bhF-N(Me)Ala-OH;

(SEQ ID NO: 94)
H-Phe(2,6-dimethyl-4-CONH₂)-a-G-bhF-Gly-NH₂;

(SEQ ID NO: 96)
H-Phe(2,6-dimethyl-4-CONH₂)-a-G-bhF-N(Me)Val-OH;

(SEQ ID NO: 97)
H-Phe(2,6-dimethyl-4-CONH₂)-a-G-bhF-N(Me)Nva-OH;

(SEQ ID NO: 99)
H-Phe(2,6-dimethyl-4-CONH₂)-a-G-bhF-N(Me)Phg-OH;

(SEQ ID NO: 102)
H-Phe(2,6-dimethyl-4-CONH₂)-a-G-bhF-N(Me)Tyr-OH;

(SEQ ID NO: 111)
H-DMT-a-G-bhF-N(Me)Ala-OH;

(SEQ ID NO: 112)
H-DMT-a-G-bhF-Gly-OH;

(SEQ ID NO: 112)
H-DMT-a-G-bhF-Gly-NH₂;

(SEQ ID NO: 113)
H-DMT-a-G-bhF-N(Me)ILe-OH;

(SEQ ID NO: 116)
H-DMT-a-G-bhF-N(isopentyl)Gly-NH₂;

(SEQ ID NO: 117)
H-DMT-a-G-bhF-N(3-isopropyloxypropyl)Gly-NH₂;

(SEQ ID NO: 118)
H-DMT-a-G-bhF-N(benzyl)Gly-NH₂;
```

H-DMT-a-G-bhF-N(3-propionic acid)Gly-NH₂; (SEQ ID NO: 120)

H-DMT-a-G-bhF-N(Phenethyl)Gly-NH₂; (SEQ ID NO: 121)

H-DMT-a-G-bhF-N(Trifluoroethyl)Gly-NH₂; (SEQ ID NO: 122)

H-DMT-a-G-bhF-N(Cyclohexyl)Gly-NH₂; (SEQ ID NO: 123)

H-DMT-a-G-bhF-N(amyl)Gly-NH₂; (SEQ ID NO: 124)

H-DMT-a-G-(D)N(Me)Phe-N(Me)Nle-NH₂; (SEQ ID NO: 154)

H-DMT-a-G-bhF-N(Me)-Leu-NH₂; (SEQ ID NO: 155)

H-DMT-a-G-bhF-N(Me)-Cha-NH₂; (SEQ ID NO: 156)

H-DMT-a-G-bhF-N(Me)-Phg-NH₂; (SEQ ID NO: 157)

H-DMT-a-G-bhF-N(Me)-Phe-NH₂; (SEQ ID NO: 158)

H-DMT-a-G-bhF-N(Me)-Nle-NH₂; (SEQ ID NO: 159)

H-DMT-a-G-bhF-N(Me)-Tyr-NH₂; (SEQ ID NO: 160)

H-DMT-a-G-bhF-N(Me)-Val-NH₂; (SEQ ID NO: 161)

H-DMT-a-G-bhF-N(Me)-Leu-OH; (SEQ ID NO: 155)

H-DMT-a-G-bhF-N(Me)-Cha-OH; (SEQ ID NO: 156)

H-DMT-a-G-bhF-N(Me)-Phg-OH; (SEQ ID NO: 157)

H-DMT-a-G-bhF-N(Me)-Phe-OH; (SEQ ID NO: 158)

H-DMT-a-G-bhF-N(Me)-Nle-OH; (SEQ ID NO: 159)

H-DMT-a-G-bhF-N(Me)-Tyr-OH; (SEQ ID NO: 160)

H-DMT-a-G-bhF-N(Me)-Val-OH; (SEQ ID NO: 161)

H-DMT-a-G-bhF-N(Me)-Nva-OH; (SEQ ID NO: 162)

H-Phe(2,6-dimethyl-4-CONH₂)-a-G-bhF(2-Me)-N(Me)Nle-OH; (SEQ ID NO: 163)

H-Phe(2,6-dimethyl-4-CONH₂)-a-G-bhF(3-Me)-N(Me)Nle-OH; (SEQ ID NO: 164)

H-Phe(2,6-dimethyl-4-CONH₂)-a-G-bhF(4-Me)-N(Me)Nle-OH; (SEQ ID NO: 165)

or

H-Phe(2,6-dimethyl-4-CONH₂)-a-G-bhF(4-F)-N(Me)Nle-OH. (SEQ ID NO: 166)

In certain embodiments of the opioid agonist peptide or pharmaceutically acceptable salt or solvate thereof of Formula I-XVIIII comprises or consists of the following sequences:

H-DMT-a-G-bhF-Sar-NH₂; (SEQ ID NO: 43)

H-DMT-(D)Asp-G-bhF-Sar-NH₂; (SEQ ID NO: 83)

or

H-Phe(2,6-dimethyl-4-CONH₂)-a-G-bhF(4-F)-N(Me)Nle-OH. (SEQ ID NO: 166)

In certain embodiments of the opioid agonist peptide or pharmaceutically acceptable salt or solvate thereof of Formula I-XVIIII comprises or consists of the following sequences:

H-DMT-a-G-bhF-Sar-NH₂; (SEQ ID NO: 43)

H-DMT-a-G-bhF-Sar-OH; (SEQ ID NO: 43)

H-DMT-a-G-bhF-N(Me)Ala-OH; (SEQ ID NO: 111)

H-DMT-(D)Thr-G-bhF-N(Me)Ala-OH; (SEQ ID NO: 183)

H-DMT-(D)Asp-G-bhF-Sar-OH; (SEQ ID NO: 83)

H-DMT-(D)Asp-G-bhF-Sar-NH₂; (SEQ ID NO: 83)

H-Phe(2,6-dimethyl-4-CONH₂)-a-G-bhF-Sar-OH; (SEQ ID NO: 70)

H-Phe(2,6-dimethyl-4-CONH₂)-a-G-bhF-Sar-NH₂; (SEQ ID NO: 70)

H-Phe(2,6-dimethyl-4-CONH₂)-a-G-bhF(4-F)-N(Me)Nle-OH; (SEQ ID NO: 166)

or

H-Phe(2,6-dimethyl-4-CONH₂)-a-G-bhF(4-F)-N(Me)Nle-NH₂. (SEQ ID NO: 166)

In a particular aspect, the present disclosure includes an opioid agonist peptide comprising or consisting of an amino acid sequence of Formula I:

(Formula I)
Y1-Y2-Y3-X1-X2-X3-X4-X5-Y4-Y5-Y6 (SEQ ID NO: 339)

or a pharmaceutically acceptable salt or solvate thereof, wherein:
Y1 is absent or any amino acid;
Y2 is absent or any amino acid;
Y3 is absent or any amino acid;

X1 is Tyr, D-Tyr, a Tyr analog, Tic, a Tic analog, or a Phe analog;
X2 is any amino acid;
X3 is any amino acid;
X4 is any amino acid;
X5 is absent or any amino acid;
Y4 is absent or any amino acid;
Y5 is absent or any amino acid; and
Y6 is absent or any amino acid.

In particular embodiments of peptides or pharmaceutically acceptable salts or solvates thereof of Formula I:
Y1 is absent;
Y2 is absent;
Y3 is absent;
X1 is Tyr, DMT, or Phe(4-COX);
X2 is any amino acid;
X3 is any amino acid;
X4 is Sar or bhF unsubstituted or substituted with 2-Me, 3-Me, 4-Me, 2-F, 3-F, 4-F, 2-Cl, 3-Cl, 4-Cl, 2-OH, 3-OH, or 4-OH;
X5 is absent or any amino acid;
Y4 is absent;
Y5 is absent; and
Y6 is absent;
Wherein DMT is 2,6-dimethyltyrosine; Phe(4-COX) is substituted or unsubstituted

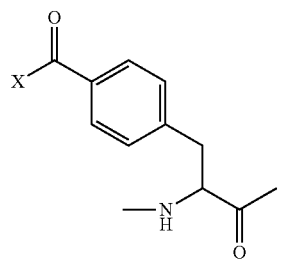

wherein X is substituted or unsubstituted OH or NH$_2$;
optionally provided that when X1 is Tyr; then X4 is bhF and X5 is N-methylamino acid.

In one embodiment, X5 is absent. In another embodiment, X5 is any amino acid. In another embodiment, X5 is an N-Methylamino acid. In another embodiment, X5 is a hydrophobic amino acid. In certain embodiments, X5 is absent, any N-methylamino acid, or X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly. In certain embodiments, X5 is absent, a hydrophobic amino acid, or an amino acid selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, Nle, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly.
In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, N(Me)Nva, Aib, β-Ala, (D)Glu, (D)Asp, β-homoAla, Asn, (D)Asn, N(trifluoroethyl)Gly, N(cyclohexyl)Gly, N(amyl)Gly, N(hexadecyl)Gly, N(3-isopropyloxypropyl)Gly, N(benzyl)Gly, N(cyclohexylmethyl)Gly, N(3-propanoic acid)Gly, N(phenethyl)Gly, 2-Nal, N(octyl)Gly, and N(isopentyl)Gly.
In another embodiment, X5 is selected from Sar, Gly, N(Me)Phg, N(Me)Cha, N(Me)Tyr, N(Me)Nle, N(Me)Ile, N(Me)Ala, N(Me)Val, N(Me)Leu, N(Me)Phe, and N(Me)Nva.

In a particular embodiment, with respect to Formula I, the amino acid sequence is according to Formula XIIIa, XIIIb, or XIIIc;
wherein Formula XIIIa, XIIIb, or XIIIc, DMT, Phe(4-COX), bhF, X2, X3, and X5 are as described herein; R$^1$ is H or acetyl; and R$^2$ is OH or NH$_2$; provided that when the peptide is according to formula XIIIc, then X5 is N-methylamino acid.

In a particular embodiment, X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or Ala.

In a particular embodiment, with respect to Formula I, the amino acid sequence is according to Formula XIVa, XIVb, or XIVc; wherein Formula XIVa, XIVb, or XIVc, and Phe(DMC) are as described herein; and R$^1$ is H or acetyl; and R$^2$ is OH or NH$_2$.

In a particular embodiment, with respect to Formula I, the amino acid sequence is according to X2 is (D)Glu, (D)Arg, N(Me)-(D)Ala, (D)Ala, (D)Tic, (D)Lys, (D)Orn, (D)Thr, (D)Asp, or (D)Tyr.

In a particular embodiment, with respect to Formula I, the amino acid sequence is according to Formula XVa, XVb, or XVc.

In a particular embodiment, X5 is (D)Glu, (D)Arg, N(Me)-(D)Ala, (D)Ala, (D)Tic, (D)Lys, (D)Orn, (D)Thr, (D)Asp, or (D)Tyr, Sar, N(Me)Phg, N(Me)Cha, N(Me)Tyr, N(Me)Nle, N(Me)Ile, N(Me)Ala, N(Me)Val, N(Me)Leu, N(Me)Phe.

In a particular embodiment, with respect to Formula I, the amino acid sequence is according to Formula XVIa, XVIb, XVIc, or XVId In a particular embodiment, with respect to Formula I, the amino acid sequence is according to Formula XVIIa, XVIIb, XVIIc, XVIId, XVIIe, XVIIf, XVIIg, XVIIh, XVIIi, XVIIj, XVIIk, or XVIII.

In a particular embodiment, with respect to Formula I, the amino acid sequence is according to Formula XVIIIa, XVIIIb, XVIIIc, XVIIId, XVIIIe, XVIIIf, XVIIIg, XVIIIh, XVIIIi, XVIIIj, XVIIIk, or XVIIIl.

In a particular embodiment, R$^1$ is H. In another particular embodiment, R$^2$ is OH. In a more particular embodiment, R$^2$ is NH$_2$.

In a more particular embodiment, the peptide sequence is

```
                                        (SEQ ID NO: 43)
        H-DMT-a-G-bhF-Sar-NH2;
    or
                                        (SEQ ID NO: 43)
        H-DMT-a-G-bhF-Sar-OH.
```

In a more particular embodiment, the peptide sequence is

```
                                        (SEQ ID NO: 111)
        H-DMT-a-G-bhF-N(Me)Ala-OH;
    or
```

```
                                                     (SEQ ID NO: 183)
             H-DMT-(D)Thr-G-bhF-N(Me)Ala-OH.
```

In a more particular embodiment, the peptide sequence is

```
                                                      (SEQ ID NO: 83)
             H-DMT-(D)Asp-G-bhF-Sar-OH;
         or
                                                      (SEQ ID NO: 83)
             H-DMT-(D)Asp-G-bhF-Sar-NH2.
```

In a more particular embodiment, the peptide sequence is

```
                                                      (SEQ ID NO: 70)
             H-Phe(2,6-dimethyl-4-CONH2)-a-G-bhF-Sar-OH;
         or
                                                      (SEQ ID NO: 70)
             H-Phe(2,6-dimethyl-4-CONH2)-a-G-bhF-Sar-NH2.
```

In a more particular embodiment, the peptide sequence is

```
                                                     (SEQ ID NO: 166)
H-Phe(2,6-dimethyl-4-CONH2)-a-G-bhF(4-F)-N(Me)Nle-
OH;
or
                                                     (SEQ ID NO: 100)
H-Phe(2,6-dimethyl-4-CONH2)-a-G-bhF(4-F)-N(Me)Nle-
NH2.
```

In a more particular embodiment, the peptide sequence is H-DMT-a-G-bhF-Sar-NH$_2$ (SEQ ID NO:43).

In a more particular embodiment, the peptide sequence is H-DMT-(D)Thr-G-bhF-N(Me)Ala-OH (SEQ ID NO: 183).

In a more particular embodiment, the peptide sequence is H-Phe(2,6-dimethyl-4-CONH$_2$)-a-G-bhF-Sar-NH$_2$ (SEQ ID NO:70).

One of skill in the art will appreciate that certain amino acids and other chemical moieties are modified when bound to another molecule. For example, an amino acid side chain may be modified when it is bound to a linker or other chemical moiety, e.g., one or more hydrogen may be removed or replaced by the bond. Accordingly, as used herein, reference to an amino acid or modified amino acid present in an opioid agonist peptide is meant to include the form of such amino acid or modified amino acid present in the peptide both with or without a bond to a linker or other chemical moiety.

Linkers

Opioid agonist peptides disclosed herein, including both monomers and dimers, may comprise a linker moiety. In particular embodiments, a linker is attached to a C-terminal amino acid of the opioid agonist peptide. In particular embodiments, a linker is attached to an internal amino acid of the opioid agonist peptide. In particular embodiments, a linker is attached to two opioid agonist peptide monomers to form an opioid agonist dimer peptide. In particular embodiments, the linker is attached to the C-terminal amino acid of both monomers present in the dimer. In particular embodiments, the linker is attached to internal amino acids of both monomers present in the dimer.

Any linker known in the art may be used. Linkers connecting monomers may include any structure, length, and/or size that is compatible with the teachings herein. In particular embodiments, an opioid agonist peptide or opioid agonist peptide dimer comprising a peptide of Formula I comprises any of the linkers disclosed herein. In at least one embodiment, a linker moiety is selected from the non-limiting group consisting of cysteine, lysine, DIG, PEG4, PEG4-biotin, PEG13, PEG25, PEG1K, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. In certain embodiments, the linker is a diethylene glycol linker, an iminodiacetic acid (IDA) linker, a β-Ala-iminodiaceticacid (β-Ala-IDA) linker, or a PEG linker. In certain embodiments, the linker comprises or consists of an ethyl, propyl, butyl, etc. Examples of suitable linkers include but are not limited to:

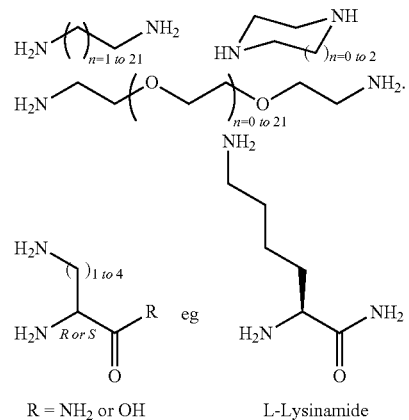

R = NH$_2$ or OH    L-Lysinamide

Non-limiting examples of other suitable linker moieties are provided in Table 2.

TABLE 2

Illustrative Linker Moieties
Linker Moiety

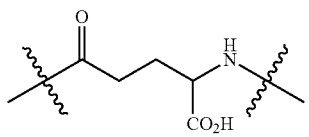

IsoGlu

TABLE 2-continued
Illustrative Linker Moieties
Linker Moiety
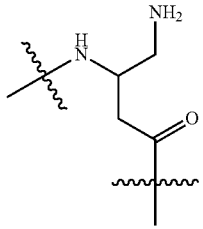 [SMILES: *NC(CN)CC(*)=O]
Dapa
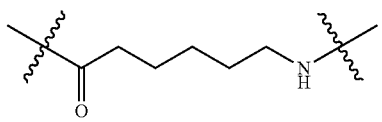 [SMILES: *NCCCCCC(*)=O]
Ahx
Lipidic based linkers:
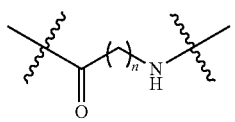
n = 1 to 24
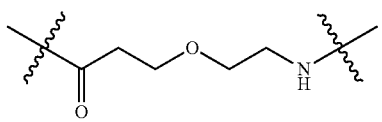 [SMILES: *NCCOCCC(*)=O]
PEG1
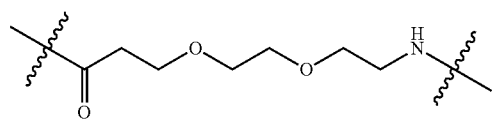 [SMILES: *NCCOCCOCCC(*)=O]
PEG2
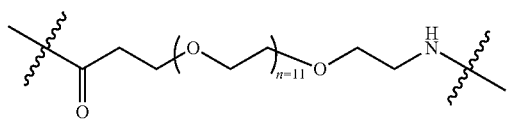
PEG11 (40 atoms) also known as PEG12
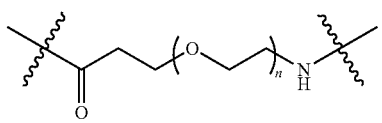
n = 1 to 25
PEG based linkers
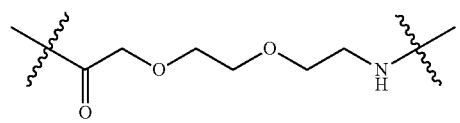 [SMILES: *NCCOCCOCC(*)=O]
OEG TABLE 2-continued Illustrative Linker Moieties
Linker Moiety

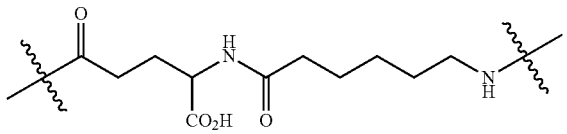 [SMILES: *NCCCCCC(=O)NC(CCC(*)=O)C(=O)O]

IsoGlu-Ahx

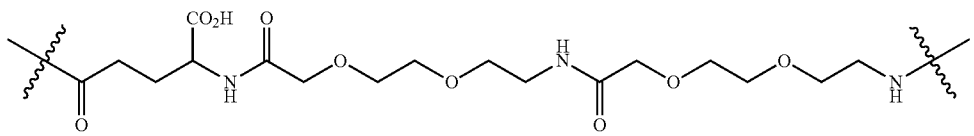 [SMILES: *NCCOCCOCC(=O)NCCOCCOCC(=O)NC(CCC(*)=O)C(=O)O]

IsoGlu-OEG-OEG

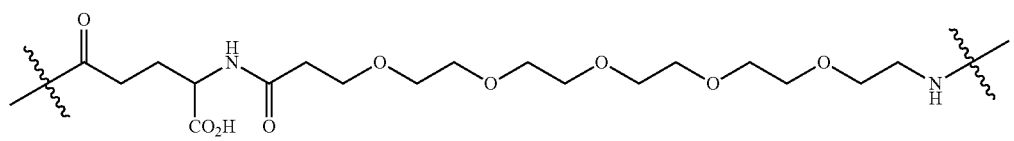 [SMILES: *NCCOCCOCCOCCOCCOCCC(=O)NC(CCC(*)=O)C(=O)O]

IsoGlu-PEG5

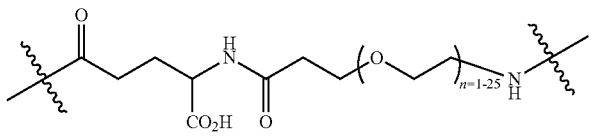

IsoGlu-PEGn

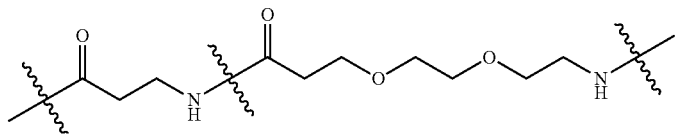

βAla-PEG2

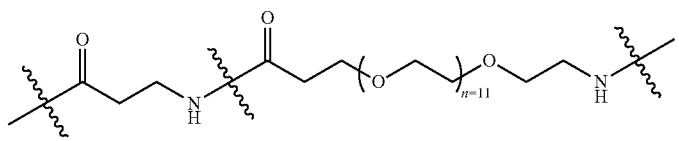

βAla-PEG11 (40 atoms)

In certain embodiments, opioid agonist peptide dimers are linked via a linker conjugated to the C-terminal amino acid residues of the two peptide monomers present in the dimer. In particular embodiments, the C-terminal amino acid residues are selected from: any amino acid with an amine side chain or as the carboxylic acid, Sar, N(Me)Phg, N(Me)Nle, N(Me)Leu, Lys, D-Lys, N(Me) Lys, D-N(Me)Lys, Orn, Dab, Dap, HomoLys, D-Dap, D-Dab, and D-Orn. In particular embodiments, the C-terminal amino acid residue is Y4, Y5 or Y6 of Formula I. In particular embodiments, the C-terminal amino acid residues are selected from: any amino acid with a free amine (e.g., Lys) or is selected from Sar, N(Me)Phg, N(Me)Nle, N(Me)Val, N(Me)Ile, and N(Me)Leu.

In certain embodiments, opioid agonist peptide dimers comprise two peptide monomer subunits that are linked through a linker conjugated to the C-terminal amino acids of the two monomer subunits. In particular embodiments, the C-terminal residues are linked through a linker that comprises or consists of a diamine, for example, ethyl, propyl, butyl, piperazine. In certain embodiments the opioid agonist peptide dimer has a general structure similar or the same as the structure depicted below for one example (SEQ ID NO:43):

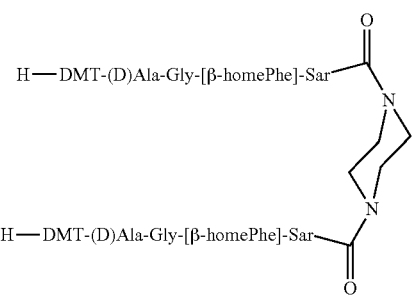

One having skill in the art will appreciate that the linker (e.g., C- and N-terminal linker) moieties disclosed herein are non-limiting examples of suitable, and that any suitable linker moiety may be used. Thus, some embodiments of the present invention comprise a homo- or heterodimer opioid agonist peptide comprised of two monomers selected from the peptides shown in any of tables herein or comprising or consisting of a sequence presented in any of tables herein, wherein the C- or N-termini of the respective monomers (or internal amino acid residues) are linked by any suitable linker moiety to provide an opioid agonist peptide dimer.

Conjugates

In certain embodiments, opioid agonist peptides disclosed herein, including both monomers and dimers, comprise one or more conjugated chemical substituents, such as lipophilic substituents and polymeric moieties, which may be referred to herein as GI restricted moieties. Without wishing to be bound by any particular theory, it is believed that certain conjugated chemical substituents, such as, e.g., a small PEG based substituent, can limit absorption of the opioid agonist peptides through the GI tract. In certain embodiments, the GI restricted moiety is attached to an amino acid residue present in the opioid agonist peptide, e.g., the C-terminal amino acid of the opioid agonist peptide. The GI restricted moiety may be attached to the opioid agonist peptide via a linker, including but not limited to any of those described herein.

The GI restricted moiety is preferably water-soluble (amphiphilic or hydrophilic), non-toxic, and pharmaceutically inert. Suitable GI restricted moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are mono-activated, alkoxy-terminated polyalkylene oxides (POA's) such as mono-methoxy-terminated polyethylene glycols (mPEG's); bis activated polyethylene oxides (glycols) or other PEG derivatives. Other suitable GI restricted moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73: 721-729. The GI restricted moiety may be straight-chain or branched. In some embodiments, it has a molecular weight of 500-40,000 Da, for example 500-10,000 Da, 1000-5000 Da, 10,000-20,000 Da, or 20,000-40,000 Da. In particular embodiments, suitable polymers will vary substantially by weights ranging from about 200 Da to about 40 KDa, e.g., 200 Da to about 10,000 Da or from about 200 Da to about 4,000 Da are usually selected for the purposes of the present invention.

In certain embodiments, a GI restricted moiety is a PEG moiety. As used herein, "Polyethylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 10,000 Da or less than 20,000 Da, PEO to polymers with a molecular mass above 20,000 Da, and POE to a polymer of any molecular mass. PEG and PEO are liquids or low-melting solids, depending on their molecular weights. While PEG and PEO with different molecular weights find use in different applications, and have different physical properties (e.g. viscosity) due to chain length effects, their chemical properties are nearly identical. Throughout this disclosure, the three names are used indistinguishably.

PEGs are prepared by polymerization of ethylene oxide and are commercially available over a wide range of molecular weights from 300 Da to 10,000,000 Da or 300 Da to 10,000 Da. In certain embodiments, PEGs having molecular weights from 200 to 1000 or from 200 to 500 are used. Different forms of PEG may also be used, depending on the initiator used for the polymerization process—a common initiator is a monofunctional methyl ether PEG, or methoxypoly(ethylene glycol), abbreviated mPEG. Lower-molecular-weight PEGs are also available as pure oligomers, referred to as monodisperse, uniform, or discrete. These are used in certain embodiments of the present invention. PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9) would have an average molecular weight of approximately 400 Daltons, and would be labeled PEG 400.

As used herein, "PEGylation" is the act of covalently coupling a PEG structure to the peptide inhibitor of the invention, which is then referred to as a "PEGylated peptide inhibitor". In certain embodiments, the PEG of the PEGylated side chain is a PEG with a molecular weight from about 200 Da to about 40,000 Da or from about 200 Da to about 10,000 Da. In certain embodiments, the PEG is PEG3, PEG4, PEG5, PEG6, PEG7, PEG8, PEG9, PEG10, or PEG11. The skilled worker will be well aware of suitable techniques which can be used to perform the coupling reaction.

In some embodiments, the polymeric moiety is coupled (by covalent linkage) to an amino, carboxyl or thiol group of an amino acid side chain. Certain examples are the epsilon amino group of Lys residues, and the carboxyl groups of Asp and Glu residues may also be involved.

Several chemical moieties, including PEGs, react with functional groups present in the twenty naturally occurring amino acids, such as, for example, the epsilon amino group in lysine amino acid residues, the thiol present in cysteine amino acid residues, or other nucleophilic amino acid side chains. When multiple naturally occurring amino acids react in a peptide inhibitor, these non-specific chemical reactions result in a final peptide inhibitor that contains many isomers of peptides conjugated to one or more poly(ethylene)glycol strands at different locations within the peptide inhibitor.

One advantage of certain embodiments of opioid agonist peptides disclosed herein includes the ability to add one or more chemical moiety (such as PEG) by incorporating one or more non-natural amino acid(s) that possess unique functional groups that react with an activated PEG by way of chemistry that is unreactive with the naturally occurring amino acids present in the peptide inhibitor. For example, azide and alkyne groups are unreactive with all naturally occurring functional groups in a protein. Thus, a non-natural amino acid may be incorporated in one or more specific sites in an opioid agonist peptide where PEG or another modification is desired without the undesirable non-specific reactions. In certain embodiments, the particular chemistry involved in the reaction results in a stable, covalent link between the PEG strand and the opioid agonist peptide. In addition, such reactions may be performed in mild aqueous conditions that are not damaging to most peptides. In certain embodiments, the non-natural amino acid residue is AHA.

Chemical moieties attached to natural amino acids are limited in number and scope. By contrast, chemical moieties attached to non-natural amino acids can utilize a significantly greater spectrum of useful chemistries by which to attach the chemical moiety to the target molecule. Essentially any target molecule, including any protein (or portion thereof) that includes a non-natural amino acid, e.g., a non-natural amino acid containing a reactive site or side chain where a chemical moiety may attach, such as an aldehyde- or keto-derivatized amino acid, can serve as a substrate for attaching a chemical moiety.

Numerous chemical moieties may be joined or linked to a particular molecule through various known methods in the art. A variety of such methods are described in U.S. Pat. No. 8,568,706. As an illustrative example, azide moieties may be useful in conjugating chemical moieties such as PEG or others described herein. The azide moiety serves as a reactive functional group, and is absent in most naturally occurring compounds (thus it is unreactive with the native amino acids of naturally occurring compounds). Azides also undergo a selective ligation with a limited number of reaction partners, and azides are small and can be introduced to biological samples without altering the molecular size of significantly. One reaction that allows incorporation or introduction of azides to molecules is the copper-mediated Huisgen [3+2] cycloaddition of an azide. This reaction can be used for the selective PEGylation of peptide inhibitors. (Tomoe et al., J. Org. Chem. 67: 3057, 2002; Rostovtsev et al., Angew. Chem., Int. Ed. 41: 596, 2002; and Wang et al., J. Am. Chem. Soc. 125: 3192, 2003, Speers et al., J. Am. Chem. Soc., 2003, 125, 4686).

In particular embodiments, an opioid agonist peptide or pharmaceutically acceptable salt or solvate thereof comprising a peptide of Formula I, or an opioid agonist peptide dimer or pharmaceutically acceptable salt or solvate thereof comprising a peptide of Formula I, further comprising a conjugated chemical substituent. In certain embodiments, the conjugated chemical substituent is a lipophilic substituent or a polymeric moiety. In particular embodiments, the conjugated chemical substituent is Ac, Palm, gamaGlu-Palm, isoGlu-Palm, PEG2-Ac, PEG4-isoGlu-Palm, $(PEG)_5$-Palm, succinic acid, glutaric acid, pyroglutaric acid, benzoic acid, IVA, octanoic acid, 1,4 diaminobutane, isobutyl, or biotin. In particular embodiments, the conjugated chemical substituent is a polyethylene glycol with a molecular mass of 400 Da to 2,000 Da.

Functional Properties

In particular embodiments, opioid agonist peptides disclosed herein are stable under gastro intestinal (GI) conditions or when administered orally. In particular embodiments, opioid agonist peptides disclosed herein have a half-life in simulated gastric fluid (SGF; according to an assay described herein) of at least 60 min, at least 120 min, at least 240 min, at least 360 min, at least 480 min, or at least 1200 min. In particular embodiments, opioid agonist peptides disclosed herein have a half-life in simulated intestinal fluid (SIF; according to an assay described herein) of at least 60 min, at least 120 min, at least 240 min, at least 360 min, at least 480 min, or at least 1200 min.

In particular embodiments, opioid agonist peptides disclosed herein are stable in plasma or serum. In particular embodiments, opioid agonist peptides disclosed herein have a half-life in plasma (according to an assay described herein) or serum of at least 60 min, at least 120 min, at least 240 min, at least 360 min, at least 480 min, or at least 1200 min.

In certain embodiments, the opioid agonist peptides are stable to various pHs that range from strongly acidic in the stomach (pH 1.5-1.9), trending towards basic in the small intestine (pH 6-7.5), and then weakly acidic in the colon (pH 5-7). Such opioid agonist peptides are stable during their transit through the various gastro intestinal compartments, a process that has been estimated to take 3-4 h in the intestine and 6-48 h in the colon.

In some embodiments, the opioid agonist peptides of the present invention have less degradation, e.g., over a period of time (e.g., 4 hours, 8 hours, 12 hours or 48 hours), e.g., greater than or about 10% less, greater than or about 20% less, greater than or about 30% less, greater than or about 40 less, or greater than or about 50% less degradation than a control peptide. In some embodiments, degradation stability is determined via any suitable method known in the art. In some embodiments, the degradation is enzymatic degradation. For example, in certain embodiments, the peptide inhibitors have reduced susceptibility to degradation by trypsin, chymotrypsin or elastase. In some embodiments, suitable methods known in the art for determining degradation stability include the method described in Hawe et al., J Pharm Sci, VOL. 101, No. 3, 2012, p 895-913, incorporated herein in its entirety. Such methods are in some embodiments used to select potent opioid agonist peptides with enhanced shelf lives. In particular embodiments, opioid agonist peptide is determined using a SIF assay or SGF assay as described herein.

In particular embodiments, opioid agonist peptides disclosed herein agonize one or both of the mu- and delta-opioid receptors (MOR or DOR). In specific embodiments, opioid agonist peptides disclosed herein have a potency (EC50) of less than 10 nM, less than 5 nM, less than 3 nM, less than 2 nM, less than 1 nM, less than 0.5 nM, less than 0.3 nM, less than 0.2 nM, less than 0.1 nM, less than 0.05 nM, or less than 0.03 nM for one or both of MOR or DOR, e.g., as determined by a cAMP assay described in the Examples.

In particular embodiments, opioid agonist peptides disclosed herein selectively agonize either the MOR or DOR, e.g., agonize either MOR or DOR to a greater degree than the other, e.g., as determined by a cAMP assay described in the Examples.

In particular embodiment, opioid agonist peptides disclosed herein selectively agonize the MOR, and have a ratio of EC50 for DOR to EC50 for MOR of at least 1:1, 1.5:1, at least 2:1, at least 3:1, at least 5:1, at least 10:1, at least 20:1, at least 30:1, at least 50:1, at least 100:1, at least 200:1, at least 300:1, at least 500:1, or at least 1000:1.

In particular embodiment, opioid agonist peptides disclosed herein selectively agonize the DOR, and have a ratio of EC50 for MOR to EC50 for DOR of at least 1.5:1, at least 2:1, at least 3:1, at least 5:1, at least 10:1, at least 20:1, at least 30:1, at least 50:1, at least 100:1, at least 200:1, at least 300:1, at least 500:1, or at least 1000:1.

In certain embodiments, opioid agonist peptides described herein show GI-restricted localization following oral administration. In particular embodiments, greater than 50%, greater than 60%, greater than 70%, greater than 80%, or greater than 90% of orally administered opioid agonist peptide is localized to gastrointestinal organs and tissues. In particular embodiments, blood plasma levels of orally administered opioid agonist peptide are less than 20%, less than 10%, less than 5%, less than 2%, less than 1% or less than 0.5% the levels of opioid peptide agonist found in the small intestine mucosa, colon mucosa, or proximal colon.

In certain embodiments, opioid agonist peptides described here inhibit gastro intestinal (GI) mobility, such as small intestine transit, e.g., as determined by an assay described in the Examples. In particular embodiments, GI motility is inhibited or reduced by at least 10%, at least 20%, at least 30%, at least 40%, at least 50%, or at least 60%, as compared to no treatment or a negative control.

In certain embodiments, opioid agonist peptides described herein reduce or inhibit pain, e.g., GI pain, e.g., as determined by an assay described in the Examples. In particular embodiments, pain, e.g., GI pain, is inhibited or reduced by at least 10%, at least 20%, at least 30%, at least 40%, at least 50%, or at least 60%, as compared to no treatment or a negative control.

The present invention also includes opioid agonist peptides comprising a peptide sequence having at least 90%, at least 95%, at least 98%, or at least 99% sequence identity to the peptide sequence of an opioid agonist peptide described herein. In particular embodiments, opioid agonist peptides of the present invention comprise a core peptide sequence and one or more internal or C-terminal modification (e.g., $NH_2$) and/or one or more conjugated linker moiety and/or half-life extension moiety. As used herein, the core peptide sequence is the amino acid sequence of the peptide absent such modifications and conjugates.

Opioid agonist peptides may be synthesized by many techniques that are known to those skilled in the art, including routine methods of chemically synthesizing peptides. In certain embodiments, opioid agonist peptides are synthesized, purified, and optionally dimerized using the techniques described in the accompanying Examples. In certain embodiments, the present invention provides a method of producing an opioid agonist peptide of the present invention, comprising chemically synthesizing a peptide comprising, consisting of, or consisting essentially of a peptide having an amino acid sequence described herein, including but not limited to any of the amino acid sequences set forth in any of Formula I or tables herein. In other embodiments, the peptide is recombinantly synthesized, instead of being chemically synthesized. In certain embodiments, the peptide inhibitor is a dimer, and the method comprises synthesizing both monomer subunits of the peptide dimer and then dimerizing the two monomer subunits to produce the opioid agonist peptide dimer. In various embodiments, dimerization is accomplished via any of the various methods described herein.

The present invention also includes nucleic acids encoding peptides comprising any of the opioid agonist peptide sequences disclosed herein, vectors comprising any of such nucleic acids, and cells comprising any of such nucleic acids or vectors, which may be used for the in vitro or recombinant production of the opioid agonist peptides.

Labeled Opioid Agonist Peptides

In certain embodiments, any of the opioid agonist peptides are labeled, e.g., detectably labeled. In particular embodiments, the opioid agonist peptide is fluorescently labeled with a fluorophore or radiolabeled with a radioisotope, e.g., a stable isotope. A variety of detectable molecules may be used, such as radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody). Methods for conjugating polypeptides and detectable labels are well known in the art, as are methods for imaging using detectable labels. Peptides tagged with a detectable label may be employed in a wide variety of assays, employing a wide variety of labels.

Examples of detectable labels include but are not limited to radionucleotides, enzymes, coenzymes, fluorescers, chemiluminescers, chromogens, enzyme substrates or co-factors, enzyme inhibitors, prosthetic group complexes, free radicals, particles, dyes, and the like. Several radioisotopes can be used as detectable molecules for labeling peptides including, for example, 32P, 33P, 35S, 3H, and 125I. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, coumarin, Alexa488, Oregon green 488, rhodamine green, Alexa 532, Cy3, Bodipy 588/586, Alexa586, TAMRA, Rox, Alexa 594, Texas red, Bodipy 630/650, Cy5, Alexa647, IR Dye 680, IR Dye 680, IR Dye 700 DX, Cy5.5, Alexa 750, IR Dye 800CW, IR Dye 800, Atto 532, Atto 465; an example of a luminescent material is luminol; examples of bioluminescent materials include luciferase, luciferin, and aequorin; and examples of suitable radioactive material include 125I, 131I, 35S, or 3H. In some embodiments, the detectable labels include fluorescent proteins. In some embodiments of the present invention, detectable labels also include quenchers suitable for fluorescence resonance energy transfer (FRET) pairings. Examples of suitable quenchers include Dabcyl, BHQ1, BHQ2, BHQ3, CY5Q, CY7Q, Iowablack FQ, Iowablack RQ, IR Dye QC-1, QSY35, QSKY7, QXL570, QXL610, QXL680.

In certain embodiments, any of the opioid agonist peptides are deuterated at one or more positions, i.e., they comprise deuterium instead of hydrogen at one or more positions. Deuterium is a naturally-occurring, stable, non-radioactive isotope of hydrogen. Selective incorporation of deuterium in place of hydrogen (deuteration) typically retains that biochemical potency and selectivity of a physiologically active compound, and may confer favorable properties, such as increased stability, and/or therapeutic safety, efficacy, and/or tolerability. Methods of selectively incorporating deuterium instead of hydrogen are known in the art.

Pharmaceutical Compositions and Methods of Use

The present invention also includes pharmaceutical compositions comprising an opioid agonist peptide disclosed herein and a pharmaceutically acceptable excipient, diluent or carrier. A pharmaceutically acceptable carrier, diluent or excipient refers to a non-toxic solid, semi-solid or liquid filler, diluent, encapsulating material or formulation auxiliary of any type, e.g., a buffer. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

In certain embodiments, the compositions are formulated to be administered orally, parenterally, intracistemally, intravaginally, intraperitoneally, intrarectally, intraenteral, topically (such as by powders, ointments, drops, suppository, or transdermal patch), by inhalation (such as intranasal spray), ocularly (such as intraocularly) or buccally. The term "parenteral" as used herein refers to modes of administration which include intravenous, intramuscular, intraperitoneal, intrasternal, subcutaneous, intradermal and intraarticular injection and infusion.

In some aspects, the invention provides a pharmaceutical composition for oral delivery. Pharmaceutical compositions may be prepared for oral administration according to any of the methods, techniques, and/or delivery vehicles described herein. Further, one having skill in the art will appreciate that the opioid agonist peptides may be integrated into a system or delivery vehicle that is not disclosed herein, yet is well known in the art and compatible for use in oral delivery of peptides.

In particular embodiments, oral dosage forms or unit doses compatible for use with the opioid agonist peptides of the present invention may include a mixture of opioid agonist peptide and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of an opioid agonist peptide, wherein the dosage form comprises at least one of a pill, a tablet, a capsule, a gel, a paste, a drink, a syrup, ointment, and suppository. In some instances, an oral dosage form is provided that is designed and configured to achieve delayed release of the opioid agonist peptide in the subject's small intestine and/or colon.

In certain embodiments, pharmaceutical compositions for oral administration comprise adjuvants (e.g., resorcinols and/or nonionic surfactants such as polyoxyethylene oleyl ether and n-hexadecylpolyethylene ether) to artificially increase the permeability of the intestinal walls, and/or enzymatic inhibitors (e.g., pancreatic trypsin inhibitors, diisopropylfluorophosphate (DFF) or trasylol) to inhibit enzymatic degradation. In certain embodiments, the opioid agonist peptide of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

In certain embodiments, a pharmaceutical composition comprising an opioid agonist peptide is provided in an enteric coating, the enteric coating being designed to protect and release the pharmaceutical composition in a controlled manner within the subject's lower gastrointestinal system, and to avoid systemic side effects. In one embodiment, the enteric coating delays release of the peptide inhibitor in the small intestine. In at least some embodiments, a pharmaceutical composition is provided which comprises an opioid agonist peptide and a protease inhibitor, such as aprotinin, in a delayed release pharmaceutical formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In addition to enteric coatings, the opioid agonist peptides and related pharmaceutical compositions may be encapsulated, coated, engaged or otherwise associated within any compatible oral drug delivery system or component. For example, in some embodiments an opioid agonist peptide or related pharmaceutical composition is provided in a lipid carrier system comprising at least one of polymeric hydrogels, nanoparticles, microspheres, micelles, and other lipid systems.

Various bioresponsive systems may also be combined with one or more opioid agonist peptide to provide a pharmaceutical agent for oral delivery. In some embodiments, an opioid agonist peptide is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for an opioid agonist peptide, wherein the opioid agonist peptide surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the opioid agonist peptide.

Other embodiments include a pharmaceutical composition comprising an opioid agonist peptide and a permeation enhancer to promote the transport of the peptides across the intestinal mucosa by increasing paracellular or transcellular permeation. Various permeation enhancers and methods for the oral delivery of therapeutic agents are described in Brayden, D. J., Mrsny, R. J., 2011. Oral peptide delivery: prioritizing the leading technologies. Ther. Delivery 2 (12), 1567-1573. Examples of permeation or absorption enhancers include Bile salts, fatty acids, surfactants (anionic, cationic, and nonanionic) chelators, Zonular OT, esters, cyclodextrin, dextran sulfate, azone, crown ethers, EDTA, sucrose esters, and phosphotidyl choline, for example. Although absorption enhancers are not typically carriers by themselves, they are also widely associated with other carriers to improve oral bioavailability by transporting of peptides and proteins across the intestinal mucosa. Such substances can be added to the pharmaceutical composition as excipients or incorporated to form non-specific interactions with the intended opioid agonist peptide.

Dietary components and/or other naturally occurring substances affirmed as enhancing tight junction permeation and as Generally Recognized as Safe (GRAS) include, e.g., asglycerides, acylcamitines, bile salts, and medium chain fatty acids. Sodium salts of medium chain fatty acids (MCFAS) were also suggested to be permeation enhancers. The most extensively studied MCFAS is sodium caproate, a salt of capric acid, which comprises 2-3% of the fatty acids in the milk fat fraction. To date, sodium caproate is mainly used as an excipient in a suppository formulation (Doktacillin™) for improving rectal ampicillin absorption. The permeation properties of another dietary MCFAS, sodium caprylate (8-carbon), were shown in vitro to be lower when compared to sodium caprate. Sodium caprylate and a peptidic drug were formulated in an admixture with other excipients in oil to generate an oily suspension (OS) that enhanced permeability (Tuvia, S. et al., Pharmaceutical Research, Vol. 31, No. 8, pp. 2010-2021 (2014).

For example, in one embodiment, a permeation enhancer is combined with an opioid agonist peptide, wherein the permeation enhancer comprises at least one of a medium-chain fatty acid, a long-chain fatty acid, a bile salt, an amphiphilic surfactant, and a chelating agent. In certain embodiments, medium-chain fatty acid salts promote absorption by increasing paracellular permeability of the intestinal epithelium. In one embodiment, a permeation enhancer comprising sodium N-[hydroxybenzoyl)amino] caprylate is used to form a weak noncovalent association with the opioid agonist peptide, wherein the permeation enhancer favors membrane transport and further dissociation once reaching the blood circulation. In another embodiment, an opioid agonist peptide is conjugated to oligoarginine, thereby increasing cellular penetration of the peptide into various cell types. Further, in at least one embodiment a noncovalent bond is provided between an opioid agonist peptide and a permeation enhancer selected from the group consisting of a cyclodextrin (CD) and a dendrimer, wherein the permeation enhancer reduces peptide aggregation and increasing stability and solubility for the opioid agonist peptide.

In certain embodiments, a pharmaceutical composition or formulation comprises an opioid agonist peptide and a transient permeability enhancers (TPEs). Permeation enhancers and TPEs may be used to increase oral bioavailability of the opioid agonist peptide. One example of a TPE that may be used is an oily suspension formulation that disperses a powder containing sodium caprylate and a therapeutic agent (Tuvia, S. et al., Pharmaceutical Research, Vol. 31, No. 8, pp. 2010-2021 (2014).

In certain embodiments, pharmaceutical composition and formulations may include an opioid agonist peptide and one or more absorption enhancers, enzyme inhibitors, or mucoso adhesive polymers.

When present in any of the pharmaceutical compositions described herein, the opioid agonist peptide may be present in pure form or in a pharmaceutically acceptable salt form.

In particular embodiments, opioid agonist peptides are formulated in a formulation vehicle, such as, e.g., emulsions, liposomes, microsphere or nanoparticles.

The opioid agonist peptides may be used to agonize one or both of the MOR and DOR. In particular embodiments, a method of agonizing one or more of the MOR and DOR comprises contacting a cell comprising a MOR and/or a DOR with an opioid agonist peptide described herein. The method may be practiced in vitro, e.g., using cultured cells, or in vivo, e.g., by providing to a subject a pharmaceutical composition comprising the opioid agonist peptide. In particular embodiments, a method of selectively agonizing the MOR is provided, wherein the method comprises contacting a cell comprising a MOR (and optionally a DOR) with an opioid agonist peptide described herein that selectively agonizes MOR as compared to DOR. In particular embodiments, a method of selectively agonizing a DOR is provided, comprising contacting a cell comprising a DOR (and optionally a MOR) with an opioid agonist peptide described herein that selectively agonizes DOR as compared to MOR. In particular embodiments, the selective DOR agonist comprises a lipophilic amino acid at X5 of Formula I.

In particular embodiments, the opioid agonist peptides are used to treat or prevent gastrointestinal (GI) motility disorders, GI enteric pain, GI inflammation, and diseases associated with enteric pain.

The opioid agonist peptides may be used to inhibit or reduce gastro intestinal motility, e.g., motility in the small intestine. Methods for inhibiting gastro intestinal motility comprise providing to a subject in need thereof an effective amount of a pharmaceutical composition comprising an opioid agonist peptide disclosed herein. In particular embodiments, the subject has been diagnosed with or is considered at risk of developing diarrhea. In certain embodiments, the subject has been diagnosed with irritable bowel syndrome, (IBS), IBS with diarrhea, inflammatory bowel disease (IBD), ulcerative colitis, Crohn's disease, or celiac disease. In particular embodiments, the methods are used to treat or prevent diseases associated with defects in motility such as but not limited to: bowel incontinence (also referred to as fecal incontinence or accidental bowel leakage (ABL), acute radiation injury, scleroderma, and short bowel syndrome. In particular embodiments, the pharmaceutical composition is provided to the subject orally.

The opioid agonist peptides may be used to inhibit or reduce pain or discomfort, e.g., pain or discomfort associated with a gastro intestinal disease or disorder, including but not limited to, irritable bowel syndrome, (IBS), IBS with diarrhea, inflammatory bowel disease (IBD), ulcerative colitis, Crohn's disease, or celiac disease. Methods for inhibiting or reducing pain or discomfort, e.g., gastro intestinal pain or discomfort, comprise providing to a subject in need thereof an effective amount of a pharmaceutical composition comprising an opioid agonist peptide disclosed herein. In particular embodiments, the methods are used to treat or prevent enteric pain, and diseases associated with enteric pain such as: intestinal pseudo-obstruction, centrally mediated abdominal pain syndrome (CAPS), and eosinophilic gastroenteritis. In particular embodiments, the pharmaceutical composition is provided to the subject orally.

The opioid agonist peptides may be used to treat or prevent a gastro intestinal or inflammatory disease or disorder, e.g., a gastro intestinal inflammatory disease or disorder. Methods for treating or preventing a gastro intestinal disease or disorder or inflammatory disease or disorder, comprise providing to a subject in need thereof an effective amount of a pharmaceutical composition comprising an opioid agonist peptide disclosed herein. In certain embodiments, the subject has been diagnosed with irritable bowel syndrome, (IBS), IBS with diarrhea, inflammatory bowel disease (IBD), ulcerative colitis, Crohn's disease, or celiac disease. In particular embodiments, the methods are used to treat or prevent a disease or disorder associated with GI inflammation, such as, e.g., Celiac disease (nontropical Sprue), enteropathy associated with seronegative arthropathies, microscopic colitis, collagenous colitis, eosinophilic gastroenteritis/esophagitis, colitis associated with radio- or chemo-therapy, colitis associated with disorders of innate immunity as in leukocyte adhesion deficiency-1, or pouchitis resulting after proctocolectomy and ileoanal anastomosis. In particular embodiments, the pharmaceutical composition is provided to the subject orally.

In certain embodiments, the disease or disorder is irritable bowel syndrome (IBS), irritable bowel syndrome with diarrhea (IBS-D), mixed irritable bowel syndrome (mixed IBS), inflammatory bowel diseases (IBDs), juvenile IBD, adolescent IBD, or Crohn's disease. In particular embodiments, the disease or disorder is ulcerative colitis, Crohn's disease, Celiac disease (nontropical Sprue), enteropathy associated with seronegative arthropathies, microscopic colitis, collagenous colitis, eosinophilic gastroenteritis/esophagitis, colitis associated with radio- or chemo-therapy, colitis associated with disorders of innate immunity as in leukocyte adhesion deficiency-1, or pouchitis resulting after proctocolectomy and ileoanal anastomosis.

Various embodiments of the invention disclosed herein provide methods for treating a subject with an opioid agonist peptide or pharmaceutical composition described herein. In one aspect, the present invention provides an opioid agonist peptide having a half-life of at least several hours to one day in vitro or in vivo (e.g., when administered to a human subject) sufficient for daily (q.d.) or twice daily (b.i.d.) dosing of a therapeutically effective amount. In another embodiment, the opioid agonist peptide has a half-life of three days or longer sufficient for weekly (q.w.) dosing of a therapeutically effective amount. Further, in another embodiment, the opioid agonist peptide has a half-life of eight days or longer sufficient for bi-weekly (b.i.w.) or monthly dosing of a therapeutically effective amount.

The total daily usage of the opioid agonist peptides and pharmaceutical compositions can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, d) the age, body weight, general health, sex and diet of the patient; e) the time of administration, route of administration, and rate of excretion of the specific peptide inhibitor employed; f) the duration of the treatment; g) drugs used in combination or coincidental with the specific peptide inhibitor employed, and like factors well known in the medical arts.

In particular embodiments, the total daily dose of the opioid agonist peptides provided to a human or other mammal host in single or divided doses may be in amounts, for example, from 0.0001 to 300 mg/kg body weight daily or 1 to 300 mg/kg body weight daily.

In addition to the methods described in the Examples herein, the peptides of the present invention may be produced using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2 ed. Pierce, Rockford, Ill., which are herein incorporated by reference. The hepcidin analogues of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the hepcidin analogues of the present invention may be made by recombinant DNA techniques known in the art. Thus, polynucleotides that encode the polypeptides of the present invention are contemplated herein. In certain preferred embodiments, the polynucleotides are isolated. As used herein "isolated polynucleotides" refers to polynucleotides that are in an environment different from that in which the polynucleotide naturally occurs.

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

Abbreviations

DCM: dichloromethane
DMF: N,N-dimethylformamide
NMP: N-methylpyrolidone
HBTU: O-(Benzotriazol-1-yl)-N,N,N',N'-tetramethyluronium hexafluorophosphate
HATU: 2-(7-aza-1H-benzotriazole-1-yl)-1,1,3,3-tetramethyluronium hexafluorophosphate
DCC: Dicyclohexylcarbodiimide
NHS: N-hydroxysuccinimide
DIPEA: diisopropylethylamine
EtOH: ethanol
Et2O: diethyl ether
Hy: hydrogen
TFA: trifluoroacetic acid
TIS: triisopropylsilane
ACN: acetonitrile
HPLC: high performance liquid chromatography
ESI-MS: electron spray ionization mass spectrometry
PBS: phosphate-buffered saline
Boc: t-butoxycarbonyl
Fmoc: Fluorenylmethyloxycarbonyl
Acm: acetamidomethyl
IVA: Isovaleric acid (or Isovaleryl)

Unless otherwise specified, reagents and solvents employed in the following were available commercially in standard laboratory reagent or analytical grade, and were used without further purification.

Example 1
Representative Synthesis of Peptide Analogues
Synthesis of DMT-D(Ala)-Gly-bhF-Gly-NH₂
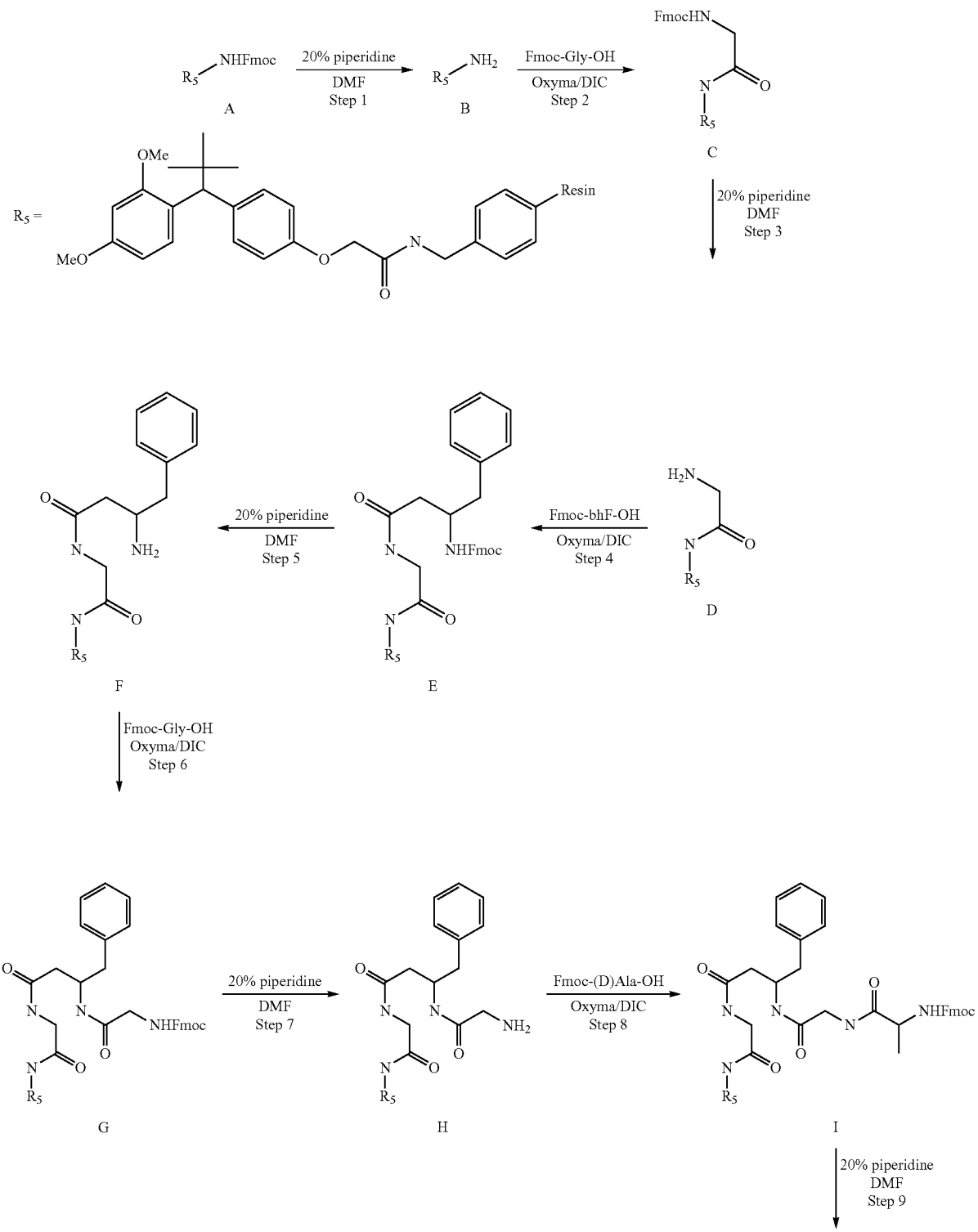

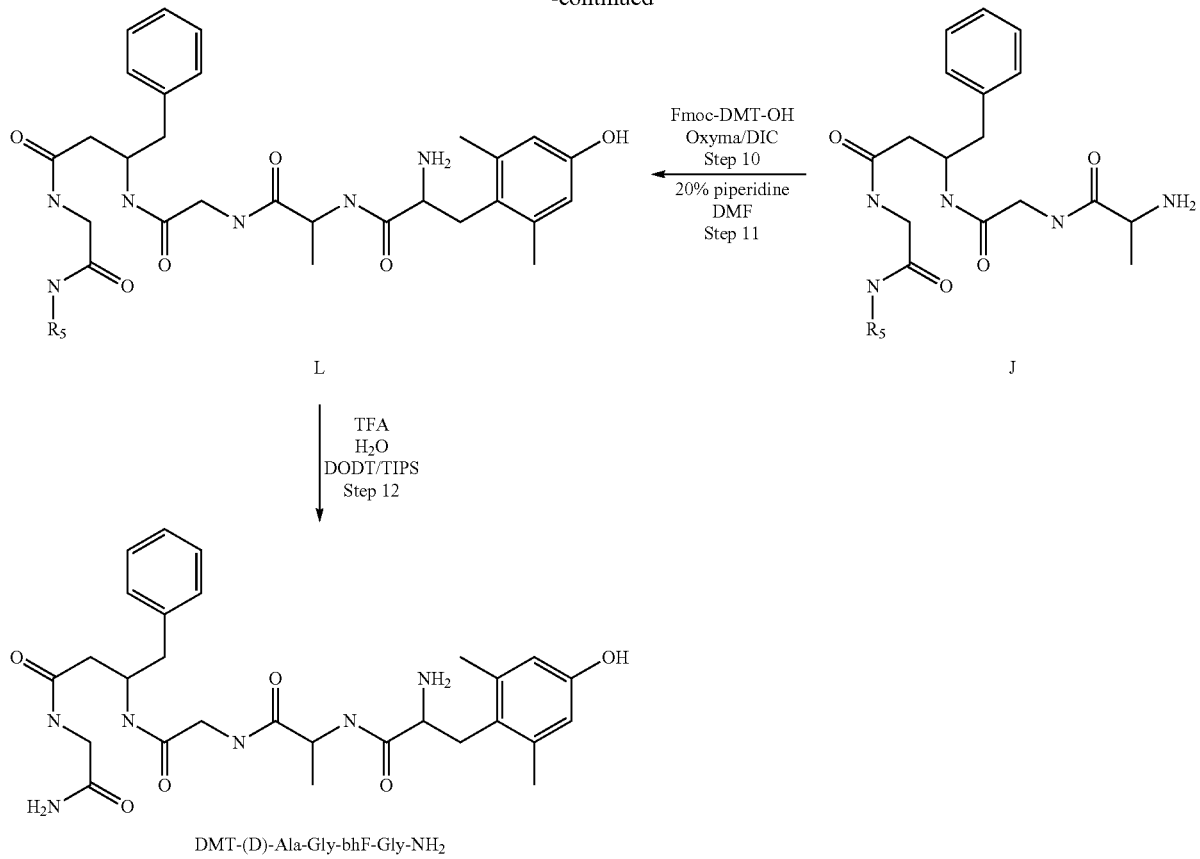

DMT-(D)-Ala-Gly-bhF-Gly-NH$_2$

Step 1: Synthesis of Resin (B)

To the Rink Amide-MBHA resin A (5 g, 3.3 mmol, 0.66 mmol/g loading), piperidine in DMF (20 mL, 20% solution) was added and left stirred at room temperature for 15 minutes. The solvent and excess reagent was filtered off from the resin and washed with DMF (4×20 mL).

Again, piperidine in DMF (20 mL, 20% solution) was added and left stirred for an hour. Again, the solvent and excess reagent was filtered off, and the resin was washed with DMF (5×20 mL) and dried under vacuum.

Step 2: Synthesis of Gly-Resin (C)

The oxyma ester prepared by stirring Fmoc-Glycine (1.96 g, 6.6 mmol), oxyma (0.937 g, 6.6 mmol) and N,N'-diisopropylcarbodiimide (DIC) (1 mL, 6.6 mmol) at room temperature for an hour was added to the resin (A) and left stirred at room temperature for 3 hours. At the end, the excess reagent was filtered off, washed with DMF (4×20 mL) and dried.

Step 3: Synthesis of Gly-Resin (D)

To the above resin (B), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 4: Synthesis of Beta-homoPhe-Gly-Resin (E)

The oxyma ester prepared by stirring Fmoc-beta-homophenylalanine (2.64 g, 6.6 mmol), oxyma (0.937 g, 6.6 mmol) and DIC (1 mL, 6.6 mmol) at room temperature for an hour was added to the resin (C) and left stirred at room temperature for 3 hours. At the end, the excess reagent was filtered off, washed with DMF (4×20 mL) and dried.

Step 5: Synthesis of Beta-homoPhe-Gly-Resin (F)

To the resin (D), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 6: Synthesis of Gly-bhF-Gly-Resin (G)

The oxyma ester prepared by stirring Fmoc-Glycine (1.96 g, 6.6 mmol), oxyma (0.937 g, 6.6 mmol) and DIC (1 mL, 6.6 mmol) at room temperature for an hour was added to the resin (D) and left stirred for 3 hours. At the end, the excess reagent was filtered off, washed with DMF (4×20 mL) and dried.

Step 7: Synthesis of Gly-bhF-Gly-Resin (H)

To the resin (F), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 8: Synthesis of D(Ala)-Gly-bhF-Resin (I)

The oxyma ester, prepared by stirring Fmoc-D-Alanine (2.05 g, 6.6 mmol), oxyma (0.937 g, 6.6 mmol) and DIC (1 mL, 6.6 mmol) at room temperature for an hour was added to the resin (G) and left stirred for 3 hours. At the end, the excess reagent was filtered off, washed with DMF (4×20 mL) and dried.

Step 9: Synthesis of D(Ala)-Gly-bhF-Resin (J)

To the resin (H), piperidine in DMF (20 mL, 20% solution) was added and left stirred at room temperature for 15 minutes. The solvent and excess reagent was filtered off from resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 10: Synthesis of DMT-D(Ala)-Gly-bhF-Gly-Resin (K) (SEQ ID NO:112)

The oxyma ester prepared by stirring Fmoc-2,6-dimethyl-tyrosine (2.84 g, 6.6 mmol), oxyma (0.937 g, 6.6 mmol) and DIC (1 mL, 6.6 mmol) at room temperature for an hour was added to the resin (I) and left stirred for 3 hours. At the end, the excess reagent was filtered off, washed with DMF (4×20 mL) and dried.

Step 11: Synthesis of DMT-D(Ala)-Gly-bhF-Gly-Resin (L) (SEQ ID NO: 112)

To the resin (J), piperidine in DMF (20 mL, 20% solution) was added and left stirred at room temperature for 15 minutes. The solvent and excess reagent was filtered off from resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 12: Synthesis of DMT-D(Ala)-Gly-bhF-Gly-NH$_2$ (SEQ ID NO: 112)

The resin (K) (5.5 g) was then split in to 4 portions and to each portion a mixture of trifluoroacetic acid (9 mL), water (0.5 mL), triisopropylsilane (0.25 mL) and 2,2'-(ethylenedioxy)diethanethiol (0.25 mL) was added and stirred at room temperature for 2 hours to cleave the pentapeptide from the resin. The resin was filtered off. To the filtrate, cold ether was added (30 mL). A white precipitate formed was filtered off and washed with ether (3×20 mL) and air dried.

The white precipitate (3 g) was then dissolved in acetonitrile/water mixture (5%, 30 mL), injected in to preparative HPLC column and eluted with a mixture of acetonitrile and water with 0.1% trifluoroacetic acid (25% to 65% gradient in 60 minutes with a flow rate of 75 mL/min) to obtain pure (>96%) peptide (DMT-D(Ala)-Gly-bhF-Sar-NH$_2$) (SEQ ID NO:43) as white fluffy solid after freezing and lyophilizing the pure HPLC fractions.

The other peptides are or can also be prepared following procedures similar to Example 1. The mass spect data of the representative peptides of the present invention is listed in Table 3A.

Example 2

Representative Synthesis of Peptide Dimer Analogues

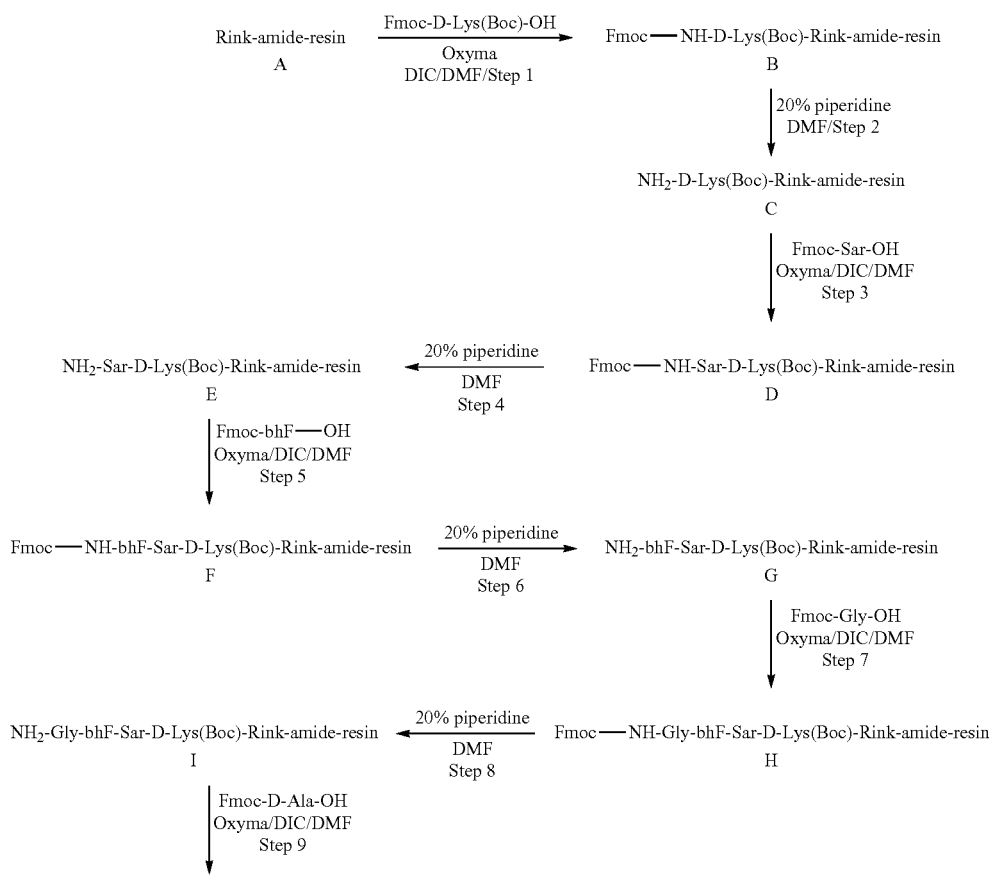

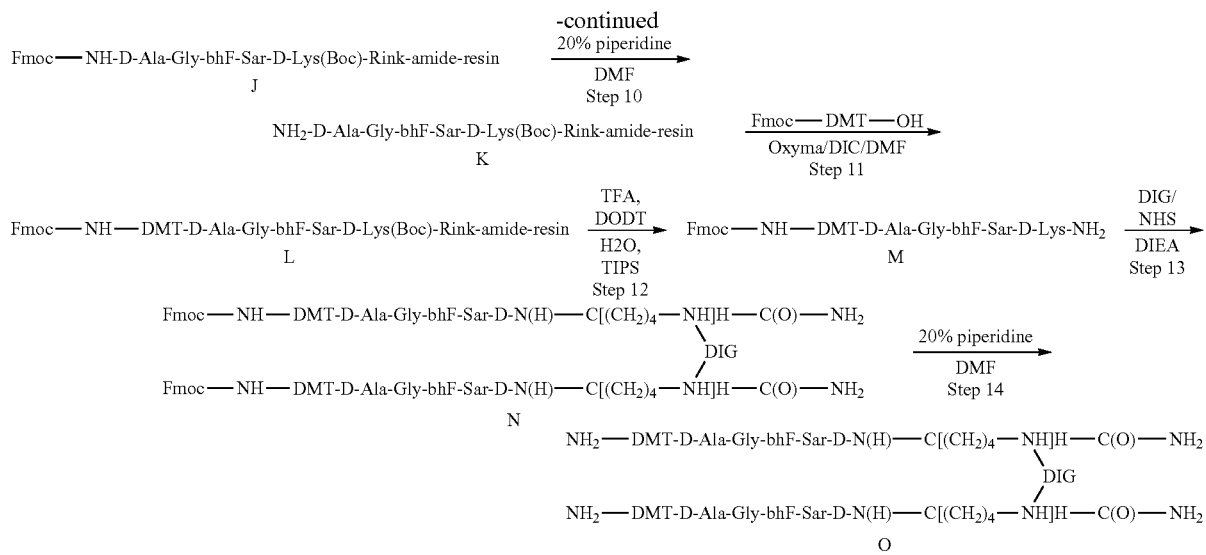

Synthesis of Resin (A)

To the Rink Amide-MBHA resin (1 g, 0.66 mmol), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 1: Synthesis of Fmoc-NH-D-Lys(Boc)-Resin (B)

The oxyma ester prepared by stirring Fmoc-D-Lys(Boc)-OH (0.619 g, 1.32 mmol), oxyma (0.142 g, 1.98 mmol) and N,N'-diisopropylcarbodiimide (DIC) (0.265 mL, 1.71 mmol) in DMF (30 mL) at room temperature for an hour was added to the resin (A) and left stirred at room temperature for 3 hours. At the end, the excess reagent was filtered off, washed with DMF (4×20 mL) and dried.

Step 2: Synthesis of $NH_2$-D-Ly(Boc)-Resin (C)

To the above resin (B), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 3: Synthesis of Fmoc-NH-Sar-D-Lys(Boc)-Resin (D)

The oxyma ester prepared by stirring Fmoc-Sar-OH (0.411 g, 1.32 mmol), oxyma (0.142 g, 1.98 mmol) and DIC (0.265 mL, 1.71 mmol) in DMF (30 mL) at room temperature for an hour was added to the resin (C) and left stirred at room temperature for 3 hours. At the end, the excess reagent was filtered off, washed with DMF (4×20 mL) and dried.

Step 4: Synthesis of $NH_2$-Sar-D-Lys(Boc)-Resin (E)

To the resin (D), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 5: Synthesis of Fmoc-NH-bhF-Sar-D-Lys(Boc)-Resin (F)

The oxyma ester prepared by stirring Fmoc-bhF-OH (0.530 g, 1.32 mmol), oxyma (0.142 g, 1.98 mmol) and DIC (0.530 mL, 3.42 mmol) in DMF (45 mL) at room temperature for an hour was added to the resin (E) and left stirred for 3 hours. At the end, the excess reagent was filtered off, washed with DMF (4×20 mL) and dried.

Step 6: Synthesis of $NH_2$-bhF-Sar-D-Lys(Boc)-Resin (G)

To the resin (F), piperidine in DMF (20 mL, 20% solution) was added and left stirred at room temperature for 15 minutes. The solvent and excess reagent was filtered off from the resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 7: Synthesis of Fmoc-NH-Gly-bhF-Sar-D-Lys(Boc)-resin (H) (SEQ ID NO:337)

The oxyma ester, prepared by stirring Fmoc-Gly-OH (0.784 g, 2.64 mmol), oxyma (0.562 g, 3.96 mmol) and DIC (0.530 mL, 3.43 mmol) in DMF (45 mL) at room temperature for an hour was added to the resin (G) and left stirred for 3 hours. At the end, the excess reagent was filtered off, washed with DMF (4×20 mL) and dried.

Step 8: Synthesis of $NH_2$-Gly-bhF-Sar-D-Lys(Boc)-Resin (I) (SEQ ID NO:337)

To the resin (H), piperidine in DMF (20 mL, 20% solution) was added and left stirred at room temperature for 15 minutes. The solvent and excess reagent was filtered off from resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 9: Synthesis of Fmoc-NH-D-Ala-Gly-bhF-Sar-D-Lys(Boc)-Resin (J) (SEQ ID NO:338)

The oxyma ester prepared by stirring Fmoc-D-Ala-OH (0.821 g, 2.64 mmol), oxyma (0.784 g, 2.64 mmol) and DIC (0.530 mL, 3.43 mmol) in DMF (45 mL) at room temperature for an hour was added to the resin (I) and left stirred for 3 hours. At the end, the excess reagent was filtered off, washed with DMF (4×20 mL) and dried.

Step 10: Synthesis of NH$_2$-D-Ala-Gly-bhF-Sar-D-Lys(Boc)-Resin (K) (SEQ ID NO:338)

To the resin (J), piperidine in DMF (20 mL, 20% solution) was added and left stirred at room temperature for 15 minutes. The solvent and excess reagent was filtered off from resin and washed with DMF (4×20 mL).

Again, pieridine in DMF (20 mL, 20% solution) was added and left stirred for an hour. Again, the solvent and excess reagent was filtered off, and the resin was washed with DMF (5×20 mL) and dried under vacuum.

Step 11: Synthesis of Fmoc-NH-DMT-D-Ala-Gly-bhF-Sar-D-Lys(Boc)-Resin (L) (SEQ ID NO:270)

The oxyma ester prepared by stirring Fmoc-DMT-OH (1.44 g, 2.64 mmol), oxyma (0.784 g, 2.64 mmol) and DIC (0.530 mL, 3.43 mmol) in DMF (45 mL) at room temperature for an hour was added to the resin (K) and left stirred for 3 hours. At the end, the excess reagent was filtered off, washed with DMF (4×20 mL) and dried.

Step 12: Synthesis of Fmoc-NH-DMT-D-Ala-Gly-bhF-Sar-D-Lys-NH$_2$ (M) (SEQ ID NO:270)

To the resin (L) a mixture of trifluoroacetic acid (9 mL), water (0.5 mL), triisopropylsilane (0.25 mL) and 2,2'-(ethylenedioxy)diethanethiol (0.25 mL) was added and stirred at room temperature for 2 hours to cleave the peptide from the resin. The resin was filtered off. To the filtrate, cold ether was added (30 mL). A white precipitate formed was filtered off and washed with ether (3×20 mL) and air dried.

Step 13: Synthesis of Dimer (N) (SEQ ID NO:271):

To the monomer peptide M (0.170 g, 0.185 mmol) dissolved in DMF (3 mL), activated DIG linker (0.926 mL, 0.5 eq), prepared from mixing DIG (1 eq.), n-hydroxysuccinamide (2.1 eq.), DCC (2.1 eq) and DIEA (5 eg) was added and stirred at room temperature for 15 minutes. Cold ether (20 mL) was added to the reaction mixture to obtain the dimer N as a sticky solid.

Step 14: Synthesis of Dimer (O) (SEQ ID NO:271):

To the dimer N (116 mg), 20% piperidine in DMF (3 mL) was added and shaken for 30 minutes at room temperature. Cold ether (20 mL) was added to crash the dimer O as a white solid. The white solid was then dissolved in acetonitrile/water mixture (5%, 30 mL), injected in to preparative HPLC column and eluted with a mixture of acetonitrile and water with 0.1% trifluoroacetic acid (17% to 35% gradient in 60 minutes with a flow rate of 70 mL/min) to obtain pure (>96%) dimer peptide O as a white fluffy solid after freezing and lyophilizing the pure HPLC fractions (48 mg). The dimer O was confirmed my mass spectra (1491.70, M+1).

TABLE 3A

Mass Spect data of representative peptides having the indicated amino acid sequence

| Seq. ID | MW | MS (M + 1) |
| --- | --- | --- |
| 1 | 640.8 | 641.8 |
| 2 | 639.8 | 640.8 |
| 3 | 715.9 | 716.9 |
| 4 | 629.8 | 630.8 |
| 5 | 653.8 | 654.8 |
| 7 | 639.8 | 640.8 |
| 8 | 509.6 | 510.6 |
| 9 | 582.7 | 583.7 |
| 10 | 511.6 | 512.6 |
| 11 | 638.8 | 639.8 |
| 12 | 611.7 | 612.7 |
| 13 | 649.8 | 650.8 |
| 14 | 672.4 | 673.4 |
| 15 | 672.4 | 673.4 |
| 16 | 676.4 | 677.4 |
| 17 | 718.4 | 719.4 |
| 18 | 672.4 | 673.4 |
| 19 | 600.3 | 601.3 |
| 20 | 607.3 | 608.3 |
| 21 | 594.3 | 595.3 |
| 22 | 650.6 | 651.6 |
| 23 | 658.4 | 659.4 |
| 24 | 638.4 | 639.4 |
| 25 | 642.4 | 643.4 |
| 26 | 658.4 | 659.4 |
| 27 | 681.0 | 682.0 |
| 28 | 624.8 | 625.8 |
| 29 | 624.8 | 625.8 |
| 30 | 610.8 | 611.8 |
| 31 | 663.8 | 664.8 |
| 32 | 658.4 | 659.4 |
| 33 | 644.8 | 645.8 |
| 34 | 607.7 | 608.7 |
| 35 | 621.7 | 622.7 |
| 36 | 734.9 | 735.9 |
| 37 | 596.7 | 597.7 |
| 38 | 558.6 | 559.6 |
| 39 | 565.6 | 566.6 |
| 40 | 552.6 | 553.6 |
| 41 | 609.5 | 610.5 |
| 42 | 554.6 | 555.6 |
| 43 | 568.7 | 569.7 |
| 44 | 585.7 | 586.7 |
| 45 | 642.8 | 643.8 |
| 46 | 511.7 | 512.7 |
| 47 | 568.7 | 569.7 |
| 48 | 553.7 | 554.7 |
| 49 | 610.8 | 611.8 |
| 50 | 554.0 | 555.0 |
| 51 | 554.0 | 555.0 |
| 52 | 596.0 | 597.0 |
| 53 | 540.0 | 541.0 |
| 54 | 554.0 | 555.0 |
| 55 | 574.5 | 575.5 |
| 56 | 541.0 | 542.0 |
| 57 | 558.0 | 559.0 |
| 58 | 557.0 | 558.0 |
| 59 | 581.0 | 582.0 |
| 60 | 568.0 | 569.0 |
| 61 | 553.0 | 554.0 |
| 62 | 541.0 | 542.0 |
| 63 | 580.0 | 581.0 |
| 64 | 582.0 | 583.0 |
| 65 | 638.0 | 639.0 |
| 66 | 582.0 | 583.0 |
| 67 | 624.0 | 625.0 |
| 68 | 624.0 | 625.0 |
| 69 | 610.0 | 611.0 |
| 70 | 595.0 | 596.0 |
| 71 | 584.0 | 585.0 |
| 72 | 596.0 | 597.0 |
| 73 | 582.0 | 583.0 |
| 74 | 581.0 | 582.0 |
| 75 | 609.0 | 610.0 |
| 76 | 625.0 | 626.0 |
| 77 | 639.0 | 640.0 |
| 78 | 694.0 | 695.0 |
| 79 | 595.0 | 596.0 |
| 80 | 595.0 | 596.0 |
| 81 | 554.0 | 555.0 |
| 82 | 598.0 | 599.0 |
| 83 | 612.0 | 613.0 |
| 84 | 660.0 | 661.0 |
| 85 | 687.0 | 688.0 |
| 86 | 609.0 | 610.0 |

TABLE 3A-continued

Mass Spect data of representative peptides having the indicated amino acid sequence

| Seq. ID | MW | MS (M + 1) |
|---|---|---|
| 87 | 569.0 | 570.0 |
| 88 | 569.0 | 570.0 |
| 89 | 568.0 | 569.0 |
| 90 | 582.0 | 583.0 |
| 91 | 667.0 | 668.0 |
| 92 | 653.0 | 654.0 |
| 93 | 611.0 | 612.0 |
| 94 | 581.0 | 582.0 |
| 95 | 653.0 | 654.0 |
| 96 | 639.0 | 640.0 |
| 97 | 639.0 | 640.0 |
| 98 | 693.0 | 694.0 |
| 99 | 673.0 | 674.0 |
| 100 | 687.0 | 688.0 |
| 101 | 653.0 | 654.0 |
| 102 | 703.0 | 704.0 |
| 103 | 683.0 | 684.0 |
| 104 | 656.0 | 657.0 |
| 105 | 592.0 | 593.0 |
| 106 | 726.0 | 727.0 |
| 107 | 566.0 | 567.0 |
| 108 | 593.0 | 594.0 |
| 109 | 630.1 | 631.1 |
| 110 | 721.2 | 722.2 |
| 111 | 584.0 | 585.0 |
| 112 | 554.0 | 555.0 |
| 113 | 626.0 | 627.0 |
| 114 | 695.0 | 696.0 |
| 115 | 666.0 | 667.0 |
| 116 | 625.0 | 626.0 |
| 117 | 655.0 | 656.0 |
| 118 | 644.0 | 645.0 |
| 119 | 651.0 | 652.0 |
| 120 | 627.0 | 628.0 |
| 121 | 658.0 | 659.0 |
| 122 | 636.0 | 637.0 |
| 123 | 636.0 | 637.0 |
| 124 | 625.0 | 626.0 |
| 125 | 779.0 | 780.0 |
| 126 | 666.8 | 667.8 |
| 127 | 666.8 | 667.8 |
| 128 | 666.8 | 667.8 |
| 131 | 670.4 | 671.4 |
| 136 | 778.7 | 779.7 |
| 137 | 687.3 | 688.3 |
| 138 | 668.8 | 669.8 |
| 139 | 691.9 | 692.9 |
| 140 | 640.0 | 641.0 |
| 141 | 639.8 | 640.8 |
| 142 | 639.8 | 640.8 |
| 143 | 643.8 | 644.8 |
| 144 | 643.8 | 644.8 |
| 145 | 643.8 | 644.8 |
| 146 | 704.7 | 705.7 |
| 150 | 751.7 | 752.7 |
| 151 | 660.2 | 661.2 |
| 152 | 641.8 | 642.8 |
| 153 | 664.8 | 665.8 |
| 154 | 624.8 | 625.8 |
| 155 | 625.0 | 626.0 |
| 156 | 665.0 | 666.0 |
| 157 | 645.0 | 646.0 |
| 158 | 659.0 | 660.0 |
| 159 | 625.0 | 626.0 |
| 160 | 675.0 | 676.0 |
| 161 | 611.0 | 612.0 |
| 162 | 611.0 | 612.0 |
| 163 | 666.8 | 667.8 |
| 164 | 666.8 | 667.8 |
| 165 | 666.8 | 667.8 |
| 166 | 670.4 | 671.4 |
| 167 | 687.2 | 688.2 |
| 168 | 668.6 | 669.6 |
| 169 | 669.0 | 670.0 |
| 170 | 627.0 | 628.0 |
| 171 | 742.0 | 743.0 |
| 172 | 669.0 | 670.0 |
| 173 | 655.0 | 656.0 |
| 174 | 655.0 | 656.0 |
| 175 | 709.0 | 710.0 |
| 176 | 689.0 | 690.0 |
| 177 | 703.0 | 704.0 |
| 178 | 669.0 | 670.0 |
| 179 | 598.0 | 599.0 |
| 180 | 719.0 | 720.0 |
| 181 | 639.0 | 640.0 |
| 182 | 655.0 | 656.0 |
| 183 | 613.0 | 614.0 |
| 184 | 610.0 | 611.0 |
| 185 | 641.0 | 642.0 |
| 186 | 683.0 | 684.0 |
| 187 | 626.0 | 627.0 |
| 188 | 665.8 | 666.8 |
| 189 | 665.8 | 666.8 |
| 190 | 665.8 | 666.8 |
| 193 | 669.4 | 670.4 |
| 198 | 777.7 | 778.7 |
| 199 | 686.3 | 687.3 |
| 200 | 667.8 | 668.8 |
| 201 | 690.9 | 691.9 |
| 202 | 639.0 | 640.0 |
| 203 | 638.8 | 639.8 |
| 204 | 638.8 | 639.8 |
| 205 | 642.8 | 643.8 |
| 206 | 642.8 | 643.8 |
| 207 | 642.8 | 643.8 |
| 208 | 703.7 | 704.7 |
| 212 | 750.7 | 751.7 |
| 213 | 659.2 | 660.2 |
| 214 | 640.8 | 641.8 |
| 215 | 663.8 | 664.8 |
| 267 | 1248.5 | 1248.9 |
| 268 | 1336.6 | 1336.9 |
| 269 | 1476 | 1476.65 |
| 270 | 1248.5 | 1248.9 |
| 271 | 1491.7 | 1491.70 |
| 272 | 2048.4 | 2049 |
| 273 | 2577.1 | 2578 |

Example 3

Opioid Agonist Peptides Agonize MOR and DOR

The ability of opioid agonist peptides disclosed herein to agonize the μ-opioid receptor (MOR) and δ-opioid receptor (DOR) was determined. In addition, the gastric stability of the opioid agonist peptides was evaluated in simulated gastric fluid (SGF), simulated intestinal fluid (SIF), and plasma.

MOR and DOR Agonist cAMP Assays

The HitHunter® cAMP chemiluminescent assay kit (DiscoveRx, Cat #90-0075 SM25) was used to detect cAMP production in cAMP Hunter™ $G\alpha_i$ cell lines over expressing either Human-ORPM1 (Discoverx, Catalog #95-0107C2) or Human-ORPD1 (DiscoveRx, Catalog #95-0108C2). Opioid agonist binding to the $G\alpha_i$ receptors inhibits the intracellular cAMP accumulation induced by forskolin, which activates adenylate cyclase and increases intracellular levels of cAMP.

Cells were cultured in media consisting of Ham's F-12 Nutrient Mix (Life Technologies, Catalog #31765035), 10%

FBS (Life Technologies, Catalog #16140-071), 4 mM GlutaMAX (Life Technologies, Catalog #35050-061), 2 nM HEPES (Life Technologies), 100 ug/ml of Penn-Strep (Life Technologies) and 0.5 mg/ml Geneticin (Life Technologies, Catalog #10131-027). The cultures were maintained at 37° C. under 5% $CO_2$.

In preparation for cAMP assay, the cells were seeded at a density of 300,000 cells/ml in 100 ul of media/well in 96-well microplate. Wells that were designated for cAMP standards were left empty. After an overnight incubation to allow for cells to adhere to the plate, the media was replaced with 30 ul of cell assay buffer composed of 1×HBSS+10 mM HEPES.

Opioid agonist serial dilutions were prepared in separate dilution plate (11-point series of 3× (3-fold) dilution) in Cell Assay buffer, including 3× forskolin for $G\alpha_i$ target. For Hunter CHO-K1 OPRM1 or CHO-K1 OPRD1 $G\alpha_i$ Cell Lines, the final forskolin concentration was 20 uM.

15 ul of each 3× opioid agonist serial dilution was added in the presence of forskolin in duplicate to the designated wells. The final concentration of each dilution was at 3× of the final screening concentration. The assay plate was incubated for 30 min, at 37° C. under 5% $CO_2$.

Cellular cAMP concentrations were measured using the HitHunter cAMP Assay kit following the manufacturer's protocol. HitHunter cAMP assay is a gain-of-signal competitive immunoassay based on Enzyme Fragment Complementation (EFC) technology. The kit uses β-galactosidase (β-gal) enzyme split into Enzyme Donor (ED) and Enzyme Acceptor (EA). The cellular cAMP and ED-labelled cAMP compete for anti-cAMP antibody. Antibody-bound-ED-cAMP will not be able to complement with EA. When cellular cAMP level is high, it competes for the anti-cAMP antibody, thereby releasing ED-cAMP to complement with EA to produce a luminescent signal. The amount of signal is directly proportional to the amount of cAMP in cells and can be quantified using cAMP standards. The assay plates were read using a PerkinElmer Envision instrument to detect the chemiluminescence signal in each well (luminescence reader at 0.1 to 1 second/well). Data analysis was performed using Graphpad Prism 7. $EC_{50}$ was calculated by nonlinear regression, using the four-parameter hill equation.

SGF Assay

SGF was prepared by adding 20 mg NaCl, 32 mg porcine pepsin (MP Biochemicals, catalog 02102599), and 70 μl HCl to 10 ml water (final pH=2). Aliquots of SGF (0.5 ml each) were pre-warmed at 37° C. To start the reaction, 1 μl of opioid agonist peptide stock solution (10 mM in DMSO) was added to 0.5 ml SGF and thoroughly mixed such that the final peptide concentration was 20 μM. The reactions were incubated at 37° C. with gentle shaking.

At each timepoint (0, 15, 30, 60 min) 50 μl aliquots were removed and added to 200 ul of acetonitrile containing 0.1% formic acid to quench the reaction. Samples were stored at 4° C. until the end of the experiment and centrifuged at 10,000 rpm for 5 minutes. Aliquots of the supernatant were removed, diluted 1:1 into distilled water containing internal standard, and analyzed by LCMS/MS. The percent of the opioid agonist peptide remaining at each timepoint was calculated based on the peak area response ratio of the opioid agonist peptide to the internal standard. Time 0 was set to 100%, and all later timepoints were calculated relative to time 0. Half-lives were calculated by fitting to a first-order exponential decay equation using GraphPad.

SIF Assay

SIF was prepared by adding 6.8 g of monobasic potassium phosphate and 10.0 g of pancreatin to 1.0 L of water. After dissolution, the pH was adjusted to 6.8 using NaOH. DMSO stocks (2 mM) were prepared for each of the opioid agonist peptides. Aliquots of the DMSO solutions were dosed into 6 individual tubes, each containing 0.5 mL of SIF, which was pre-warmed to 37° C. The final opioid agonist peptide concentration was 20 μM. The vials were kept in a benchtop Thermomixer® for the duration of the experiment. At each timepoint (0, 5, 10, 20, 40, 60, or 360 minutes or 24 hours), 1.0 mL of acetonitrile containing 1% formic acid was added to one vial to terminate the reaction. Samples were stored at 4° C. until the end of the experiment. After the final timepoint was sampled, the tubes were mixed and then centrifuged at 3,000 rpm for 10 minutes. Aliquots of the supernatant were removed, diluted 1:1 into distilled water containing an internal standard, and analyzed by LCMS/MS. The percent of the opioid agonist peptide remaining at each timepoint was calculated based on the peak area response ratio of opioid agonist peptide to the internal standard. Time 0 was set to 100%, and all later timepoints were calculated relative to time 0. Half-lives were calculated by fitting to a first-order exponential decay equation using Graph pad.

Plasma Assay

Peptides of interest (20 uM) were incubated with pre-warmed mouse plasma (BioreclamationIVT) at 37° C. Aliquots were taken at various time points up to 24 hours (e.g. 0, 0.25, 1, 3, 6 and 24 hr), and immediately quenched with 4 volumes of organic solvent (acetonitrile/methanol (1:1) and 0.1% formic acid, containing 1 μM internal standard). Quenched samples were stored at 4° C. until the end of the experiment and centrifuged at 17,000 g for 15 minutes. The supernatant was diluted 1:1 with deionized water and analyzed using LC-MS. Percentage remaining at each time point was calculated based on the peak area ratio (analyte over internal standard) relative to the initial level at time zero. Half-lives were calculated by fitting to a first-order exponential decay equation using Graph Pad Prism.

The results of these assays are provided in Tables 3B-3F, which indicates the sequence of the peptide from N-terminus to C-terminus at positions numbered X1-X5 and the N-terminal and C-terminal moieties at $R^1$ and $R^2$, respectively, and which provides the EC50 values obtained from the cAMP assays for both DOR and MOR, as well as stability half-lives under the indicated conditions. Certain opioid agonist peptides were dual agonists of both MOR and DOR, whereas others were selective agonists of either MOR or DOR, or had greater agonist activity for either MOR or DOR. For EC50 values, * indicates ≤1.0;  indicates >1.0 to ≤10; * indicates >10 to ≤50; ** indicates >50 to ≤200; and *** indicates >200. For half-life values, * indicates ≤10.0;  indicates >10 to ≤360; * indicates >360 to ≤1440; and **** indicates >1440.

TABLE 3B

MOR and DOR cAMP agonist activity

| Seq. ID | R$^1$ | X1 | X2 | X3 | X4 | X5 | R$^2$ | MOR EC$_{50}$ | DOR EC$_{50}$ |
|---|---|---|---|---|---|---|---|---|---|
| 1 | H— | DMT | r | f | K | absent | OH | *** | ***** |
| 2 | H— | DMT | r | F | k | absent | NH$_2$ | * | ***** |
| 3 | H— | DMT | r | Bip | K | absent | NH$_2$ | **** | ***** |
| 4 | H— | DMT | r | H | K | absent | NH$_2$ | *** | ***** |
| 5 | H— | DMT | r | F | N(Me)Lys | absent | NH$_2$ | * | ***** |
| 7 | H— | DMT | r | F | K | absent | NH$_2$ | * | *** |
| 8 | H— | DMT | N(Me)-a | Aba | G | absent | NH$_2$ | * | * |
| 9 | H— | DMT | r | F | Sar | absent | NH$_2$ | * | ** |
| 10 | H— | DMT | N(Me)-a | F | Sar | absent | NH$_2$ | * | ** |
| 11 | H— | DMT | r | W | N(Me)bAla | absent | OH | * | *** |
| 12 | H— | DMT | r | Homo-F | N(Me)bAla | absent | OH | * | * |
| 13 | H— | DMT | r | 1-Nal | (NMeMe)bAla | absent | OH | * | ** |
| 14 | H— | DMT | r | F | (D)N(Me)Phe | absent | NH$_2$ | | *** |
| 15 | H— | DMT | r | F | alpha-MePhe | absent | NH$_2$ | | ** |
| 16 | H— | DMT | r | F | Phe(4-F) | absent | NH$_2$ | | *** |
| 17 | H— | DMT | r | F | Phe(3,4-diOMe) | absent | NH$_2$ | | ** |
| 18 | H— | DMT | r | F | HomoPhe | absent | NH$_2$ | | ** |
| 19 | H— | DMT | r | Phe(4-F) | Sar | absent | NH$_2$ | * | ** |
| 20 | H— | DMT | r | Phe(4-CN) | Sar | absent | NH$_2$ | ** | * |
| 21 | H— | DMT | r | Tic | Sar | absent | NH$_2$ | | ***** |
| 22 | H— | DMT | r | Phe(3,4-diCl) | Sar | absent | NH$_2$ | | *** |
| 23 | H— | DMT | r | BIP | Sar | absent | NH$_2$ | | * |
| 24 | H— | DMT | r | 4-tBu-Phe | Sar | absent | NH$_2$ | | ***** |
| 25 | H— | DMT | r | Phe(3,4-diOMe) | Sar | absent | NH$_2$ | | ***** |
| 26 | H— | DMT | r | DPA | Sar | absent | NH$_2$ | | ***** |
| 27 | H— | DMT | r | F | Octyl Gly | absent | NH$_2$ | | **** |
| 28 | H— | DMT | r | F | Nle | absent | NH$_2$ | | *** |
| 29 | H— | DMT | r | F | L | absent | NH$_2$ | | *** |
| 30 | H— | DMT | r | F | V | absent | NH$_2$ | | ** |
| 31 | H— | DMT | r | W | Nle | absent | NH$_2$ | | *** |
| 32 | H— | DMT | r | DPA | Sar | absent | NH$_2$ | | ***** |
| 33 | H— | DMT | r | G | DPA | absent | NH$_2$ | | ***** |
| 34 | H— | DMT | r | G | W | absent | NH$_2$ | | *** |
| 35 | H— | DMT | r | Sar | W | absent | NH$_2$ | | ***** |
| 36 | H— | DMT | r | F | DPA | absent | NH$_2$ | | *** |
| 37 | H— | DMT | a | G | F | Nle | NH$_2$ | * | * |
| 38 | H— | DMT | a | G | Phe(4-F) | G | NH$_2$ | * | * |
| 39 | H— | DMT | a | G | Phe(4-CN) | G | NH$_2$ | * | * |
| 40 | H— | DMT | a | G | Tic | G | NH$_2$ | | *** |
| 41 | H— | DMT | a | G | Phe(3,4-diCl) | G | NH$_2$ | * | * |
| 42 | H— | DMT | a | G | F | Sar | NH$_2$ | * | |
| 43 | H— | DMT | a | G | bhF | Sar | NH$_2$ | * | * |
| 44 | H— | DMT | dTic | F | Sar | absent | NH$_2$ | * | ** |
| 45 | H— | DMT | dTic | G | F | Sar | NH$_2$ | * | * |
| 46 | H— | DMT | a | hF | Sar | absent | NH$_2$ | * | * |
| 47 | H— | DMT | a | G | hF | Sar | NH$_2$ | * | ** |
| 48 | H— | DMT | a | hF | Nle | absent | NH$_2$ | * | * |
| 49 | H— | DMT | a | G | hF | Nle | NH$_2$ | * | ** |
| 50 | H— | bh-Tyr | a | G | bhF | Sar | NH$_2$ | ***** | ***** |
| 51 | H— | N(Me)-Tyr | a | G | bhF | Sar | NH$_2$ | ** | ***** |
| 52 | H— | Tyr(3-tBu) | a | G | bhF | Sar | NH$_2$ | **** | ***** |
| 53 | H— | (D)Tyr | a | G | bhF | Sar | NH$_2$ | ***** | ***** |
| 54 | H— | h-Tyr | a | G | bhF | Sar | NH$_2$ | ***** | ***** |
| 55 | H— | Tyr(3-Cl) | a | G | bhF | Sar | NH$_2$ | ** | *** |
| 56 | H— | meta-Tyr | a | G | bhF | Sar | NH$_2$ | ***** | ***** |
| 57 | H— | Tyr(3-F) | a | G | bhF | Sar | NH$_2$ | ** | ** |
| 58 | H— | Tyr(3-OH) | a | G | bhF | Sar | NH$_2$ | **** | **** |
| 59 | H— | Phe(4-NHCOCH$_3$) | a | G | bhF | Sar | NH$_2$ | *** | **** |
| 60 | H— | Phe(4-CONH$_2$) | a | G | bhF | Sar | NH$_2$ | ** | ** |
| 61 | H— | Tic(7-OH) | a | G | bhF | Sar | NH$_2$ | ***** | *** |
| 62 | H— | Tyr | a | G | bhF | Sar | NH$_2$ | ** | ** |
| 63 | H— | Trp(5-OH) | a | G | bhF | Sar | NH$_2$ | **** | **** |
| 64 | H— | DMT | a | Sar | bhF | Sar | NH$_2$ | ** | **** |
| 65 | H— | DMT | a | THP | bhF | Sar | NH$_2$ | | **** |
| 66 | H— | DMT | a | Ala | bhF | Sar | NH$_2$ | * | * |
| 67 | H— | DMT | a | Leu | bhF | Sar | NH$_2$ | * | *** |
| 68 | H— | DMT | a | ILeu | bhF | Sar | NH$_2$ | * | *** |
| 69 | H— | DMT | a | Val | bhF | Sar | NH$_2$ | | **** |
| 70 | H— | Phe(DMC)* | a | G | bhF | Sar | NH$_2$ | * | * |
| 71 | H— | Phe(4-(2-aminoethoxy) | a | G | bhF | Sar | NH$_2$ | | |
| 72 | H— | DMT | a | Aib | bhF | Sar | NH$_2$ | * | * |
| 73 | H— | DMT | a | bAla | bhF | Sar | NH$_2$ | | **** |
| 74 | H— | Phe(DMC) | G | G | bhF | Sar | NH$_2$ | * | * |

TABLE 3B-continued

MOR and DOR cAMP agonist activity

| Seq. ID | R[1] | X1 | X2 | X3 | X4 | X5 | R[2] | MOR EC$_{50}$ | DOR EC$_{50}$ |
|---|---|---|---|---|---|---|---|---|---|
| 75 | H— | Phe(DMC) | Aib | G | bhF | Sar | NH$_2$ | * | *** |
| 76 | H— | Phe(DMC) | (D)Thr | G | bhF | Sar | NH$_2$ | ** | * |
| 77 | H— | Phe(DMC) | (D)Asp | G | bhF | Sar | NH$_2$ | | * |
| 78 | H— | Phe(DMC) | N(Me)Arg | G | bhF | Sar | NH$_2$ | | **** |
| 79 | H— | Phe(DMC) | a | G | bhF | Sar | OH | * | * |
| 80 | H— | Phe(DMC) | A | G | bhF | Sar | OH | ** | **** |
| 81 | H— | DMT | G | G | bhF | Sar | NH$_2$ | * | * |
| 82 | H— | DMT | (D)Thr | G | bhF | Sar | NH$_2$ | * | * |
| 83 | H— | DMT | (D)Asp | G | bhF | Sar | NH$_2$ | * | * |
| 84 | H— | DMT | (D)Tyr | G | bhF | Sar | NH$_2$ | * | * |
| 85 | H— | Phe(DMC) | (D)Tyr | G | bhF | Sar | NH$_2$ | * | * |
| 86 | Ac | DMT | a | G | bhF | Sar | NH$_2$ | ** | *** |
| 87 | H— | DMT | a | G | bhF | Sar | OH | * | * |
| 88 | H— | DMT | A | G | bhF | Sar | OH | ** | *** |
| 89 | H— | Phe(4-COOH) | a | G | bhF | Sar | NH$_2$ | **** | **** |
| 90 | H— | DMT | Aib | G | bhF | Sar | NH$_2$ | * | ** |
| 91 | H— | DMT | N(Me)Arg | G | bhF | Sar | NH$_2$ | | **** |
| 92 | H— | Phe(DMC) | a | G | bhF | N(Me)Leu | OH | ** | * |
| 93 | H— | Phe(DMC) | a | G | bhF | N(Me)Ala | OH | * | * |
| 94 | H— | Phe(DMC) | a | G | bhF | Gly | NH$_2$ | * | ** |
| 95 | H— | Phe(DMC) | a | G | bhF | N(Me)Ile | OH | * | ** |
| 96 | H— | Phe(DMC) | a | G | bhF | N(Me)Val | OH | * | * |
| 97 | H— | Phe(DMC) | a | G | bhF | N(Me)Nva | OH | * | * |
| 98 | H— | Phe(DMC) | a | G | bhF | N(Me)cha | OH | ** | ** |
| 99 | H— | Phe(DMC) | a | G | bhF | N(Me)Phg | OH | * | * |
| 100 | H— | Phe(DMC) | a | G | bhF | N(Me)Phe | OH | ** | ** |
| 101 | H— | Phe(DMC) | a | G | bhF | N(Me)Nle | OH | ** | * |
| 102 | H— | Phe(DMC) | a | G | bhF | N(Me)Tyr | OH | * | * |
| 103 | H— | Phe(DMC) | Tic | G | bhF | Sar | NH$_2$ | **** | **** |
| 104 | H— | DMT | Tic | G | bhF | Sar | NH$_2$ | **** | **** |
| 105 | H— | Phe(4-tetrazolyl) | a | G | bhF | Sar | NH$_2$ | **** | **** |
| 106 | H— | Phe(DMC) | a | G | bhF | N(Me)Trp | OH | ** | ** |
| 107 | H— | DMT | a | G | Tic | Sar | NH$_2$ | | *** |
| 108 | H— | Phe(DMC) | a | G | Tic | Sar | NH$_2$ | ** | *** |
| 109 | H— | Phe(DMC) | a | G | bhF(3-Cl) | Sar | NH$_2$ | | |
| 110 | H— | Phe(DMC) | a | G | bhF(4-I) | Sar | NH$_2$ | | |
| 111 | H— | DMT | a | G | bhF | N(Me)Ala | OH | * | * |
| 112 | H— | DMT | a | G | bhF | Gly | NH$_2$ | * | * |
| 113 | H— | DMT | a | G | bhF | N(Me)ILe | OH | * | * |
| 114 | H— | DMT | a | G | bhF | 2-Nal | NH$_2$ | ** | ** |
| 115 | H— | DMT | a | G | bhF | N(ocytyl)Gly | NH$_2$ | *** | *** |
| 116 | H— | DMT | a | G | bhF | N(isopentyl)Gly | NH$_2$ | * | * |
| 117 | H— | DMT | a | G | bhF | N(3-isopropyloxypropyl)Gly | NH$_2$ | * | * |
| 118 | H— | DMT | a | G | bhF | N(benzyl)Gly | NH$_2$ | * | * |
| 119 | H— | DMT | a | G | bhF | N(cyclohexylmethyl)Gly | NH$_2$ | * | ** |
| 120 | H— | DMT | a | G | bhF | N(3-propionic acid)Gly | NH$_2$ | * | * |
| 121 | H— | DMT | a | G | bhF | N(Phenethyl)Gly | NH$_2$ | * | * |
| 122 | H— | DMT | a | G | bhF | N(Trifluoroethyl)Gly | NH$_2$ | * | * |
| 123 | H— | DMT | a | G | bhF | N(Cyclohexyl)Gly | NH$_2$ | * | * |
| 124 | H— | DMT | a | G | bhF | N(amyl)Gly | NH$_2$ | * | * |
| 125 | H— | DMT | a | G | bhF | N(hexadecyl)Gly | NH$_2$ | ** | ** |
| 126 | H— | Phe(DMC) | a | G | bhF(2-Me) | N(Me)Leu | OH | | |
| 127 | H— | Phe(DMC) | a | G | bhF(3-Me) | N(Me)Leu | OH | | |
| 128 | H— | Phe(DMC) | a | G | bhF(4Me) | N(Me)Leu | OH | | |
| 129 | H— | Phe(DMC) | a | G | bhF(2-F) | N(Me)Nle | OH | | |
| 130 | H— | Phe(DMC) | a | G | bhF(3-F) | N(Me)Nle | OH | | |
| 131 | H— | Phe(DMC) | a | G | bhF(4-F) | N(Me)Leu | OH | | |
| 132 | H— | Phe(DMC) | a | G | bhF(2-Br) | N(Me)Nle | OH | | |
| 133 | H— | Phe(DMC) | a | G | bhF(3-Br) | N(Me)Nle | OH | | |
| 134 | H— | Phe(DMC) | a | G | bhF(4-Br) | N(Me)Nle | OH | | |
| 135 | H— | Phe(DMC) | a | G | bhF(4-NO2) | N(Me)Nle | OH | | |
| 136 | H— | Phe(DMC) | a | G | bhF(4-I) | N(Me)Nle | OH | * | * |
| 137 | H— | Phe(DMC) | a | G | bhF(3-Cl) | N(Me)Leu | OH | | |
| 138 | H— | Phe(DMC) | a | G | bhF(4-OH) or bhTyr | N(Me)Leu | OH | | |
| 139 | H— | Phe(DMC) | a | G | bhW | N(Me)Nle | OH | * | ** |
| 140 | H— | DMT | a | G | bhF(2-Me) | N(Me)Nle | OH | * | * |
| 141 | H— | DMT | a | G | bhF(3-Me) | N(Me)Nle | OH | * | * |
| 142 | H— | DMT | a | G | bhF(4Me) | N(Me)Nle | OH | ** | * |
| 143 | H— | DMT | a | G | bhF(2-F) | N(Me)Nle | OH | * | * |
| 144 | H— | DMT | a | G | bhF(3-F) | N(Me)Nle | OH | * | * |
| 145 | H— | DMT | a | G | bhF(4-F) | N(Me)Nle | OH | * | * |

TABLE 3B-continued

MOR and DOR cAMP agonist activity

| Seq. ID | R¹ | X1 | X2 | X3 | X4 | X5 | R² | MOR EC$_{50}$ | DOR EC$_{50}$ |
|---|---|---|---|---|---|---|---|---|---|
| 146 | H— | DMT | a | G | bhF(2-Br) | N(Me)Nle | OH | * | * |
| 147 | H— | DMT | a | G | bhF(3-Br) | N(Me)Nle | OH | | |
| 148 | H— | DMT | a | G | bhF(4-Br) | N(Me)Nle | OH | | |
| 149 | H— | DMT | a | G | bhF(4-NO2) | N(Me)Nle | OH | | |
| 150 | H— | DMT | a | G | bhF(4-I) | N(Me)Nle | OH | * | * |
| 151 | H— | DMT | a | G | bhF(3-Cl) | N(Me)Nle | OH | * | * |
| 152 | H— | DMT | a | G | bhF(4-OH) | N(Me)Nle | OH | * | * |
| 153 | H— | DMT | a | G | bhW | N(Me)Nle | OH | ** | * |

TABLE 3C

MOR and DOR agonist activity of additional opioid agonist peptides

| Seq. ID | R¹ | X1 | X2 | X3 | X4 | X5 | R² | MOR EC$_{50}$ nM | DOR EC$_{50}$ nM |
|---|---|---|---|---|---|---|---|---|---|
| 154 | H— | DMT | a | G | (D)N(Me)Phe | N(Me)Nle | OH | * | * |
| 155 | H— | DMT | a | G | bhF | N(Me)-Leu | OH | * | * |
| 156 | H— | DMT | a | G | bhF | N(Me)-Cha | OH | * | ** |
| 157 | H— | DMT | a | G | bhF | N(Me)-Phg | OH | * | * |
| 158 | H— | DMT | a | G | bhF | N(Me)-Phe | OH | * | * |
| 159 | H— | DMT | a | G | bhF | N(Me)-Nle | OH | * | * |
| 160 | H— | DMT | a | G | bhF | N(Me)-Tyr | OH | * | * |
| 161 | H— | DMT | a | G | bhF | N(Me)-Val | OH | * | * |
| 162 | H— | DMT | a | G | bhF | N(Me)-Nva | OH | * | * |
| 163 | H— | Phe(DMC) | a | G | bhF (2-Me) | N(Me)Nle | OH | | ** |
| 164 | H— | Phe(DMC) | a | G | bhF (3-Me) | N(Me)Nle | OH | * | * |
| 165 | H— | Phe(DMC) | a | G | bhF (4-Me) | N(Me)Nle | OH | * | * |
| 166 | H— | Phe(DMC) | a | G | bhF (4-F) | N(Me)Nle | OH | * | * |
| 167 | H— | Phe(DMC) | a | G | bhF (3-Cl) | N(Me)Nle | OH | * | * |
| 168 | H— | Phe(DMC) | a | G | bhY | N(Me)Nle | OH | ** | * |
| 169 | H— | DMT | (D)Asp | G | bhF | N(Me)-Leu | OH | * | * |
| 170 | H— | DMT | (D)Asp | G | bhF | N(Me)-Ala | OH | * | * |
| 171 | H— | DMT | (D)Asp | G | bhF | N(Me)-Trp | OH | * | * |
| 172 | H— | DMT | (D)Asp | G | bhF | N(Me)-Ile | OH | * | * |
| 173 | H— | DMT | (D)Asp | G | bhF | N(Me)-Val | OH | * | * |
| 174 | H— | DMT | (D)Asp | G | bhF | N(Me)-Nva | OH | * | * |
| 175 | H— | DMT | (D)Asp | G | bhF | N(Me)-Cha | OH | * | * |
| 176 | H— | DMT | (D)Asp | G | bhF | N(Me)-Phg | OH | * | * |
| 177 | H— | DMT | (D)Asp | G | bhF | N(Me)-Phe | OH | * | * |
| 178 | H— | DMT | (D)Asp | G | bhF | N(Me)-Nle | OH | * | * |
| 179 | H— | DMT | (D)Asp | G | bhF | Gly | NH$_2$ | * | * |
| 180 | H— | DMT | (D)Asp | G | bhF | N(Me)-Tyr | OH | * | * |
| 181 | H— | DMT | a | G | bhF(2-Me) | N(Me)Nle | NH$_2$ | | |
| 182 | H— | DMT | (D)Thr | G | bhF | N(Me)-Ile | OH | * | * |
| 183 | H— | DMT | (D)Thr | G | bhF | N(Me)-Ala | OH | * | * |
| 184 | H— | DMT | a | G | bhF | N(Me)-Nva | NH$_2$ | * | * |
| 185 | H— | DMT | (D)Glu | G | bhF | N(Me)-Ala | OH | ** | * |
| 186 | H— | DMT | (D)Glu | G | bhF | N(Me)-Ile | OH | ** | * |
| 187 | H— | DMT | (D)Glu | G | bhF | Sar | NH$_2$ | * | ** |

*Phe(DMC)—Phe(2,6-dimethyl-4-CONH$_2$)

TABLE 3D

Gastric and Plasma stability of opioid agonist peptides

| Seq. ID | SGF half-life (min) | SIF half-life (min) | Plasma half-life (min) |
|---|---|---|---|
| 37 | ** | * | *** |
| 43 | **** | *** | *** |
| 50 | | *** | |
| 51 | | *** | |
| 52 | | *** | |
| 53 | | *** | |
| 54 | | *** | |
| 55 | | *** | |
| 56 | | *** | |
| 57 | **** | *** | |
| 58 | | *** | |
| 66 | ** | **** | |
| 70 | ** | **** | |
| 72 | ** | **** | |
| 73 | ** | **** | |
| 76 | ** | **** | |
| 79 | **** | **** | |
| 81 | **** | **** | |

TABLE 3D-continued

Gastric and Plasma stability of opioid agonist peptides

| Seq. ID | SGF half-life (min) | SIF half-life (min) | Plasma half-life (min) |
|---|---|---|---|
| 82 | **** | **** | |
| 83 | **** | **** | **** |
| 84 | **** | **** | |
| 85 | *** | **** | |
| 87 | *** | **** | |
| 92 | **** | **** | |
| 93 | **** | **** | |
| 96 | **** | **** | |
| 99 | **** | **** | |
| 101 | **** | **** | |
| 102 | **** | **** | |
| 111 | **** | **** | |
| 112 | **** | **** | |
| 116 | **** | **** | |
| 117 | **** | **** | |
| 118 | **** | **** | |
| 140 | *** | *** | |
| 155 | **** | **** | |
| 157 | | **** | |
| 159 | **** | **** | |
| 161 | **** | **** | |
| 165 | **** | ** | |
| 166 | **** | **** | |
| 167 | **** | **** | |
| 179 | **** | **** | |

TABLE 3E

Additional opioid agonist peptides.

| Seq. ID | $R^1$ | X1 | X2 | X3 | X4 | X5 | $R^2$ |
|---|---|---|---|---|---|---|---|
| 188 | H— | Phe(DMC) | a | G | bhF(2-Me) | N(Me)Leu | $NH_2$ |
| 189 | H— | Phe(DMC) | a | G | bhF(3-Me) | N(Me)Leu | $NH_2$ |
| 190 | H— | Phe(DMC) | a | G | bhF(4-Me) | N(Me)Leu | $NH_2$ |
| 191 | H— | Phe(DMC) | a | G | bhF(2-F) | N(Me)Leu | $NH_2$ |
| 192 | H— | Phe(DMC) | a | G | bhF(3-F) | N(Me)Leu | $NH_2$ |
| 193 | H— | Phe(DMC) | a | G | bhF(4-F) | N(Me)Leu | $NH_2$ |
| 194 | H— | Phe(DMC) | a | G | bhF(2-Br) | N(Me)Leu | $NH_2$ |
| 195 | H— | Phe(DMC) | a | G | bhF(3-Br) | N(Me)Leu | $NH_2$ |
| 196 | H— | Phe(DMC) | a | G | bhF(4-Br) | N(Me)Leu | $NH_2$ |
| 197 | H— | Phe(DMC) | a | G | bhF(4-NO2) | N(Me)Leu | $NH_2$ |
| 198 | H— | Phe(DMC) | a | G | bhF(4-I) | N(Me)Leu | $NH_2$ |
| 199 | H— | Phe(DMC) | a | G | bhF(3-Cl) | N(Me)Leu | $NH_2$ |
| 200 | H— | Phe(DMC) | a | G | bhF(4-OH) | N(Me)Leu | $NH_2$ |
| 201 | H— | Phe(DMC) | a | G | bhW | N(Me)Leu | $NH_2$ |
| 202 | H— | DMT | a | G | bhF(2-Me) | N(Me)Leu | $NH_2$ |
| 203 | H— | DMT | a | G | bhF(3-Me) | N(Me)Leu | $NH_2$ |
| 204 | H— | DMT | a | G | bhF(4Me) | N(Me)Leu | $NH_2$ |
| 205 | H— | DMT | a | G | bhF(2-F) | N(Me)Leu | $NH_2$ |
| 206 | H— | DMT | a | G | bhF(3-F) | N(Me)Leu | $NH_2$ |
| 207 | H— | DMT | a | G | bhF(4-F) | N(Me)Leu | $NH_2$ |
| 208 | H— | DMT | a | G | bhF(2-Br) | N(Me)Leu | $NH_2$ |
| 209 | H— | DMT | a | G | bhF(3-Br) | N(Me)Leu | $NH_2$ |
| 210 | H— | DMT | a | G | bhF(4-Br) | N(Me)Leu | $NH_2$ |
| 211 | H— | DMT | a | G | bhF(4-NO2) | N(Me)Leu | $NH_2$ |
| 212 | H— | DMT | a | G | bhF(4-I) | N(Me)Leu | $NH_2$ |
| 213 | H— | DMT | a | G | bhF(3-Cl) | N(Me)Leu | $NH_2$ |
| 214 | H— | DMT | a | G | bhF(4-OH) | N(Me)Leu | $NH_2$ |
| 215 | H— | DMT | a | G | bhW | N(Me)Leu | $NH_2$ |
| 216 | H— | Phe(DMC) | a | G | bhF | N(Me)Leu | $NH_2$ |
| 217 | H— | Phe(DMC) | a | G | bhF | N(Me)Ala | $NH_2$ |
| 218 | H— | Phe(DMC) | a | G | bhF | N(Me)Ile | $NH_2$ |
| 219 | H— | Phe(DMC) | a | G | bhF | N(Me)Val | $NH_2$ |
| 220 | H— | Phe(DMC) | a | G | bhF | N(Me)Nva | $NH_2$ |
| 221 | H— | Phe(DMC) | a | G | bhF | N(Me)cha | $NH_2$ |
| 222 | H— | Phe(DMC) | a | G | bhF | N(Me)Phg | $NH_2$ |
| 223 | H— | Phe(DMC) | a | G | bhF | N(Me)Phe | $NH_2$ |
| 224 | H— | Phe(DMC) | a | G | bhF | N(Me)Nle | $NH_2$ |
| 225 | H— | Phe(DMC) | a | G | bhF | N(Me)Tyr | $NH_2$ |
| 226 | H— | Phe(DMC) | a | G | bhF | N(Me)Trp | $NH_2$ |
| 227 | H— | DMT | a | G | bhF | N(Me)Ala | $NH_2$ |
| 228 | H— | DMT | a | G | bhF | Gly | OH |
| 229 | H— | DMT | a | G | bhF | N(Me)ILe | $NH_2$ |
| 230 | H— | DMT | a | G | (D)N(Me)Phe | N(Me)Nle | $NH_2$ |
| 231 | H— | DMT | a | G | bhF | N(Me)-Leu | $NH_2$ |
| 232 | H— | DMT | a | G | bhF | N(Me)-Cha | $NH_2$ |
| 233 | H— | DMT | a | G | bhF | N(Me)-Phg | $NH_2$ |
| 234 | H— | DMT | a | G | bhF | N(Me)-Phe | $NH_2$ |
| 235 | H— | DMT | a | G | bhF | N(Me)-Nle | $NH_2$ |
| 236 | H— | DMT | a | G | bhF | N(Me)-Tyr | $NH_2$ |
| 237 | H— | DMT | a | G | bhF | N(Me)-Val | $NH_2$ |
| 238 | H— | DMT | (D)Thr | G | bhF | N(Me)-Nva | OH |
| 239 | H— | Phe(DMC) | (D)Thr | G | bhF(2-Me) | N(Me)-Leu | OH |

TABLE 3E-continued

Additional opioid agonist peptides.

| Seq. ID | R¹ | X1 | X2 | X3 | X4 | X5 | R² |
|---|---|---|---|---|---|---|---|
| 240 | H— | Phe(DMC) | (D)Thr | G | bhF(3-Me) | N(Me)-Leu | OH |
| 241 | H— | Phe(DMC) | (D)Thr | G | bhF(4-Me) | N(Me)-Leu | OH |
| 242 | H— | Phe(DMC) | a | G | bhF(2-F) | N(Me)-Leu | OH |
| 243 | H— | Phe(DMC) | a | G | bhF(3-F) | N(Me)-Leu | OH |
| 244 | H— | Phe(DMC) | (D)Thr | G | bhF(4-F) | N(Me)-Leu | OH |
| 245 | H— | Phe(DMC) | a | G | bhF(2-Br) | N(Me)-Leu | OH |
| 246 | H— | Phe(DMC) | a | G | bhF(3-Br) | N(Me)-Leu | OH |
| 247 | H— | Phe(DMC) | a | G | bhF(4-Br) | N(Me)-Leu | OH |
| 248 | H— | Phe(DMC) | a | G | bhF(4-NO2) | N(Me)-Leu | OH |
| 249 | H— | Phe(DMC) | a | G | bhF(4-I) | N(Me)-Leu | OH |
| 250 | H— | Phe(DMC) | (D)Thr | G | bhF(3-Cl) | N(Me)-Leu | OH |
| 251 | H— | Phe(DMC) | (D)Thr | G | bhF(4-OH) or bhTyr | N(Me)-Leu | OH |
| 252 | H— | Phe(DMC) | a | G | bhW | N(Me)-Leu | OH |
| 253 | H— | DMT | a | G | bhF(2-Me) | N(Me)-Leu | OH |
| 254 | H— | DMT | a | G | bhF(3-Me) | N(Me)-Leu | OH |
| 255 | H— | DMT | a | G | bhF(4Me) | N(Me)-Leu | OH |
| 256 | H— | DMT | a | G | bhF(2-F) | N(Me)-Leu | OH |
| 257 | H— | DMT | a | G | bhF(3-F) | N(Me)-Leu | OH |
| 258 | H— | DMT | a | G | bhF(4-F) | N(Me)-Leu | OH |
| 259 | H— | DMT | a | G | bhF(2-Br) | N(Me)-Leu | OH |
| 260 | H— | DMT | a | G | bhF(3-Br) | N(Me)-Leu | OH |
| 261 | H— | DMT | a | G | bhF(4-Br) | N(Me)-Leu | OH |
| 262 | H— | DMT | a | G | bhF(4-NO2) | N(Me)-Leu | OH |
| 263 | H— | DMT | a | G | bbF(4-I) | N(Me)-Leu | OH |
| 264 | H— | DMT | a | G | bhF(3-Cl) | N(Me)-Leu | OH |
| 265 | H— | DMT | a | G | bhF(4-OH) | N(Me)-Leu | OH |
| 266 | H— | DMT | a | G | bhW | N(Me)-Leu | OH |

TABLE 3F

MOR and DOR agonist activity of additional opioid agonist peptide dimers having the indicated structures shown below.
R¹-X1-X2-X3-X4-X5-LINKER-X5-X4-X3-X2-X1-R¹ (Dimer A)
R¹-X1-X2-X3-X4-X5-Lys-LINKER-Lys-X5-X4-X3-X2-X1-R¹ (Dimer B)
R¹-X1-X2-X3-X4-X5-(D)Lys-LINKER-(D)Lys-X5-X4-X3-X2-X1-R¹ (Dimer C)

| Seq. ID | R¹ | X1 | X2 | X3 | X4 | X5 | Linker | MOR EC$_{50}$ | DOR EC$_{50}$ |
|---|---|---|---|---|---|---|---|---|---|
| 267 | H— | DMT | a | G | bhF | Sar | lysine (Dimer A) | * | * |
| 268 | H— | DMT | a | G | bhF | NMe-Ala | lysine (Dimer A) | * | * |
| 269 | H— | DMT | a | G | bhF | NMe-Ile | lysine (Dimer A) | ** | ** |
| 270 | H— | DMT | a | G | bhF | Sar | D-lysine (Dimer A) | ** | ** |
| 271 | H— | DMT | a | G | bhF | Sar | DIG (Dimer C) | ** | ** |
| 272 | H— | DMT | a | G | bhF | Sar | PEG13 (Dimer B) | ** | ** |
| 273 | H— | DMT | a | G | bhF | Sar | PEG25 (Dimer B) | ** | ** |

Example 4

Opioid Agonist Peptides Inhibit Gastro Intestinal Motility

The ability of orally administered opioid agonist peptides disclosed herein to inhibit gastro intestinal mobility was demonstrated using an animal model based on a charcoal meal test assay.

Gastro Intestinal Motility Charcoal Transit Assay

Animals were treated with 0.2 mL croton oil 96 and 72 hours before the gastro intestinal transit (GIT) assay. Animals were fasted overnight prior to charcoal meal dosing. Test and control articles were administered (PO, IP) followed by an oral dose of aqueous suspension of 5% charcoal in 10% gum arabic. Three illustrative peptides disclosed herein were tested, Peptide A (SEQ ID NO:43), Peptide B (SEQ ID NO:66) and Peptide C (SEQ ID NO:70). Charcoal meal test were given 30 min post-test article dose. Twenty minutes after administration of the charcoal test meal, animals were euthanized via $CO_2$ inhalation followed by cervical dislocation, and the small and large intestines were examined to evaluate GI transit and motility. GI transit is expressed as a percentage of the distance traveled by the charcoal test meal divided by the length of the intestine.

The three opioid agonist peptides tested were all MOR and DOR agonists, although they showed greater agonism of MOR as compared to DOR. All three of the opioid agonist peptides had a half-life in SIF greater than 1290 minutes. In addition, all three of the opioid agonist peptides inhibited gastrointestinal (GI) motility; Peptide A, orally dosed at 30 mg/Kg, inhibited GI mobility by 59%, whereas Peptide B and Peptide C, both orally dosed at 20 mg/Kg, inhibited GI mobility by 31% and 54%, respectively. Table 4 summarizes this date; for EC50 values, * indicates ≤1.0; for SIF half-life values, **** indicates >1290; for ratio, * indicates between 0.1 and 0.3 and ** indicates between 0.3 and 0.6; and for % inhibition of GI motility, * indicates between 30% and 50% and ** indicates between 50% and 100%.

TABLE 4

MOR and DOR agonist activity, gastric stability, and inhibition of gastric motility of opioid agonist peptides

| Peptide | MOR cAMP (EC50 nM) | DOR cAMP (EC50 nM) | Ratio (MOR EC50/DOR EC50) | SIF (min) | % I of GI motility |
|---|---|---|---|---|---|
| Peptide A | * | * | * | **** | ** |
| Peptide B | * | * | * | **** | * |
| Peptide C | * | * | ** | **** | ** |

This date demonstrates these peptides ability to agonize the MOR and DOR pathways, their stability in simulated intestinal fluid (SIF), and their ability to inhibit gastro intestinal motility in vivo when orally administered.

The inhibition of small intestine motility by orally administered Peptide A was compared to the inhibition of small intestine motility by orally administered eluxadoline. As shown in FIG. 1A, Peptide A showed slightly greater inhibition of small intestine motility at all doses tested as compared to eluxadoline. Similarly, Peptide A showed greater inhibition of GI transit at all doses tested as compared to eluxadoline (FIGS. 1B and 1C).

Example 5

Opioid Agonist Peptides Reduce Pain

Figure 3B:
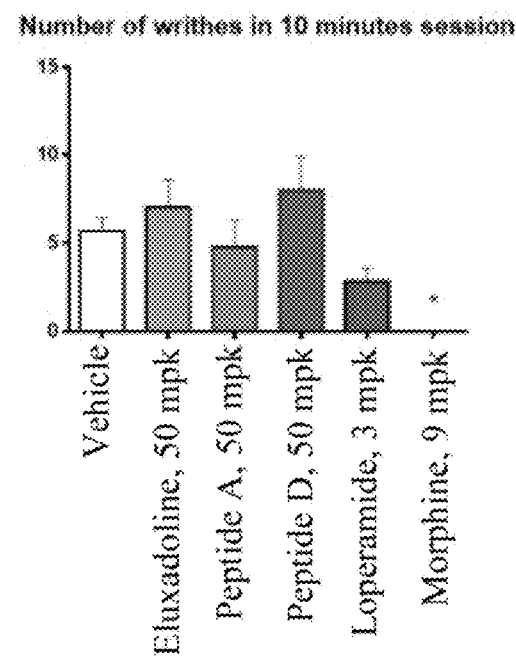

The ability of orally administered opioid agonist peptides disclosed herein to reduce pain was demonstrated using an animal pain model.
Acetic Acid or Acetylcholine Writhing Assay
Animals were fasted overnight prior to the start of the assay. Test and control article doses, ranging from 3-50 mg/kg, were administered (PO) followed by an IP injection of acetic acid (1.0%) or acetylcholine (10 mg/kg), and immediately placed in a viewing chamber. The animals were observed for a total of 10 minutes for the presence or absence of abdominal constriction response, beginning immediately after administration of the acetic acid or acetylcholine. Writhing (abdominal constriction) was defined as a contraction of the abdominal musculature accompanied by arching of the back and extension of the limbs. Latency to first writhe and total number of writhes were recorded. Test articles included oral eluxadoline and two illustrative opioid peptides disclosed herein, Peptide A and Peptide D; and control articles included loperamide and morphine The results of one writhing study are provided in FIGS. 2A and 2B. These data demonstrate that the Peptide A opioid agonist significantly reduced visceral pain at 30 mg/kg and 10 mg/kg. Loperamide served as a positive control. The effects of Peptide A and Peptide D were also compared to Eluxadoline. The results of this writhing study are provided in FIGS. 3A and 3B. The positive effect of Peptide A indicates the advantages associated with dual agonism of MOR and DOR, e.g., as compared to eluxadoline, a MOR agonist that showed little effect on pain. Loperamide and morphine served as positive controls.

All publications and patent applications described herein are hereby incorporated by reference in their entireties.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of inhibiting or reducing pain or gastrointestinal motility in a subject in need thereof, comprising providing to the subject an effective amount of an opioid agonist peptide comprising or consisting of an amino acid sequence of Formula Ia:

X1-X2-X3-X4-X5 (Formula Ia)    (SEQ ID NO: 357)

or a pharmaceutically acceptable salt or solvate thereof, wherein:
X1 is Tyr, DMT, or Phe(4-COX);
X2 is any amino acid;
X3 is any amino acid;
X4 is Sar, or bhF unsubstituted or substituted with 2-Me, 3-Me, 4-Me, 2-F, 3-F, 4-F, 2-Cl, 3-Cl, 4-Cl, 2-OH, 3-OH, or 4-OH; and
X5 is absent or any amino acid;
wherein DMT is 2,6-dimethyltyrosine;
Phe(4-COX) is substituted or unsubstituted

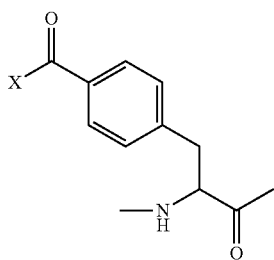

wherein X is substituted or unsubstituted OH or $NH_2$; and
provided that when X1 is Tyr; then X4 is bhF unsubstituted or substituted with 2-Me, 3-Me, 4-Me, 2-F, 3-F, 4-F, 2-Cl, 3-Cl, 4-Cl, 2-OH, 3-OH, or 4-OH, and X5 is N-methylamino acid.

2. The method of claim 1, wherein the peptide is according to Formula XIIIa, XIIIb, or XIIIc:

$R^1$-DMT-X2-X3-bhF-X5-$R^2$ (XIIIa);    (SEQ ID NO: 343)

$R^1$-Phe(4-COX)-X2-X3-bhF-X5-$R^2$ (XIIIb);    (SEQ ID NO: 344)
or $R^1$-Tyr-X2-X3-bhF-X5-$R^2$ (XIIIc);    (SEQ ID NO: 345)

wherein DMT, Phe(4-COX), X2, X3 and X5 are as described in claim 1; bhF is unsubstituted or substituted with 2-Me, 3-Me, 4-Me, 2-F, 3-F, 4-F, 2-Cl, 3-Cl, 4-Cl, 2-OH, 3-OH, or 4-OH; $R^1$ is H or acetyl; and $R^2$ is OH or $NH_2$;
provided that when the peptide is according to formula XIIIc, then X5 is a N-methylamino acid.

3. The method of claim 1, wherein X3 is (D)Phe, Phe, Bip, His, Aba, Trp, homo-Phe, 1-Nal, Phe(4-F), Phe(4-CN), Tic, Phe(3,4-dichloro), Phe(4-tBu), Phe(3,4-dimethoxy), DPA, Gly, Sar, THP, Ala, Leu, Ile, Val, Aib, or Ala.

4. The method of claim 1, wherein the amino acid sequence is according to Formula XIVa, XIVb, or XIVc:

$R^1$-DMT-X2-G-bhF-X5-$R^2$ (XIVa);    (SEQ ID NO: 346)

$R^1$-Phe(DMC)-X2-G-bhF-X5-$R^2$ (XIVb);    (SEQ ID NO: 347)
or $R^1$-Tyr-X2-G-bhF-X5-$R^2$ (XIVc)    (SEQ ID NO: 348)

wherein Phe(DMC) is Phe(2,6-dimethyl-4-$CONH_2$); $R^1$ is H or acetyl; and $R^2$ is OH or $NH_2$.

5. The method of claim 1, wherein X2 is (D)Glu, (D)Arg, N(Me)-(D)Ala, (D)Ala, (D)Tic, (D)Lys, (D)Orn, (D)Thr, (D)Asp, or (D)Tyr.

6. The method of claim 1, wherein the amino acid sequence is according to Formula XVa, XVb, XVc, XVd, XVIa, XVIb, XVIc, or XVId:

$R^1$-DMT-(D)Ala-G-bhF-X5-$R^2$ (XVa);    (SEQ ID NO: 349)

$R^1$-DMT-(D)Asp-G-bhF-X5-$R^2$ (XVb);    (SEQ ID NO: 350)

$R^1$-DMT-(D)Thr-G-bhF-X5-$R^2$ (XVc);    (SEQ ID NO: 351)

$R^1$-DMT-(D)Glu-G-bhF-X5-$R^2$ (XVd);    (SEQ ID NO: 352)

$R^1$-Phe(DMC)-(D)Ala-G-bhF-X5-$R^2$ (XVIa);    (SEQ ID NO: 353)

$R^1$-Phe(DMC)-(D)Asp-G-bhF-X5-$R^2$ (XVIb);    (SEQ ID NO: 354)

$R^1$-Phe(DMC)-(D)Thr-G-bhF-X5-$R^2$ (XVIc);    (SEQ ID NO: 355)

$R^1$-Phe(DMC)-(D)Glu-G-bhF-X5-$R^2$ (XVId)    (SEQ ID NO: 356)

wherein $R^1$ is H or acetyl; and $R^2$ is OH or $NH_2$.

7. The method of claim 1, wherein X5 is (D)Glu, (D)Arg, N(Me)-(D)Ala, (D)Ala, (D)Tic, (D)Lys, (D)Orn, (D)Thr, (D)Asp, (D)Tyr, Sar, N(Me)Phg, N(Me)Cha, N(Me)Tyr, N(Me)Nle, N(Me)Ile, N(Me)Ala, N(Me)Val, N(Me)Leu, or N(Me)Phe.

8. The method of claim 1, wherein the amino acid sequence is according to Formula XVIIa, XVIIb, XVIIc, XVIId, XVIIe, XVIIf, XVIIg, XVIIh, XVIIi, XVIIj, XVIIk, XVIII, XVIIIa, XVIIIb, XVIIIc, XVIIId, XVIIIe, XVIIIf, XVIIIg, XVIIIh, XVIIIi, XVIIIj, XVIIIk, or XVIIIl:

$R^1$-DMT-(D)Ala-G-bhF-Sar-$R^2$ (XVIIa);    (SEQ ID NO: 43)

$R^1$-DMT-(D)Asp-G-bhF-Sar-$R^2$ (XVIIb);    (SEQ ID NO: 82)

$R^1$-DMT-(D)Thr-G-bhF-Sar-$R^2$ (XVIIc);    (SEQ ID NO: 82)

$R^1$-DMT-(D)Glu-G-bhF-Sar-$R^2$ (XVIId);    (SEQ ID NO: 187)

$R^1$-DMT-(D)Ala-G-bhF-NMeAla-$R^2$ (XVIIe);    (SEQ ID NO: 111)

$R^1$-DMT-(D)Asp-G-bhF-NMeAla-$R^2$ (XVIIf);    (SEQ ID NO: 170)

-continued

```
                             (SEQ ID NO: 183)
R¹-DMT-(D)Thr-G-bhF-NMeAla-R² (XVIIg);

(SEQ ID NO: 185)
R¹-DMT-(D)Glu-G-bhF-NMeAla-R² (XVIIh);

(SEQ ID NO: 113)
R¹-DMT-(D)Ala-G-bhF-NMeIle-R² (XVIIi);

(SEQ ID NO: 172)
R¹-DMT-(D)Asp-G-bhF-NMeIle-R² (XVIIj);

(SEQ ID NO: 182)
R¹-DMT-(D)Thr-G-bhF-NMeIle-R² (XVIIk);

(SEQ ID NO: 186)
R¹-DMT-(D)Glu-G-bhF-NMeIle-R² (XVIIl);

(SEQ ID NO: 70)
R¹-Phe(DMC)-(D)Ala-G-bhF-Sar-R² (XVIIIa);

(SEQ ID NO: 77)
R¹-Phe(DMC)-(D)Asp-G-bhF-Sar-R² (XVIIIb);

(SEQ ID NO: 76)
R¹-Phe(DMC)-(D)Thr-G-bhF-Sar-R² (XVIIIc);

(SEQ ID NO: 330)
R¹-Phe(DMC)-(D)Glu-G-bhF-Sar-R² (XVIIId);

(SEQ ID NO: 217)
R¹-Phe(DMC)-(D)Ala-G-bhF-NMeAla-R² (XVIIIe);

(SEQ ID NO: 331)
R¹-Phe(DMC)-(D)Asp-G-bhF-NMeAla-R² (XVIIIf);

(SEQ ID NO: 332)
R¹-Phe(DMC)-(D)Thr-G-bhF-NMeAla-R² (XVIIIg);

(SEQ ID NO: 333)
R¹-Phe(DMC)-(D)Glu-G-bhF-NMeAla-R² (XVIIIh);

(SEQ ID NO: 218)
R¹-Phe(DMC)-(D)Ala-G-bhF-NMeIle-R² (XVIIIi);

(SEQ ID NO: 334)
R¹-Phe(DMC)-(D)Asp-G-bhF-NMeIle-R² (XVIIIj);

(SEQ ID NO: 335)
R¹-Phe(DMC)-(D)Thr-G-bhF-NMeIle-R² (XVIIIk);
or
                             (SEQ ID NO: 336)
R¹-Phe(DMC)-(D)Glu-G-bhF-NMeIle-R² (XVIIIl);
``` wherein $R^1$ is H or acetyl; and $R^2$ is OH or $NH_2$.

9. The method of claim 2, wherein $R^1$ is H.

10. The method of claim 1, wherein the peptide is:

```
                             (SEQ ID NO: 43)
H-DMT-a-G-bhF-Sar-NH₂;

(SEQ ID NO: 43)
H-DMT-a-G-bhF-Sar-OH;

(SEQ ID NO: 82)
H-DMT-((D)Thr)-Gly-(β-homoPhe)-Sar-NH₂;

(SEQ ID NO: 82)
H-DMT-((D)Thr)-Gly-(β-homoPhe)-Sar-OH;

(SEQ ID NO: 99)
H-Phe(2,6-dimethyl-4-CONH₂)-a-G-bhF-N(Me)Phg-OH;

(SEQ ID NO: 99)
H-Phe(2,6-dimethyl-4-CONH₂)-a-G-bhF-N(Me)Phg-NH₂;

(SEQ ID NO: 101)
H-Phe(2,6-dimethyl-4-CONH₂)-(D)Ala-Gly-
(b-homoPhe)-N(Me)Nle-NH₂;

(SEQ ID NO: 101)
H-Phe(2,6-dimethyl-4-CONH₂)-(D)Ala-Gly-
(b-homoPhe)-N(Me)Nle-OH;

(SEQ ID NO: 175)
H-DMT-(D)Asp-Gly-(b-homoPhe)-N(Me)Cha-OH;

(SEQ ID NO: 175)
H-DMT-(D)Asp-Gly-(b-homoPhe)-N(Me)Cha-NH₂;

(SEQ ID NO: 111)
H-DMT-a-G-bhF-N(Me)Ala-OH;

(SEQ ID NO: 183)
H-DMT-(D)Thr-G-bhF-N(Me)Ala-OH;

(SEQ ID NO: 83)
H-DMT-(D)Asp-G-bhF-Sar-OH;

(SEQ ID NO: 83)
H-DMT-(D)Asp-G-bhF-Sar-NH₂;

(SEQ ID NO: 70)
H-Phe(2,6-dimethyl-4-CONH₂)-a-G-bhF-Sar-OH;

(SEQ ID NO: 70)
H-Phe(2,6-dimethyl-4-CONH₂)-a-G-bhF-Sar-NH₂;

(SEQ ID NO: 166)
H-Phe(2,6-dimethyl-4-CONH₂)-a-G-bhF(4-F)-N(Me)Nle-
OH;
or
                             (SEQ ID NO: 166)
H-Phe(2,6-dimethyl-4-CONH₂)-a-G-bhF(4-F)-N(Me)Nle-
NH₂.
```

11. The method of claim 1, wherein the peptide is:

```
                             (SEQ ID NO: 43)
    H-DMT-a-G-bhF-Sar-NH₂;
    or
                             (SEQ ID NO: 43)
    H-DMT-a-G-bhF-Sar-OH.
```

12. The method of claim 1, wherein the peptide is:

```
                             (SEQ ID NO: 111)
    H-DMT-a-G-bhF-N(Me)Ala-OH;
    or
                             (SEQ ID NO: 183)
    H-DMT-(D)Thr-G-bhF-N(Me)Ala-OH.
```

13. The method of claim 1, wherein the peptide is:

```
                             (SEQ ID NO: 83)
    H-DMT-(D)Asp-G-bhF-Sar-OH;
    or
                             (SEQ ID NO: 83)
    H-DMT-(D)Asp-G-bhF-Sar-NH2.
```

14. The method of claim 1, wherein the peptide is:

H-Phe(2,6-dimethyl-4-CONH$_2$)-a-G-bhF-Sar-OH; (SEQ ID NO: 70)
or
H-Phe(2,6-dimethyl-4-CONH$_2$)-a-G-bhF-Sar-NH$_2$. (SEQ ID NO: 70)

15. The method of claim 1, wherein the peptide is:

H-Phe(2,6-dimethyl-4-CONH$_2$)-a-G-bhF(4-F)-N(Me)Nle-OH; (SEQ ID NO: 166)
or
H-Phe(2,6-dimethyl-4-CONH$_2$)-a-G-bhF(4-F)-N(Me)Nle-NH$_2$. (SEQ ID NO: 166)

16. The method of claim 1, wherein the peptide is H-DMT-a-G-bhF-Sar-NH$_2$(SEQ ID NO:43).

17. The method of claim 1, wherein the peptide is H-DMT-(D)Thr-G-bhF-N(Me)Ala-OH (SEQ ID NO:183).

18. The method of claim 1, wherein the peptide is H-Phe(2,6-dimethyl-4-CONH$_2$)-a-G-bhF-Sar-NH$_2$(SEQ ID NO:70).

\* \* \* \* \*

SEQUENCE LISTING

```
<160> NUMBER OF SEQ ID NOS: 357

<210> SEQ ID NO 1
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (3)..(3)
<223> OTHER INFORMATION: D-form phenylalanine

<400> SEQUENCE: 1

Xaa Arg Phe Lys
1

<210> SEQ ID NO 2
<211> LENGTH: 4
<212> TYPE: PRT
<213> ORGANISM: Artificial Sequence
```

```
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: D-form lysine

<400> SEQUENCE: 2

Xaa Arg Phe Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: L-4,4'-Biphenylalanine

<400> SEQUENCE: 3

Xaa Arg Xaa Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine

<400> SEQUENCE: 4

Xaa Arg His Lys
1

<210> SEQ ID NO 5
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
```

```
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-Methyl-Lysine

<400> SEQUENCE: 5

Xaa Arg Phe Xaa
1

<210> SEQ ID NO 6

<400> SEQUENCE: 6

000

<210> SEQ ID NO 7
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine

<400> SEQUENCE: 7

Xaa Arg Phe Lys
1

<210> SEQ ID NO 8
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: D-form N-Methyl-L-Alanine
<220> FEATURE:
<221> NAME/KEY: MOD_RES
<222> LOCATION: (3)..(3)
<223> OTHER INFORMATION: alpha-aminoisobutyric acid
<220> FEATURE:
<221> NAME/KEY: MOD_RES
<222> LOCATION: (3)..(3)
<223> OTHER INFORMATION: alpha-aminobutyric acid

<400> SEQUENCE: 8

Xaa Xaa Xaa Gly
1

<210> SEQ ID NO 9
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
```

```
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: Sarcosine

<400> SEQUENCE: 9

Xaa Arg Phe Xaa
1

<210> SEQ ID NO 10
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: D-form N-Methyl-L-Alanine
<220> FEATURE:
<221> NAME/KEY: MOD_RES
<222> LOCATION: (4)..(4)
<223> OTHER INFORMATION: Sarcosine

<400> SEQUENCE: 10

Xaa Xaa Phe Xaa
1

<210> SEQ ID NO 11
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-Methyl-beta-Alanine

<400> SEQUENCE: 11

Xaa Arg Trp Xaa
1

<210> SEQ ID NO 12
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
```

```
<223> OTHER INFORMATION: D-form arginine
<220> FEATURE:
<221> NAME/KEY: MOD_RES
<222> LOCATION: (3)..(3)
<223> OTHER INFORMATION: homophenylalanine
<220> FEATURE:
<221> NAME/KEY: MOD_RES
<222> LOCATION: (4)..(4)
<223> OTHER INFORMATION: N-Methyl-beta-Alanine

<400> SEQUENCE: 12

Xaa Arg Xaa Xaa
1

<210> SEQ ID NO 13
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: (1-naphthyl)-L-alanine
<220> FEATURE:
<221> NAME/KEY: MOD_RES
<222> LOCATION: (4)..(4)
<223> OTHER INFORMATION: N-Methyl-beta-Alanine

<400> SEQUENCE: 13

Xaa Arg Xaa Xaa
1

<210> SEQ ID NO 14
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: D-form N-Methyl-L-phenylalanine

<400> SEQUENCE: 14

Xaa Arg Phe Xaa
1

<210> SEQ ID NO 15
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
```

```
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: alpha-methyl-L-Phenylalanine

<400> SEQUENCE: 15

Xaa Arg Phe Xaa
1

<210> SEQ ID NO 16
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: 4-Fluoro-L-Phenylalanine

<400> SEQUENCE: 16

Xaa Arg Phe Xaa
1

<210> SEQ ID NO 17
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: 3,4-dimethoxy-L-phenylalanine

<400> SEQUENCE: 17

Xaa Arg Phe Xaa
1

<210> SEQ ID NO 18
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
```

-continued

```
<223> OTHER INFORMATION: D-form arginine
<220> FEATURE:
<221> NAME/KEY: MOD_RES
<222> LOCATION: (4)..(4)
<223> OTHER INFORMATION: homophenylalanine

<400> SEQUENCE: 18

Xaa Arg Phe Xaa
1

<210> SEQ ID NO 19
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 4-Fluoro-L-Phenylalanine
<220> FEATURE:
<221> NAME/KEY: MOD_RES
<222> LOCATION: (4)..(4)
<223> OTHER INFORMATION: Sarcosine

<400> SEQUENCE: 19

Xaa Arg Xaa Xaa
1

<210> SEQ ID NO 20
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 4-cyano-L-phenylalanine
<220> FEATURE:
<221> NAME/KEY: MOD_RES
<222> LOCATION: (4)..(4)
<223> OTHER INFORMATION: Sarcosine

<400> SEQUENCE: 20

Xaa Arg Xaa Xaa
1

<210> SEQ ID NO 21
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
```

```
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: L-1,2,3,4,-tetrahydro-isoquinoline-3-carboxylic
      acid
<220> FEATURE:
<221> NAME/KEY: MOD_RES
<222> LOCATION: (4)..(4)
<223> OTHER INFORMATION: Sarcosine

<400> SEQUENCE: 21

Xaa Arg Xaa Xaa
1

<210> SEQ ID NO 22
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 3,4 dichloro-L-phenylalanine
<220> FEATURE:
<221> NAME/KEY: MOD_RES
<222> LOCATION: (4)..(4)
<223> OTHER INFORMATION: Sarcosine

<400> SEQUENCE: 22

Xaa Arg Xaa Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: L-4,4'-Biphenylalanine
<220> FEATURE:
<221> NAME/KEY: MOD_RES
<222> LOCATION: (4)..(4)
<223> OTHER INFORMATION: Sarcosine

<400> SEQUENCE: 23

Xaa Arg Xaa Xaa
1
```

```
<210> SEQ ID NO 24
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 4-tert-butyl-L-phenylalanine
<220> FEATURE:
<221> NAME/KEY: MOD_RES
<222> LOCATION: (4)..(4)
<223> OTHER INFORMATION: Sarcosine

<400> SEQUENCE: 24

Xaa Arg Xaa Xaa
1

<210> SEQ ID NO 25
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 3,4-dimethoxy-L-phenylalanine
<220> FEATURE:
<221> NAME/KEY: MOD_RES
<222> LOCATION: (4)..(4)
<223> OTHER INFORMATION: Sarcosine

<400> SEQUENCE: 25

Xaa Arg Xaa Xaa
1

<210> SEQ ID NO 26
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 3,3,-diphenyl-L-alanine
<220> FEATURE:
<221> NAME/KEY: MOD_RES
<222> LOCATION: (4)..(4)
```

```
<223> OTHER INFORMATION: Sarcosine

<400> SEQUENCE: 26

Xaa Arg Xaa Xaa
1

<210> SEQ ID NO 27
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-Octylglycine

<400> SEQUENCE: 27

Xaa Arg Phe Xaa
1

<210> SEQ ID NO 28
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: norleucine

<400> SEQUENCE: 28

Xaa Arg Phe Xaa
1

<210> SEQ ID NO 29
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine

<400> SEQUENCE: 29

Xaa Arg Phe Leu
1
```

```
<210> SEQ ID NO 30
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine

<400> SEQUENCE: 30

Xaa Arg Phe Val
1

<210> SEQ ID NO 31
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: norleucine

<400> SEQUENCE: 31

Xaa Arg Trp Xaa
1

<210> SEQ ID NO 32
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 3,3,-diphenyl-L-alanine
<220> FEATURE:
<221> NAME/KEY: MOD_RES
<222> LOCATION: (4)..(4)
<223> OTHER INFORMATION: Sarcosine

<400> SEQUENCE: 32

Xaa Arg Xaa Xaa
1

<210> SEQ ID NO 33
<211> LENGTH: 4
<212> TYPE: PRT
<213> ORGANISM: Artificial Sequence
```

```
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: 3,3,-diphenyl-L-alanine

<400> SEQUENCE: 33

Xaa Arg Gly Xaa
1

<210> SEQ ID NO 34
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine

<400> SEQUENCE: 34

Xaa Arg Gly Trp
1

<210> SEQ ID NO 35
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: Sarcosine

<400> SEQUENCE: 35

Xaa Arg Xaa Trp
1

<210> SEQ ID NO 36
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
```

```
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: 3,3,-diphenyl-L-alanine

<400> SEQUENCE: 36

Xaa Arg Phe Xaa
1

<210> SEQ ID NO 37
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (5)..(5)
<223> OTHER INFORMATION: norleucine

<400> SEQUENCE: 37

Xaa Ala Gly Phe Xaa
1               5

<210> SEQ ID NO 38
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: 4-Fluoro-L-Phenylalanine

<400> SEQUENCE: 38

Xaa Ala Gly Xaa Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
```

```
<222> LOCATION: (4)..(4)
<223> OTHER INFORMATION: 4-cyano-L-phenylalanine

<400> SEQUENCE: 39

Xaa Ala Gly Xaa Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-1,2,3,4,-tetrahydro-isoquinoline-3-carboxylic
      acid

<400> SEQUENCE: 40

Xaa Ala Gly Xaa Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: 3,4 dichloro-L-phenylalanine

<400> SEQUENCE: 41

Xaa Ala Gly Xaa Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (5)..(5)
<223> OTHER INFORMATION: Sarcosine
```

<400> SEQUENCE: 42

Xaa Ala Gly Phe Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 43

Xaa Ala Gly Xaa Xaa
1               5

<210> SEQ ID NO 44
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: D form 1,2,3,4,-tetrahydro-isoquinoline-3-
      carboxylic acid
<220> FEATURE:
<221> NAME/KEY: MOD_RES
<222> LOCATION: (4)..(4)
<223> OTHER INFORMATION: Sarcosine

<400> SEQUENCE: 44

Xaa Xaa Phe Xaa
1

<210> SEQ ID NO 45
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: D form 1,2,3,4,-tetrahydro-isoquinoline-3-
      carboxylic acid
<220> FEATURE:
<221> NAME/KEY: MOD_RES
<222> LOCATION: (5)..(5)

```
<223> OTHER INFORMATION: Sarcosine

<400> SEQUENCE: 45

Xaa Xaa Gly Phe Xaa
1               5

<210> SEQ ID NO 46
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: homophenylalanine
<220> FEATURE:
<221> NAME/KEY: MOD_RES
<222> LOCATION: (4)..(4)
<223> OTHER INFORMATION: Sarcosine

<400> SEQUENCE: 46

Xaa Ala Xaa Xaa
1

<210> SEQ ID NO 47
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: homophenylalanine
<220> FEATURE:
<221> NAME/KEY: MOD_RES
<222> LOCATION: (5)..(5)
<223> OTHER INFORMATION: Sarcosine

<400> SEQUENCE: 47

Xaa Ala Gly Xaa Xaa
1               5

<210> SEQ ID NO 48
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
```

```
<223> OTHER INFORMATION: D-form alanine
<220> FEATURE:
<221> NAME/KEY: MOD_RES
<222> LOCATION: (3)..(3)
<223> OTHER INFORMATION: homophenylalanine
<220> FEATURE:
<221> NAME/KEY: MOD_RES
<222> LOCATION: (4)..(4)
<223> OTHER INFORMATION: norleucine

<400> SEQUENCE: 48

Xaa Ala Xaa Xaa
1

<210> SEQ ID NO 49
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: homophenylalanine
<220> FEATURE:
<221> NAME/KEY: MOD_RES
<222> LOCATION: (5)..(5)
<223> OTHER INFORMATION: norleucine

<400> SEQUENCE: 49

Xaa Ala Gly Xaa Xaa
1               5

<210> SEQ ID NO 50
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: beta homo-L-Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 50

Xaa Ala Gly Xaa Xaa
1               5

<210> SEQ ID NO 51
<211> LENGTH: 5
<212> TYPE: PRT
<213> ORGANISM: Artificial Sequence
<220> FEATURE:
```

```
<223> OTHER INFORMATION: Synthesized opioid agonist peptide
<220> FEATURE:
<221> NAME/KEY: MOD_RES
<222> LOCATION: (1)..(1)
<223> OTHER INFORMATION: N-Methyl-L-Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 51

Xaa Ala Gly Xaa Xaa
1               5

<210> SEQ ID NO 52
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 3-t-butyl-L-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 52

Xaa Ala Gly Xaa Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (1)..(1)
<223> OTHER INFORMATION: D-form tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 53

Tyr Ala Gly Xaa Xaa
```

```
1               5

<210> SEQ ID NO 54
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: homo-L-Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 54

Xaa Ala Gly Xaa Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 3-chloro-L-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 55

Xaa Ala Gly Xaa Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: meta-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
```

```
<220> FEATURE:
<221> NAME/KEY: MOD_RES
<222> LOCATION: (5)..(5)
<223> OTHER INFORMATION: Sarcosine

<400> SEQUENCE: 56

Xaa Ala Gly Xaa Xaa
1               5

<210> SEQ ID NO 57
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 3-Fluoro-L-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 57

Xaa Ala Gly Xaa Xaa
1               5

<210> SEQ ID NO 58
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Tyr(3-OH)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 58

Xaa Ala Gly Xaa Xaa
1               5

<210> SEQ ID NO 59
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(4-NHCOCH3)
```

```
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 59

Xaa Ala Gly Xaa Xaa
1               5

<210> SEQ ID NO 60
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 4-Carbamoyl-L-phenylalanine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 60

Xaa Ala Gly Xaa Xaa
1               5

<210> SEQ ID NO 61
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 7-Hydroxy-1,2,3,4-tetrahydroisoquinoline-3-
      carboxylic acid
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 61

Xaa Ala Gly Xaa Xaa
1               5

<210> SEQ ID NO 62
```

```
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 62

Tyr Ala Gly Xaa Xaa
1               5

<210> SEQ ID NO 63
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 5-hydroxy-L-tryptophan
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 63

Xaa Ala Gly Xaa Xaa
1               5

<210> SEQ ID NO 64
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: Sarcosine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine
```

<400> SEQUENCE: 64

Xaa Ala Xaa Xaa Xaa
1               5

<210> SEQ ID NO 65
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: THP
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 65

Xaa Ala Xaa Xaa Xaa
1               5

<210> SEQ ID NO 66
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 66

Xaa Ala Ala Xaa Xaa
1               5

<210> SEQ ID NO 67
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine

```
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 67

Xaa Ala Leu Xaa Xaa
 1               5

<210> SEQ ID NO 68
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 68

Xaa Ala Ile Xaa Xaa
 1               5

<210> SEQ ID NO 69
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 69

Xaa Ala Val Xaa Xaa
 1               5

<210> SEQ ID NO 70
<211> LENGTH: 5
```

```
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 70

Xaa Ala Gly Xaa Xaa
1               5

<210> SEQ ID NO 71
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 4-(2-aminoethoxy)-L-phenylalanine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 71

Xaa Ala Gly Xaa Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: alpha-aminoisobutyric acid
<220> FEATURE:
<221> NAME/KEY: MOD_RES
<222> LOCATION: (4)..(4)
<223> OTHER INFORMATION: L-beta-homophenylalanine
<220> FEATURE:
```

```
<221> NAME/KEY: MOD_RES
<222> LOCATION: (5)..(5)
<223> OTHER INFORMATION: Sarcosine

<400> SEQUENCE: 72

Xaa Ala Xaa Xaa Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: beta-alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 73

Xaa Ala Xaa Xaa Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 74

Xaa Gly Gly Xaa Xaa
1               5

<210> SEQ ID NO 75
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
```

```
<221> NAME/KEY: MOD_RES
<222> LOCATION: (2)..(2)
<223> OTHER INFORMATION: alpha-aminoisobutyric acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 75

Xaa Xaa Gly Xaa Xaa
1               5

<210> SEQ ID NO 76
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 76

Xaa Thr Gly Xaa Xaa
1               5

<210> SEQ ID NO 77
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 77

Xaa Asp Gly Xaa Xaa
1               5

<210> SEQ ID NO 78
<211> LENGTH: 5
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MOD_RES
<222> LOCATION: (2)..(2)
<223> OTHER INFORMATION: N-Methyl-L-Arginine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 78

Xaa Xaa Gly Xaa Xaa
1               5

<210> SEQ ID NO 79
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 79

Xaa Ala Gly Xaa Xaa
1               5

<210> SEQ ID NO 80
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 80

Xaa Ala Gly Xaa Xaa
1               5
```

```
<210> SEQ ID NO 81
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 81

Xaa Gly Gly Xaa Xaa
1               5

<210> SEQ ID NO 82
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 82

Xaa Thr Gly Xaa Xaa
1               5

<210> SEQ ID NO 83
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 83
```

```
Xaa Asp Gly Xaa Xaa
1               5

<210> SEQ ID NO 84
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form tyrosine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 84

Xaa Tyr Gly Xaa Xaa
1               5

<210> SEQ ID NO 85
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form tyrosine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 85

Xaa Asp Gly Xaa Xaa
1               5

<210> SEQ ID NO 86
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
```

```
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 86

Xaa Ala Gly Xaa Xaa
1               5

<210> SEQ ID NO 87
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 87

Xaa Ala Gly Xaa Xaa
1               5

<210> SEQ ID NO 88
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 88

Xaa Ala Gly Xaa Xaa
1               5

<210> SEQ ID NO 89
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 4-Carboxy-L-Phenylalanine
<220> FEATURE:
<221> NAME/KEY: MISC_FEATURE
```

```
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 89

Xaa Ala Gly Xaa Xaa
1               5

<210> SEQ ID NO 90
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: alpha-aminoisobutyric acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 90

Xaa Xaa Gly Xaa Xaa
1               5

<210> SEQ ID NO 91
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: N-Methyl-L-Arginine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 91

Xaa Xaa Gly Xaa Xaa
1               5

<210> SEQ ID NO 92
<211> LENGTH: 5
<212> TYPE: PRT
<213> ORGANISM: Artificial Sequence
```

```
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-L-Leucine

<400> SEQUENCE: 92

Xaa Ala Gly Xaa Xaa
1               5

<210> SEQ ID NO 93
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-L-Alanine

<400> SEQUENCE: 93

Xaa Ala Gly Xaa Xaa
1               5

<210> SEQ ID NO 94
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine

<400> SEQUENCE: 94

Xaa Ala Gly Xaa Gly
1               5
```

```
<210> SEQ ID NO 95
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-L-Isoleucine

<400> SEQUENCE: 95

Xaa Ala Gly Xaa Xaa
1               5

<210> SEQ ID NO 96
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-L-Valine

<400> SEQUENCE: 96

Xaa Ala Gly Xaa Xaa
1               5

<210> SEQ ID NO 97
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
```

-continued

<223> OTHER INFORMATION: N-methyl-Norvaline

<400> SEQUENCE: 97

Xaa Ala Gly Xaa Xaa
1               5

<210> SEQ ID NO 98
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-cyclohxyl-alanine

<400> SEQUENCE: 98

Xaa Ala Gly Xaa Xaa
1               5

<210> SEQ ID NO 99
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Phenylglycine

<400> SEQUENCE: 99

Xaa Ala Gly Xaa Xaa
1               5

<210> SEQ ID NO 100
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)

```
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Phenylalanine

<400> SEQUENCE: 100

Xaa Ala Gly Xaa Xaa
1               5

<210> SEQ ID NO 101
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Norleucine

<400> SEQUENCE: 101

Xaa Ala Gly Xaa Xaa
1               5

<210> SEQ ID NO 102
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-tyrosine

<400> SEQUENCE: 102

Xaa Ala Gly Xaa Xaa
1               5

<210> SEQ ID NO 103
<211> LENGTH: 5
<212> TYPE: PRT
<213> ORGANISM: Artificial Sequence
<220> FEATURE:
```

```
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 103

Xaa Xaa Gly Xaa Xaa
1               5

<210> SEQ ID NO 104
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 104

Xaa Xaa Gly Xaa Xaa
1               5

<210> SEQ ID NO 105
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 4-Tetrazole-Phenylalanine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 105
```

```
Xaa Ala Gly Xaa Xaa
1               5

<210> SEQ ID NO 106
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-tryptophan

<400> SEQUENCE: 106

Xaa Ala Gly Xaa Xaa
1               5

<210> SEQ ID NO 107
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (5)..(5)
<223> OTHER INFORMATION: Sarcosine

<400> SEQUENCE: 107

Xaa Ala Gly Xaa Xaa
1               5

<210> SEQ ID NO 108
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
```

```
<221> NAME/KEY: MOD_RES
<222> LOCATION: (4)..(4)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (5)..(5)
<223> OTHER INFORMATION: Sarcosine

<400> SEQUENCE: 108

Xaa Ala Gly Xaa Xaa
1               5

<210> SEQ ID NO 109
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: Sarcosine

<400> SEQUENCE: 109

Xaa Ala Gly Xaa Xaa
1               5

<210> SEQ ID NO 110
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: Sarcosine

<400> SEQUENCE: 110

Xaa Ala Gly Xaa Xaa
1               5

<210> SEQ ID NO 111
<211> LENGTH: 5
<212> TYPE: PRT
<213> ORGANISM: Artificial Sequence
<220> FEATURE:
<223> OTHER INFORMATION: Synthesized opioid agonist peptide
```

<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-L-Alanine

<400> SEQUENCE: 111

Xaa Ala Gly Xaa Xaa
1               5

<210> SEQ ID NO 112
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine

<400> SEQUENCE: 112

Xaa Ala Gly Xaa Gly
1               5

<210> SEQ ID NO 113
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-Isoleucine

<400> SEQUENCE: 113

Xaa Ala Gly Xaa Xaa
1               5

<210> SEQ ID NO 114
<211> LENGTH: 5

```
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: 2-Nathyl Alanine

<400> SEQUENCE: 114

Xaa Ala Gly Xaa Xaa
1               5

<210> SEQ ID NO 115
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(Octyl)Glycine

<400> SEQUENCE: 115

Xaa Ala Gly Xaa Xaa
1               5

<210> SEQ ID NO 116
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(iospentyl)Glycine
```

```
<400> SEQUENCE: 116

Xaa Ala Gly Xaa Xaa
1               5

<210> SEQ ID NO 117
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(3-isopropyloxypropyl)Glycine

<400> SEQUENCE: 117

Xaa Ala Gly Xaa Xaa
1               5

<210> SEQ ID NO 118
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(benzyl)Glycine

<400> SEQUENCE: 118

Xaa Ala Gly Xaa Xaa
1               5

<210> SEQ ID NO 119
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
```

```
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(cyclohexylmethyl)Glycine

<400> SEQUENCE: 119

Xaa Ala Gly Xaa Xaa
1               5

<210> SEQ ID NO 120
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(3-propanoic acid)Glycine

<400> SEQUENCE: 120

Xaa Ala Gly Xaa Xaa
1               5

<210> SEQ ID NO 121
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(phenethyl)Glycine

<400> SEQUENCE: 121

Xaa Ala Gly Xaa Xaa
1               5

<210> SEQ ID NO 122
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
```

```
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(trifluoroethyl)Glycine

<400> SEQUENCE: 122

Xaa Ala Gly Xaa Xaa
1               5

<210> SEQ ID NO 123
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(cyclohexyl)Glycine

<400> SEQUENCE: 123

Xaa Ala Gly Xaa Xaa
1               5

<210> SEQ ID NO 124
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(amyl)Glycine

<400> SEQUENCE: 124

Xaa Ala Gly Xaa Xaa
1               5
```

```
<210> SEQ ID NO 125
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N(hexadecyl)Glycine

<400> SEQUENCE: 125

Xaa Ala Gly Xaa Xaa
1               5

<210> SEQ ID NO 126
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 126

Xaa Ala Gly Xaa Xaa
1               5

<210> SEQ ID NO 127
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
```

-continued

```
<222> LOCATION: (5)..(5)
<223> OTHER INFORMATION: N-methyl-L-Leucine

<400> SEQUENCE: 127

Xaa Ala Gly Xaa Xaa
1               5

<210> SEQ ID NO 128
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 128

Xaa Ala Gly Xaa Xaa
1               5

<210> SEQ ID NO 129
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 129

Xaa Ala Gly Xaa Xaa
1               5

<210> SEQ ID NO 130
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
```

```
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 130

Xaa Ala Gly Xaa Xaa
1               5

<210> SEQ ID NO 131
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 131

Xaa Ala Gly Xaa Xaa
1               5

<210> SEQ ID NO 132
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 132

Xaa Ala Gly Xaa Xaa
1               5

<210> SEQ ID NO 133
<211> LENGTH: 5
<212> TYPE: PRT
<213> ORGANISM: Artificial Sequence
```

```
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 133

Xaa Ala Gly Xaa Xaa
1               5

<210> SEQ ID NO 134
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 134

Xaa Ala Gly Xaa Xaa
1               5

<210> SEQ ID NO 135
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 135
```

```
Xaa Ala Gly Xaa Xaa
1               5

<210> SEQ ID NO 136
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 136

Xaa Ala Gly Xaa Xaa
1               5

<210> SEQ ID NO 137
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 137

Xaa Ala Gly Xaa Xaa
1               5

<210> SEQ ID NO 138
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
```

```
<223> OTHER INFORMATION: L-beta-homotryrosine
<220> FEATURE:
<221> NAME/KEY: MOD_RES
<222> LOCATION: (5)..(5)
<223> OTHER INFORMATION: N-methyl-L-Leucine

<400> SEQUENCE: 138

Xaa Ala Gly Xaa Xaa
1               5

<210> SEQ ID NO 139
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-methyl-L-Leucine

<400> SEQUENCE: 139

Xaa Ala Gly Xaa Xaa
1               5

<210> SEQ ID NO 140
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 140

Xaa Ala Gly Xaa Xaa
1               5

<210> SEQ ID NO 141
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
```

```
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 141

Xaa Ala Gly Xaa Xaa
1               5

<210> SEQ ID NO 142
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 142

Xaa Ala Gly Xaa Xaa
1               5

<210> SEQ ID NO 143
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 143

Xaa Ala Gly Xaa Xaa
1               5

<210> SEQ ID NO 144
```

```
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 144

Xaa Ala Gly Xaa Xaa
1               5

<210> SEQ ID NO 145
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 145

Xaa Ala Gly Xaa Xaa
1               5

<210> SEQ ID NO 146
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-methyl-L-Leucine
```

<400> SEQUENCE: 146

Xaa Ala Gly Xaa Xaa
1               5

<210> SEQ ID NO 147
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 147

Xaa Ala Gly Xaa Xaa
1               5

<210> SEQ ID NO 148
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 148

Xaa Ala Gly Xaa Xaa
1               5

<210> SEQ ID NO 149
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine

```
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 149

Xaa Ala Gly Xaa Xaa
1               5

<210> SEQ ID NO 150
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 150

Xaa Ala Gly Xaa Xaa
1               5

<210> SEQ ID NO 151
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-methyl-L-Leucine

<400> SEQUENCE: 151

Xaa Ala Gly Xaa Xaa
1               5

<210> SEQ ID NO 152
<211> LENGTH: 5
<212> TYPE: PRT
<213> ORGANISM: Artificial Sequence
<220> FEATURE:
<223> OTHER INFORMATION: Synthesized opioid agonist peptide
```

```
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homotryrosine
<220> FEATURE:
<221> NAME/KEY: MOD_RES
<222> LOCATION: (5)..(5)
<223> OTHER INFORMATION: N-methyl-L-Leucine

<400> SEQUENCE: 152

Xaa Ala Gly Xaa Xaa
1               5

<210> SEQ ID NO 153
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-methyl-L-Leucine

<400> SEQUENCE: 153

Xaa Ala Gly Xaa Xaa
1               5

<210> SEQ ID NO 154
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: D-form N-Methyl-Phenylalanine
<220> FEATURE:
<221> NAME/KEY: MOD_RES
<222> LOCATION: (5)..(5)
<223> OTHER INFORMATION: N-methyl-L-Norleucine

<400> SEQUENCE: 154

Xaa Ala Gly Xaa Xaa
1               5
```

```
<210> SEQ ID NO 155
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Leucine

<400> SEQUENCE: 155

Xaa Ala Gly Xaa Xaa
1               5

<210> SEQ ID NO 156
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-cyclohxyl-alanine

<400> SEQUENCE: 156

Xaa Ala Gly Xaa Xaa
1               5

<210> SEQ ID NO 157
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
```

```
<221> NAME/KEY: MOD_RES
<222> LOCATION: (5)..(5)
<223> OTHER INFORMATION: N-methyl-Phenylglycine

<400> SEQUENCE: 157

Xaa Ala Gly Xaa Xaa
 1               5

<210> SEQ ID NO 158
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Phenylalanine

<400> SEQUENCE: 158

Xaa Ala Gly Xaa Xaa
 1               5

<210> SEQ ID NO 159
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Norleucine

<400> SEQUENCE: 159

Xaa Ala Gly Xaa Xaa
 1               5

<210> SEQ ID NO 160
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
```

```
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-tyrosine

<400> SEQUENCE: 160

Xaa Ala Gly Xaa Xaa
1               5

<210> SEQ ID NO 161
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Valine

<400> SEQUENCE: 161

Xaa Ala Gly Xaa Xaa
1               5

<210> SEQ ID NO 162
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-Norvaline

<400> SEQUENCE: 162

Xaa Ala Gly Xaa Xaa
1               5

<210> SEQ ID NO 163
<211> LENGTH: 5
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 163

Xaa Ala Gly Xaa Xaa
1               5

<210> SEQ ID NO 164
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 164

Xaa Ala Gly Xaa Xaa
1               5

<210> SEQ ID NO 165
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 165
```

Xaa Ala Gly Xaa Xaa
1               5

<210> SEQ ID NO 166
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 166

Xaa Ala Gly Xaa Xaa
1               5

<210> SEQ ID NO 167
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 167

Xaa Ala Gly Xaa Xaa
1               5

<210> SEQ ID NO 168
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES

```
<222> LOCATION: (4)..(4)
<223> OTHER INFORMATION: beta-homotryrosine
<220> FEATURE:
<221> NAME/KEY: MOD_RES
<222> LOCATION: (5)..(5)
<223> OTHER INFORMATION: N-methyl-Norleucine

<400> SEQUENCE: 168

Xaa Ala Gly Xaa Xaa
1               5

<210> SEQ ID NO 169
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Leucine

<400> SEQUENCE: 169

Xaa Asp Gly Xaa Xaa
1               5

<210> SEQ ID NO 170
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Alanine

<400> SEQUENCE: 170

Xaa Asp Gly Xaa Xaa
1               5

<210> SEQ ID NO 171
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
```

```
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Tryptophan

<400> SEQUENCE: 171

Xaa Asp Gly Xaa Xaa
1               5

<210> SEQ ID NO 172
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Isoleucine

<400> SEQUENCE: 172

Xaa Asp Gly Xaa Xaa
1               5

<210> SEQ ID NO 173
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Valine

<400> SEQUENCE: 173

Xaa Asp Gly Xaa Xaa
1               5
```

```
<210> SEQ ID NO 174
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Norvaline

<400> SEQUENCE: 174

Xaa Asp Gly Xaa Xaa
1               5

<210> SEQ ID NO 175
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-cyclohexyl alanine

<400> SEQUENCE: 175

Xaa Asp Gly Xaa Xaa
1               5

<210> SEQ ID NO 176
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
```

```
<223> OTHER INFORMATION: N-methyl-L-Phenylglycine

<400> SEQUENCE: 176

Xaa Asp Gly Xaa Xaa
1               5

<210> SEQ ID NO 177
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Phenylalanine

<400> SEQUENCE: 177

Xaa Asp Gly Xaa Xaa
1               5

<210> SEQ ID NO 178
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Norleucine

<400> SEQUENCE: 178

Xaa Asp Gly Xaa Xaa
1               5

<210> SEQ ID NO 179
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
```

```
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine

<400> SEQUENCE: 179

Xaa Asp Gly Xaa Gly
1               5

<210> SEQ ID NO 180
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Tyrosine

<400> SEQUENCE: 180

Xaa Asp Gly Xaa Xaa
1               5

<210> SEQ ID NO 181
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 181

Xaa Ala Gly Xaa Xaa
1               5

<210> SEQ ID NO 182
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
```

<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Isoleucine

<400> SEQUENCE: 182

Xaa Thr Gly Xaa Xaa
1               5

<210> SEQ ID NO 183
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Alanine

<400> SEQUENCE: 183

Xaa Thr Gly Xaa Xaa
1               5

<210> SEQ ID NO 184
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-Norvaline

<400> SEQUENCE: 184

Xaa Ala Gly Xaa Xaa
1               5

<210> SEQ ID NO 185

<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Glutamin Acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Alanine

<400> SEQUENCE: 185

Xaa Glu Gly Xaa Xaa
1               5

<210> SEQ ID NO 186
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Glutamin Acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: N-methyl-L-Isoleucine

<400> SEQUENCE: 186

Xaa Glu Gly Xaa Xaa
1               5

<210> SEQ ID NO 187
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Glutamin Acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Sarcosine

<400> SEQUENCE: 187

Xaa Glu Gly Xaa Xaa
1               5

<210> SEQ ID NO 188
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 188

Xaa Ala Gly Xaa Xaa
1               5

<210> SEQ ID NO 189
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 189

Xaa Ala Gly Xaa Xaa
1               5

<210> SEQ ID NO 190
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 190

Xaa Ala Gly Xaa Xaa
1               5

<210> SEQ ID NO 191
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 191

Xaa Ala Gly Xaa Xaa
1               5

<210> SEQ ID NO 192
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 192

Xaa Ala Gly Xaa Xaa
1               5

<210> SEQ ID NO 193
<211> LENGTH: 5
<212> TYPE: PRT
<213> ORGANISM: Artificial Sequence
<220> FEATURE:
<223> OTHER INFORMATION: Synthesized opioid agonist peptide

```
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 193

Xaa Ala Gly Xaa Xaa
1               5

<210> SEQ ID NO 194
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 194

Xaa Ala Gly Xaa Xaa
1               5

<210> SEQ ID NO 195
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 195

Xaa Ala Gly Xaa Xaa
1               5
```

```
<210> SEQ ID NO 196
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 196

Xaa Ala Gly Xaa Xaa
1               5

<210> SEQ ID NO 197
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 197

Xaa Ala Gly Xaa Xaa
1               5

<210> SEQ ID NO 198
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
```

```
<221> NAME/KEY: MOD_RES
<222> LOCATION: (5)..(5)
<223> OTHER INFORMATION: N-Methyl-L-Leucine

<400> SEQUENCE: 198

Xaa Ala Gly Xaa Xaa
1               5

<210> SEQ ID NO 199
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 199

Xaa Ala Gly Xaa Xaa
1               5

<210> SEQ ID NO 200
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryrosine
<220> FEATURE:
<221> NAME/KEY: MOD_RES
<222> LOCATION: (5)..(5)
<223> OTHER INFORMATION: N-Methyl-L-Leucine

<400> SEQUENCE: 200

Xaa Ala Gly Xaa Xaa
1               5

<210> SEQ ID NO 201
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
```

```
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-Methyl-L-Leucine

<400> SEQUENCE: 201

Xaa Ala Gly Xaa Xaa
1               5

<210> SEQ ID NO 202
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 202

Xaa Ala Gly Xaa Xaa
1               5

<210> SEQ ID NO 203
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 203

Xaa Ala Gly Xaa Xaa
1               5

<210> SEQ ID NO 204
<211> LENGTH: 5
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 204

Xaa Ala Gly Xaa Xaa
1               5

<210> SEQ ID NO 205
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 205

Xaa Ala Gly Xaa Xaa
1               5

<210> SEQ ID NO 206
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 206
```

```
Xaa Ala Gly Xaa Xaa
1               5

<210> SEQ ID NO 207
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 207

Xaa Ala Gly Xaa Xaa
1               5

<210> SEQ ID NO 208
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 208

Xaa Ala Gly Xaa Xaa
1               5

<210> SEQ ID NO 209
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
```

```
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 209

Xaa Ala Gly Xaa Xaa
1               5

<210> SEQ ID NO 210
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 210

Xaa Ala Gly Xaa Xaa
1               5

<210> SEQ ID NO 211
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 211

Xaa Ala Gly Xaa Xaa
1               5

<210> SEQ ID NO 212
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
```

```
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 212

Xaa Ala Gly Xaa Xaa
1               5

<210> SEQ ID NO 213
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 213

Xaa Ala Gly Xaa Xaa
1               5

<210> SEQ ID NO 214
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryrosine
<220> FEATURE:
<221> NAME/KEY: MOD_RES
<222> LOCATION: (5)..(5)
<223> OTHER INFORMATION: N-Methyl-L-Leucine

<400> SEQUENCE: 214

Xaa Ala Gly Xaa Xaa
1               5
```

-continued

```
<210> SEQ ID NO 215
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-Methyl-L-Leucine

<400> SEQUENCE: 215

Xaa Ala Gly Xaa Xaa
1               5

<210> SEQ ID NO 216
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Leucine

<400> SEQUENCE: 216

Xaa Ala Gly Xaa Xaa
1               5

<210> SEQ ID NO 217
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
```

```
<223> OTHER INFORMATION: N-Methyl-L-Alanine

<400> SEQUENCE: 217

Xaa Ala Gly Xaa Xaa
1               5

<210> SEQ ID NO 218
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Isoleucine

<400> SEQUENCE: 218

Xaa Ala Gly Xaa Xaa
1               5

<210> SEQ ID NO 219
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Valine

<400> SEQUENCE: 219

Xaa Ala Gly Xaa Xaa
1               5

<210> SEQ ID NO 220
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
```

```
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Norvaline

<400> SEQUENCE: 220

Xaa Ala Gly Xaa Xaa
1               5

<210> SEQ ID NO 221
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Cyclohexyl-alanine

<400> SEQUENCE: 221

Xaa Ala Gly Xaa Xaa
1               5

<210> SEQ ID NO 222
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Phenylglycine

<400> SEQUENCE: 222

Xaa Ala Gly Xaa Xaa
1               5

<210> SEQ ID NO 223
<211> LENGTH: 5
<212> TYPE: PRT
<213> ORGANISM: Artificial Sequence
<220> FEATURE:
```

```
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Phenylalanine

<400> SEQUENCE: 223

Xaa Ala Gly Xaa Xaa
1               5

<210> SEQ ID NO 224
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Norleucine

<400> SEQUENCE: 224

Xaa Ala Gly Xaa Xaa
1               5

<210> SEQ ID NO 225
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Tyrosine

<400> SEQUENCE: 225

Xaa Ala Gly Xaa Xaa
```

-continued

```
1               5

<210> SEQ ID NO 226
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Tryptophan

<400> SEQUENCE: 226

Xaa Ala Gly Xaa Xaa
1               5

<210> SEQ ID NO 227
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Alanine

<400> SEQUENCE: 227

Xaa Ala Gly Xaa Xaa
1               5

<210> SEQ ID NO 228
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
```

<400> SEQUENCE: 228

Xaa Ala Gly Xaa Gly
1               5

<210> SEQ ID NO 229
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Isoleucine

<400> SEQUENCE: 229

Xaa Ala Gly Xaa Xaa
1               5

<210> SEQ ID NO 230
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: D-form N-Methyl-Phenylalanine
<220> FEATURE:
<221> NAME/KEY: MOD_RES
<222> LOCATION: (5)..(5)
<223> OTHER INFORMATION: N-Methyl-L-Norleucine

<400> SEQUENCE: 230

Xaa Ala Gly Xaa Xaa
1               5

<210> SEQ ID NO 231
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine

```
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Leucine

<400> SEQUENCE: 231

Xaa Ala Gly Xaa Xaa
1               5

<210> SEQ ID NO 232
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Cyclohexyl-alanine

<400> SEQUENCE: 232

Xaa Ala Gly Xaa Xaa
1               5

<210> SEQ ID NO 233
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Phenylglycine

<400> SEQUENCE: 233

Xaa Ala Gly Xaa Xaa
1               5

<210> SEQ ID NO 234
<211> LENGTH: 5
<212> TYPE: PRT
<213> ORGANISM: Artificial Sequence
<220> FEATURE:
<223> OTHER INFORMATION: Synthesized opioid agonist peptide
```

```
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Phenylalanine

<400> SEQUENCE: 234

Xaa Ala Gly Xaa Xaa
1               5

<210> SEQ ID NO 235
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Norleucine

<400> SEQUENCE: 235

Xaa Ala Gly Xaa Xaa
1               5

<210> SEQ ID NO 236
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Tyrosine

<400> SEQUENCE: 236

Xaa Ala Gly Xaa Xaa
1               5
```

```
<210> SEQ ID NO 237
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Valine

<400> SEQUENCE: 237

Xaa Ala Gly Xaa Xaa
1               5

<210> SEQ ID NO 238
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-L-Norvaline

<400> SEQUENCE: 238

Xaa Thr Gly Xaa Xaa
1               5

<210> SEQ ID NO 239
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
```

```
<221> NAME/KEY: MOD_RES
<222> LOCATION: (5)..(5)
<223> OTHER INFORMATION: N-Methyl-L-Leucine

<400> SEQUENCE: 239

Xaa Thr Gly Xaa Xaa
1               5

<210> SEQ ID NO 240
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 240

Xaa Thr Gly Xaa Xaa
1               5

<210> SEQ ID NO 241
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 241

Xaa Thr Gly Xaa Xaa
1               5

<210> SEQ ID NO 242
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
```

```
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 242

Xaa Ala Gly Xaa Xaa
1               5

<210> SEQ ID NO 243
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 243

Xaa Ala Gly Xaa Xaa
1               5

<210> SEQ ID NO 244
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 244

Xaa Thr Gly Xaa Xaa
1               5

<210> SEQ ID NO 245
<211> LENGTH: 5
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 245

Xaa Ala Gly Xaa Xaa
1               5

<210> SEQ ID NO 246
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 246

Xaa Ala Gly Xaa Xaa
1               5

<210> SEQ ID NO 247
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 247
```

```
Xaa Ala Gly Xaa Xaa
1               5

<210> SEQ ID NO 248
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 248

Xaa Ala Gly Xaa Xaa
1               5

<210> SEQ ID NO 249
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 249

Xaa Ala Gly Xaa Xaa
1               5

<210> SEQ ID NO 250
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
```

```
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 250

Xaa Thr Gly Xaa Xaa
1               5

<210> SEQ ID NO 251
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Threonine
<220> FEATURE:
<221> NAME/KEY: MOD_RES
<222> LOCATION: (4)..(4)
<223> OTHER INFORMATION: L-beta-homotryrosine
<220> FEATURE:
<221> NAME/KEY: MOD_RES
<222> LOCATION: (5)..(5)
<223> OTHER INFORMATION: N-Methyl-L-Leucine

<400> SEQUENCE: 251

Xaa Thr Gly Xaa Xaa
1               5

<210> SEQ ID NO 252
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-Methyl-L-Leucine

<400> SEQUENCE: 252

Xaa Ala Gly Xaa Xaa
1               5

<210> SEQ ID NO 253
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
```

```
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 253

Xaa Ala Gly Xaa Xaa
1               5

<210> SEQ ID NO 254
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 254

Xaa Ala Gly Xaa Xaa
1               5

<210> SEQ ID NO 255
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 255

Xaa Ala Gly Xaa Xaa
1               5
```

```
<210> SEQ ID NO 256
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 256

Xaa Ala Gly Xaa Xaa
1               5

<210> SEQ ID NO 257
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 257

Xaa Ala Gly Xaa Xaa
1               5

<210> SEQ ID NO 258
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
```

```
<223> OTHER INFORMATION: N-Methyl-L-Leucine

<400> SEQUENCE: 258

Xaa Ala Gly Xaa Xaa
1               5

<210> SEQ ID NO 259
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 259

Xaa Ala Gly Xaa Xaa
1               5

<210> SEQ ID NO 260
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 260

Xaa Ala Gly Xaa Xaa
1               5

<210> SEQ ID NO 261
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
```

```
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-bromo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 261

Xaa Ala Gly Xaa Xaa
1               5

<210> SEQ ID NO 262
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-nitro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 262

Xaa Ala Gly Xaa Xaa
1               5

<210> SEQ ID NO 263
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 263

Xaa Ala Gly Xaa Xaa
1               5

<210> SEQ ID NO 264
<211> LENGTH: 5
<212> TYPE: PRT
<213> ORGANISM: Artificial Sequence
<220> FEATURE:
```

-continued

```
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-Methyl-L-Leucine

<400> SEQUENCE: 264

Xaa Ala Gly Xaa Xaa
1               5

<210> SEQ ID NO 265
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryrosine
<220> FEATURE:
<221> NAME/KEY: MOD_RES
<222> LOCATION: (5)..(5)
<223> OTHER INFORMATION: N-Methyl-L-Leucine

<400> SEQUENCE: 265

Xaa Ala Gly Xaa Xaa
1               5

<210> SEQ ID NO 266
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homotryptophane
<220> FEATURE:
<221> NAME/KEY: MOD_RES
<222> LOCATION: (5)..(5)
<223> OTHER INFORMATION: N-Methyl-L-Leucine

<400> SEQUENCE: 266

Xaa Ala Gly Xaa Xaa
```

<210> SEQ ID NO 267
<211> LENGTH: 6
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 267

Xaa Ala Gly Xaa Xaa Lys
1               5

<210> SEQ ID NO 268
<211> LENGTH: 6
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-Methyl-Alanine

<400> SEQUENCE: 268

Xaa Ala Gly Xaa Xaa Lys
1               5

<210> SEQ ID NO 269
<211> LENGTH: 6
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine

```
<220> FEATURE:
<221> NAME/KEY: MOD_RES
<222> LOCATION: (5)..(5)
<223> OTHER INFORMATION: N-Methyl-Isoleucine

<400> SEQUENCE: 269

Xaa Ala Gly Xaa Xaa Lys
1               5

<210> SEQ ID NO 270
<211> LENGTH: 6
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine
<220> FEATURE:
<221> NAME/KEY: MISC_FEATURE
<222> LOCATION: (6)..(6)
<223> OTHER INFORMATION: D-form Lysine

<400> SEQUENCE: 270

Xaa Ala Gly Xaa Xaa Lys
1               5

<210> SEQ ID NO 271
<211> LENGTH: 6
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine
<220> FEATURE:
<221> NAME/KEY: MOD_RES
<222> LOCATION: (6)..(6)
<223> OTHER INFORMATION: Diglycolic acid

<400> SEQUENCE: 271

Xaa Ala Gly Xaa Xaa Xaa
1               5

<210> SEQ ID NO 272
<211> LENGTH: 5
```

```
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 272

Xaa Ala Gly Xaa Xaa
1               5

<210> SEQ ID NO 273
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form Alanine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 273

Xaa Ala Gly Xaa Xaa
1               5

<210> SEQ ID NO 274
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: N-methyl-phenylalanine

<400> SEQUENCE: 274

Xaa Arg Xaa Lys
1
```

```
<210> SEQ ID NO 275
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: beta-homophenylalanine

<400> SEQUENCE: 275

Xaa Arg Xaa Lys
1

<210> SEQ ID NO 276
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine

<400> SEQUENCE: 276

Xaa Arg Tyr Lys
1

<210> SEQ ID NO 277
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: (S)-3-Amino-4-(4-methyl-phenyl)-butyric acid

<400> SEQUENCE: 277

Xaa Arg Xaa Lys
1

<210> SEQ ID NO 278
<211> LENGTH: 4
<212> TYPE: PRT
<213> ORGANISM: Artificial Sequence
<220> FEATURE:
<223> OTHER INFORMATION: Synthesized opioid agonist peptide
```

```
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: 4-Fluoro-L-Phenylalanine

<400> SEQUENCE: 278

Xaa Arg Xaa Lys
1

<210> SEQ ID NO 279
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine

<400> SEQUENCE: 279

Xaa Arg Trp Lys
1

<210> SEQ ID NO 280
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: (1-naphthyl)-L-alanine

<400> SEQUENCE: 280

Xaa Arg Xaa Lys
1

<210> SEQ ID NO 281
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form arginine
```

```
<220> FEATURE:
<221> NAME/KEY: MOD_RES
<222> LOCATION: (3)..(3)
<223> OTHER INFORMATION: (2-naphthyl)-L-alanine

<400> SEQUENCE: 281

Xaa Arg Xaa Lys
1

<210> SEQ ID NO 282
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine

<400> SEQUENCE: 282

Tyr Arg Phe Lys
1

<210> SEQ ID NO 283
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-methyl-beta alanine

<400> SEQUENCE: 283

Tyr Arg Phe Xaa
1

<210> SEQ ID NO 284
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (3)..(3)
<223> OTHER INFORMATION: D-form phenylalanine
<220> FEATURE:
<221> NAME/KEY: MISC_FEATURE
<222> LOCATION: (4)..(4)
<223> OTHER INFORMATION: D-form lysine

<400> SEQUENCE: 284

Xaa Arg Phe Lys
1

<210> SEQ ID NO 285
```

```
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: N-methyl beta alanine

<400> SEQUENCE: 285

Xaa Arg Phe Xaa
1

<210> SEQ ID NO 286
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (1)..(1)
<223> OTHER INFORMATION: D-form tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (3)..(3)
<223> OTHER INFORMATION: D-form phenylalanine
<220> FEATURE:
<221> NAME/KEY: MISC_FEATURE
<222> LOCATION: (4)..(4)
<223> OTHER INFORMATION: D-form lysine

<400> SEQUENCE: 286

Tyr Arg Phe Lys
1

<210> SEQ ID NO 287
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: D-form lysine

<400> SEQUENCE: 287

Tyr Arg Phe Lys
1

<210> SEQ ID NO 288
<211> LENGTH: 5
<212> TYPE: PRT
<213> ORGANISM: Artificial Sequence
<220> FEATURE:
```

```
<223> OTHER INFORMATION: Synthesized opioid agonist peptide
<220> FEATURE:
<221> NAME/KEY: MISC_FEATURE
<222> LOCATION: (3)..(3)
<223> OTHER INFORMATION: D-form arginine

<400> SEQUENCE: 288

Lys Tyr Arg Phe Lys
1               5

<210> SEQ ID NO 289
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (1)..(1)
<223> OTHER INFORMATION: D-form tyrosine
<220> FEATURE:
<221> NAME/KEY: MISC_FEATURE
<222> LOCATION: (2)..(2)
<223> OTHER INFORMATION: D-form arginine

<400> SEQUENCE: 289

Tyr Arg Phe Lys
1

<210> SEQ ID NO 290
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: 2,6-Dimethyl Tyrosine
<220> FEATURE:
<221> NAME/KEY: MISC_FEATURE
<222> LOCATION: (3)..(3)
<223> OTHER INFORMATION: D-form arginine
<220> FEATURE:
<221> NAME/KEY: MOD_RES
<222> LOCATION: (4)..(4)
<223> OTHER INFORMATION: (1-naphthyl)-L-alanine
<220> FEATURE:
<221> NAME/KEY: MOD_RES
<222> LOCATION: (5)..(5)
<223> OTHER INFORMATION: N-Methyl-beta-Alanine

<400> SEQUENCE: 290

Lys Xaa Arg Xaa Xaa
1               5

<210> SEQ ID NO 291
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
```

```
<223> OTHER INFORMATION: D-form arginine

<400> SEQUENCE: 291

Tyr Arg Phe Arg
1

<210> SEQ ID NO 292
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: N-methyl arginine

<400> SEQUENCE: 292

Tyr Arg Phe Xaa
1

<210> SEQ ID NO 293
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: D-form arginine

<400> SEQUENCE: 293

Tyr Arg Tyr Arg
1

<210> SEQ ID NO 294
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (3)..(3)
<223> OTHER INFORMATION: D-form tyrosine
<220> FEATURE:
<221> NAME/KEY: MISC_FEATURE
<222> LOCATION: (4)..(4)
<223> OTHER INFORMATION: D-form arginine

<400> SEQUENCE: 294

Tyr Arg Tyr Arg
1

<210> SEQ ID NO 295
<211> LENGTH: 4
<212> TYPE: PRT
<213> ORGANISM: Artificial Sequence
```

```
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: N-methyl-arginine
<220> FEATURE:
<221> NAME/KEY: MOD_RES
<222> LOCATION: (4)..(4)
<223> OTHER INFORMATION: N-methyl-lysine

<400> SEQUENCE: 295

Tyr Xaa Phe Xaa
1

<210> SEQ ID NO 296
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: N-methyl-arginine

<400> SEQUENCE: 296

Tyr Xaa Phe Lys
1

<210> SEQ ID NO 297
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: D-form norvaline
<220> FEATURE:
<221> NAME/KEY: MOD_RES
<222> LOCATION: (4)..(4)
<223> OTHER INFORMATION: ornithine

<400> SEQUENCE: 297

Tyr Xaa Phe Xaa
1

<210> SEQ ID NO 298
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: D-form norleucine
<220> FEATURE:
<221> NAME/KEY: MOD_RES
<222> LOCATION: (4)..(4)
<223> OTHER INFORMATION: ornithine

<400> SEQUENCE: 298

Tyr Xaa Phe Xaa
1

<210> SEQ ID NO 299
<211> LENGTH: 4
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: D-form ornithine
<220> FEATURE:
<221> NAME/KEY: MOD_RES
<222> LOCATION: (4)..(4)
<223> OTHER INFORMATION: ornithine

<400> SEQUENCE: 299

Tyr Xaa Phe Xaa
1

<210> SEQ ID NO 300
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: homo-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (3)..(3)
<223> OTHER INFORMATION: beta-homophenylalanine
<220> FEATURE:
<221> NAME/KEY: MISC_FEATURE
<222> LOCATION: (4)..(4)
<223> OTHER INFORMATION: D-form lysine

<400> SEQUENCE: 300

Xaa Arg Xaa Lys
1

<210> SEQ ID NO 301
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: homo-tyrosine
<220> FEATURE:
<221> NAME/KEY: MISC_FEATURE
<222> LOCATION: (2)..(2)
<223> OTHER INFORMATION: D-form arginine

<400> SEQUENCE: 301

Xaa Arg Phe Lys
1

<210> SEQ ID NO 302
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: homo-tyrosine
<220> FEATURE:
```

```
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-methyl-lysine

<400> SEQUENCE: 302

Xaa Arg Phe Xaa
1

<210> SEQ ID NO 303
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: N-methyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MOD_RES
<222> LOCATION: (4)..(4)
<223> OTHER INFORMATION: N-methyl-lysine

<400> SEQUENCE: 303

Xaa Arg Phe Xaa
1

<210> SEQ ID NO 304
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: N-methyl-tyrosine
<220> FEATURE:
<221> NAME/KEY: MISC_FEATURE
<222> LOCATION: (2)..(2)
<223> OTHER INFORMATION: D-form arginine
<220> FEATURE:
<221> NAME/KEY: MISC_FEATURE
<222> LOCATION: (4)..(4)
<223> OTHER INFORMATION: D-form lysine

<400> SEQUENCE: 304

Xaa Arg Phe Xaa
1

<210> SEQ ID NO 305
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form arginine
<220> FEATURE:
```

```
<221> NAME/KEY: MISC_FEATURE
<222> LOCATION: (4)..(4)
<223> OTHER INFORMATION: N-methyl phenylalanine

<400> SEQUENCE: 305

Xaa Arg Phe Xaa
1

<210> SEQ ID NO 306
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: sarcosine

<400> SEQUENCE: 306

Xaa Ala Phe Xaa
1

<210> SEQ ID NO 307
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (4)..(4)
<223> OTHER INFORMATION: Sarcosine

<400> SEQUENCE: 307

Xaa Pro Phe Xaa
1

<210> SEQ ID NO 308
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form proline
<220> FEATURE:
<221> NAME/KEY: MOD_RES
<222> LOCATION: (4)..(4)
<223> OTHER INFORMATION: Sarcosine

<400> SEQUENCE: 308

Xaa Pro Phe Xaa
1
```

```
<210> SEQ ID NO 309
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (4)..(4)
<223> OTHER INFORMATION: Sarcosine

<400> SEQUENCE: 309

Xaa Xaa Phe Xaa
1

<210> SEQ ID NO 310
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form proline
<220> FEATURE:
<221> NAME/KEY: MOD_RES
<222> LOCATION: (5)..(5)
<223> OTHER INFORMATION: Sarcosine

<400> SEQUENCE: 310

Xaa Pro Gly Phe Xaa
1               5

<210> SEQ ID NO 311
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (5)..(5)
<223> OTHER INFORMATION: Sarcosine

<400> SEQUENCE: 311

Xaa Xaa Gly Phe Xaa
1               5
```

```
<210> SEQ ID NO 312
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (3)..(3)
<223> OTHER INFORMATION: beta-homophenylalanine
<220> FEATURE:
<221> NAME/KEY: MOD_RES
<222> LOCATION: (4)..(4)
<223> OTHER INFORMATION: Sarcosine

<400> SEQUENCE: 312

Xaa Ala Xaa Xaa
1

<210> SEQ ID NO 313
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (3)..(3)
<223> OTHER INFORMATION: beta-homophenylalanine
<220> FEATURE:
<221> NAME/KEY: MOD_RES
<222> LOCATION: (4)..(4)
<223> OTHER INFORMATION: Sarcosine

<400> SEQUENCE: 313

Xaa Xaa Xaa Xaa
1

<210> SEQ ID NO 314
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: 2,6-Dimethyl Tyrosine
<220> FEATURE:
<221> NAME/KEY: MOD_RES
<222> LOCATION: (2)..(2)
<223> OTHER INFORMATION: 1,2,3,4,-tetrahydro-isoquinoline-3-carboxylic
      acid
<220> FEATURE:
<221> NAME/KEY: MOD_RES
<222> LOCATION: (4)..(4)
<223> OTHER INFORMATION: beta-homophenylalanine
<220> FEATURE:
```

```
<221> NAME/KEY: MOD_RES
<222> LOCATION: (5)..(5)
<223> OTHER INFORMATION: Sarcosine

<400> SEQUENCE: 314

Xaa Xaa Gly Xaa Xaa
1               5

<210> SEQ ID NO 315
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-methyl-Norleucine

<400> SEQUENCE: 315

Xaa Ala Gly Xaa Xaa
1               5

<210> SEQ ID NO 316
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homotryptophan
<220> FEATURE:
<221> NAME/KEY: MOD_RES
<222> LOCATION: (5)..(5)
<223> OTHER INFORMATION: N-methyl-Norleucine

<400> SEQUENCE: 316

Xaa Ala Gly Xaa Xaa
1               5

<210> SEQ ID NO 317
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
```

```
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: D-form N-methyl-phenylalanine

<400> SEQUENCE: 317

Xaa Ala Gly Xaa Xaa
1               5

<210> SEQ ID NO 318
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: D-form N-methyl-phenylalanine
<220> FEATURE:
<221> NAME/KEY: MOD_RES
<222> LOCATION: (5)..(5)
<223> OTHER INFORMATION: N-methyl-Norleucine

<400> SEQUENCE: 318

Xaa Ala Gly Xaa Xaa
1               5

<210> SEQ ID NO 319
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-methyl-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 319

Xaa Ala Gly Xaa Xaa
1               5

<210> SEQ ID NO 320
<211> LENGTH: 5
<212> TYPE: PRT
```

```
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-methyl-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 320

Xaa Ala Gly Xaa Xaa
1               5

<210> SEQ ID NO 321
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-methyl-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 321

Xaa Ala Gly Xaa Xaa
1               5

<210> SEQ ID NO 322
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(2-fluoro-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 322
```

```
Xaa Ala Gly Xaa Xaa
1               5

<210> SEQ ID NO 323
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-fluoro-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 323

Xaa Ala Gly Xaa Xaa
1               5

<210> SEQ ID NO 324
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-fluoro-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 324

Xaa Ala Gly Xaa Xaa
1               5

<210> SEQ ID NO 325
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
```

```
<222> LOCATION: (4)..(4)
<223> OTHER INFORMATION: (S)-3-Amino-4-(2-bromo-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 325

Xaa Ala Gly Xaa Xaa
1               5

<210> SEQ ID NO 326
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(3-chloro-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 326

Xaa Ala Gly Xaa Xaa
1               5

<210> SEQ ID NO 327
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: (S)-3-Amino-4-(4-iodo-phenyl)-butyric acid
<220> FEATURE:
<221> NAME/KEY: MOD_RES
<222> LOCATION: (5)..(5)
<223> OTHER INFORMATION: N-methyl-L-norleucine

<400> SEQUENCE: 327

Xaa Ala Gly Xaa Xaa
1               5

<210> SEQ ID NO 328
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
```

```
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homotyrosine
<220> FEATURE:
<221> NAME/KEY: MOD_RES
<222> LOCATION: (5)..(5)
<223> OTHER INFORMATION: N-methyl-L-norleucine

<400> SEQUENCE: 328

Xaa Ala Gly Xaa Xaa
1               5

<210> SEQ ID NO 329
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homotryptophan
<220> FEATURE:
<221> NAME/KEY: MOD_RES
<222> LOCATION: (5)..(5)
<223> OTHER INFORMATION: N-methyl-L-norleucine

<400> SEQUENCE: 329

Xaa Ala Gly Xaa Xaa
1               5

<210> SEQ ID NO 330
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form glutamic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: Sarcosine

<400> SEQUENCE: 330

Xaa Glu Gly Xaa Xaa
1               5
```

```
<210> SEQ ID NO 331
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-alanine

<400> SEQUENCE: 331

Xaa Asp Gly Xaa Xaa
1               5

<210> SEQ ID NO 332
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-alanine

<400> SEQUENCE: 332

Xaa Thr Gly Xaa Xaa
1               5

<210> SEQ ID NO 333
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form glutamic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
```

<223> OTHER INFORMATION: N-methyl-alanine

<400> SEQUENCE: 333

Xaa Glu Gly Xaa Xaa
1               5

<210> SEQ ID NO 334
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-isoleucine

<400> SEQUENCE: 334

Xaa Asp Gly Xaa Xaa
1               5

<210> SEQ ID NO 335
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-isoleucine

<400> SEQUENCE: 335

Xaa Thr Gly Xaa Xaa
1               5

<210> SEQ ID NO 336
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)

```
<223> OTHER INFORMATION: D-form glutamic acid
<220> FEATURE:
<221> NAME/KEY: MOD_RES
<222> LOCATION: (4)..(4)
<223> OTHER INFORMATION: L-beta-homophenylalanine
<220> FEATURE:
<221> NAME/KEY: MOD_RES
<222> LOCATION: (5)..(5)
<223> OTHER INFORMATION: N-methyl-isoleucine

<400> SEQUENCE: 336

Xaa Glu Gly Xaa Xaa
1               5

<210> SEQ ID NO 337
<211> LENGTH: 4
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MOD_RES
<222> LOCATION: (2)..(2)
<223> OTHER INFORMATION: beta-homophenylalanine
<220> FEATURE:
<221> NAME/KEY: MOD_RES
<222> LOCATION: (3)..(3)
<223> OTHER INFORMATION: sarcosine
<220> FEATURE:
<221> NAME/KEY: MISC_FEATURE
<222> LOCATION: (4)..(4)
<223> OTHER INFORMATION: D-form lysine

<400> SEQUENCE: 337

Gly Xaa Xaa Lys
1

<210> SEQ ID NO 338
<211> LENGTH: 5
<212> TYPE: PRT
<213> ORGANISM: Artificial Sequence
<220> FEATURE:
<223> OTHER INFORMATION: Synthesized opioid agonist peptide
<220> FEATURE:
<221> NAME/KEY: MISC_FEATURE
<222> LOCATION: (1)..(1)
<223> OTHER INFORMATION: D-form alanine
<220> FEATURE:
<221> NAME/KEY: MOD_RES
<222> LOCATION: (3)..(3)
<223> OTHER INFORMATION: beta-homophenylalanine
<220> FEATURE:
<221> NAME/KEY: MOD_RES
<222> LOCATION: (4)..(4)
<223> OTHER INFORMATION: sarcosine
<220> FEATURE:
<221> NAME/KEY: MISC_FEATURE
<222> LOCATION: (5)..(5)
<223> OTHER INFORMATION: D-form lysine

<400> SEQUENCE: 338

Ala Gly Xaa Xaa Lys
1               5

<210> SEQ ID NO 339
<211> LENGTH: 11
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(3)
```

```
<223> OTHER INFORMATION: Any amino acid or absent
<220> FEATURE:
<221> NAME/KEY: MOD_RES
<222> LOCATION: (4)..(4)
<223> OTHER INFORMATION: Tyr, D-form Tyr, a Tyr analog, Tic, a Tic
      analog, or a Phe analog
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (8)..(11)
<223> OTHER INFORMATION: Any amino acid or absent

<400> SEQUENCE: 339

Xaa Xaa Xaa Xaa Xaa Xaa Xaa Xaa Xaa Xaa Xaa
1               5                   10

<210> SEQ ID NO 340
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Substituted or unsubstituted Phe, substituted
      or unsubstituted b-homoPhe, or any N-methylamino acid
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 340

Xaa Xaa Xaa Xaa Xaa
1               5

<210> SEQ ID NO 341
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(4-COX)
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Substituted or unsubstituted Phe, substituted
      or unsubstituted b-homoPhe, or any N-methylamino acid
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 341
```

Xaa Xaa Xaa Xaa Xaa
1               5

<210> SEQ ID NO 342
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Substituted or unsubstituted Phe, substituted
      or unsubstituted b-homoPhe, or any N-methylamino acid
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 342

Tyr Xaa Xaa Xaa Xaa
1               5

<210> SEQ ID NO 343
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 343

Xaa Xaa Xaa Xaa Xaa
1               5

<210> SEQ ID NO 344
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(4-COX)
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine

```
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 344

Xaa Xaa Xaa Xaa Xaa
1               5

<210> SEQ ID NO 345
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 345

Tyr Xaa Xaa Xaa Xaa
1               5

<210> SEQ ID NO 346
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 346

Xaa Xaa Gly Xaa Xaa
1               5

<210> SEQ ID NO 347
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(4-COX)
<220> FEATURE:
```

```
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 347

Xaa Xaa Gly Xaa Xaa
1               5

<210> SEQ ID NO 348
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 348

Tyr Xaa Gly Xaa Xaa
1               5

<210> SEQ ID NO 349
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 349

Xaa Ala Gly Xaa Xaa
1               5

<210> SEQ ID NO 350
<211> LENGTH: 5
<212> TYPE: PRT
<213> ORGANISM: Artificial Sequence
```

```
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 350

Xaa Asp Gly Xaa Xaa
1               5

<210> SEQ ID NO 351
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 351

Xaa Thr Gly Xaa Xaa
1               5

<210> SEQ ID NO 352
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: L-2,6-Dimethyl-tyrosine
<220> FEATURE:
<221> NAME/KEY: MISC_FEATURE
<222> LOCATION: (2)..(2)
<223> OTHER INFORMATION: D-form glutamic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent
```

<400> SEQUENCE: 352

Xaa Glu Gly Xaa Xaa
1               5

<210> SEQ ID NO 353
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form alanine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 353

Xaa Ala Gly Xaa Xaa
1               5

<210> SEQ ID NO 354
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form aspartic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 354

Xaa Asp Gly Xaa Xaa
1               5

<210> SEQ ID NO 355
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE

```
<222> LOCATION: (2)..(2)
<223> OTHER INFORMATION: D-form threonine
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 355

Xaa Thr Gly Xaa Xaa
1               5

<210> SEQ ID NO 356
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Phe(2,6-dimethyl-4-CONH2)
<220> FEATURE:
<221> NAME/KEY: MISC_FEATURE
<222> LOCATION: (2)..(2)
<223> OTHER INFORMATION: D-form glutamic acid
<220> FEATURE:
<221> NAME/KEY: MOD_RES
<222> LOCATION: (4)..(4)
<223> OTHER INFORMATION: beta-homophenylalanine
<220> FEATURE:
<221> NAME/KEY: MOD_RES
<222> LOCATION: (5)..(5)
<223> OTHER INFORMATION: Any amino acid, or any N-methylamino acid or
      absent

<400> SEQUENCE: 356

Xaa Glu Gly Xaa Xaa
1               5

<210> SEQ ID NO 357
<211> LENGTH: 5
<212> TYPE: PRT
<213> ORGANISM: Artificial Sequence
<220> FEATURE:
<223> OTHER INFORMATION: Opioid agonist peptide formula
<220> FEATURE:
<221> NAME/KEY: MOD_RES
<222> LOCATION: (1)..(1)
<223> OTHER INFORMATION: Tyr, DMT, or a Phe(4-COX) analog
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Sar, or bhF unsubstituted or substituted with
      2-Me, 3-Me, 4-Me, 2-F, 3-F, 4-F, 2-Cl, 3-Cl, 4-Cl, 2-OH, 3-OH, or
      4-OH
<220> FEATURE:
<221> NAME/KEY: MOD_RES
<222> LOCATION: (5)..(5)
<223> OTHER INFORMATION: absent or any amino acid

<400> SEQUENCE: 357

Xaa Xaa Xaa Xaa Xaa
1               5
```